United States Patent [19]

Asrar et al.

[11] Patent Number: 6,091,002

[45] Date of Patent: Jul. 18, 2000

[54] POLYHYDROXYALKANOATES OF NARROW MOLECULAR WEIGHT DISTRIBUTION PREPARED IN TRANSGENIC PLANTS

[75] Inventors: Jawed Asrar, Chesterfield; Timothy A. Mitsky, Maryland Heights; Devang T. Shah, Chesterfield, all of Mo.

[73] Assignee: Monsanto Company, St. Louis, Mo.

[21] Appl. No.: 08/912,205

[22] Filed: Aug. 15, 1997

Related U.S. Application Data

[63] Continuation-in-part of application No. 08/673,388, Jun. 28, 1996, which is a continuation-in-part of application No. 08/628,039, Apr. 4, 1996, Pat. No. 5,942,660, which is a continuation-in-part of application No. 08/614,877, Mar. 13, 1996.

[51] Int. Cl.[7] .............................. A01H 1/02; C12N 15/82; C12P 7/62
[52] U.S. Cl. ........................... 800/288; 435/135; 800/260
[58] Field of Search .............................. 435/172.3, 320.1, 435/419, DIG. 1, 468, 135; 536/23.2, 23.7; 800/205, DIG. 43, DIG. 58, DIG. 42, DIG. 15, DIG. 56, DIG. 26, DIG. 17, DIG. 14, DIG. 23, DIG. 9, DIG. 55, DIG. 24, 278, 288, 298, 320.1, 317.3, 320.3, 306, 317.2, 322, 260

[56] References Cited

U.S. PATENT DOCUMENTS

| | | | |
|---|---|---|---|
| 5,250,430 | 10/1993 | Peoples et al. | 435/232 |
| 5,502,273 | 3/1996 | Bright et al. | 800/205 |
| 5,811,272 | 9/1998 | Snell et al. | 435/135 |

FOREIGN PATENT DOCUMENTS

| | | | |
|---|---|---|---|
| WO 94/02620 | 2/1994 | WIPO | C12N 15/82 |
| WO 95/27068 | 10/1995 | WIPO | C12N 15/82 |

OTHER PUBLICATIONS

Priefert et al., (1992) "Identification and Molecular Characterization of the Acetyl Coenzyme A Synthetase Gene (acoE) of *Alcaligenes eutrophus*," *Journal of Bacteriology*, 174:6590–6599.

Steinbuchel, (1991), "Polyhydroxyalkanoic Acids," *Biomaterials*, Stockton Press, New York, 125–213.

Fry et al., (1987) "Transformation of *Brassica napus* with *Agrobacterium tumefaciens* based vectors," *Plant Cell Reports*, 6:321–325.

Mourad et al., (1995) "L–O–Methylthreonine–ResistantMutant of Arabidopisis Defective in Isoleucine Feedback Regulation," *Plant Physiology*, 107:43–52.

Taillon et al., (1988) "Analysis of the functional domains of biosynthetic threonine deaminase by comparison of the amino acid sequence of three wild–type alleles to the amino acid sequence of biodegradative threonine deaminase," *Gene.*, 63:245–252.

Bisswanger, (1981), "Substrate Specificity of the Pyruvate Dehydrogenase Complex from *Escherichia coli*," *Journal of Biological Chemistry*, 256:815–822.

Nawrath et al., (1994) "Targeting of the polyhydroxybutyrate biosynthetic pathway to the plastids of *Arabidopsis thaliana* results in high levels of polymer accumulation," *Proceedings of National Academy of Science USA*, 91:12760–12764.

Poirier et al, (1992) "Polyhydroxybutyrate, a Biodegradable Thermoplastic, Produced in Transgenic Plants," *Science*, 256:520–523.

Haywood et al., (1988) "Characterization of two 3–ketothiolases possessing differing substrate specificities in the polyhydroxyalkanoate synthesizing organism *Alcaligenes eutrophus*," *Federation of European Microbiological Societies*, 52:91–96.

Manchak et al., (1994) "Control of polyhydroxyalkanoate synthesis in *Azotobacter vinelandii* strain UWD," *Microbiology*, 140:953–963.

Rhie et al., (1995) "Role of fadR and atoC(Con) Mutations in Poly(3–Hydroxybutyrate–Co–3–Hydroxyvalerate)Synthesis in Recombinant pha[+] *Escherichia coli*," *Applied and Environmental Microbiology*, 61:2487–2492.

Eisenstein et al., (1995) "An Expanded Two–State Model Accounts for Homotropic Cooperativity in Biosynthetic Threonine Deaminase from *Escherichia coli*," *Biochemistry*, 34:9403–9412.

Feldberg et al., (1971) "L–Threonine Deaminase of *Rhodospirillum rubrum*, Purification and Characterization," *European Journal Biochemistry*, 21:438–446.

Eisenstein, (1991) "Cloning, Expression, Purification, and Characterization of Biosynthetic Threonine Deaminase from *Escherichia coli*," *Journal of Biological Chemistry*, 266:5801–5807.

Nakamura et al., (1992) "Biosynthesis of poly(3–hydroxyalkanoate)from amino acids," *International Journal of Biological Macromol.*, 14:321–325.

Galili, (1995) "Regulation of Lysine and Threonine Synthesis," *The Plant Cell*, 7:899–906.

Slater et al., (1988) "Cloning and Expression in *Escherichia coli* of the *Alcaligenes eutrophus* H16 Poly–β–Hydroxybutyrate Biosynthetic Pathway," *Journal of Bacteriology*, 170:4431–4436.

Slater et al., (1992) "Production of Poly–(3–Hydroxybutyrate–Co–3–Hydroxyvalerate) in a Recombinant *Escherichia coli* Strain," *Applied and Environmental Microbiology*, 58:1089–1094.

Schubert et al., (1988) "Cloning of the *Alcaligenes eutrophus* Genes for Synthesis of Poly–β–Hydroxybutyric Acid (PHB) and Synthesis of PHB in *Escherichia coli*," *Journal of Bacteriology*, 170:5837–5847.

(List continued on next page.)

*Primary Examiner*—Lynette R. F. Smith
*Assistant Examiner*—Amy J. Nelson
*Attorney, Agent, or Firm*—Gary M. Bond; Arnold White & Durkee

[57] ABSTRACT

Methods for the biosynthesis of polyhydroxyalkanoate homopolymers and copolymers are described. In a preferred embodiment, the polymers have a single mode molecular weight distribution, and more preferably have a distribution of between about 2 and about 4, and most preferably about 2.1 or 2.5.

17 Claims, 27 Drawing Sheets

OTHER PUBLICATIONS

Peoples et al., (1989) "Poly–β–Hydroxybutyrate (PHB) Biosynthesis in *Alcaligenes eutrophus* H16," *Journal of Biological Chemistry*, 264:15293–15297.

Peoples et al., (1989) "Poly–β–hydroxybutyrate Biosynthesis in *Alcaligenes eutrophus* H16," *Journal of Biological Chemistry*, 264:15298–15303.

Barwale et al., (1986) "Plant regeneration from callus cultures of several soybean genotypes via embryogenesis and organogenesis," *Planta*, 167:473–481.

Cakmak et al., (1989) "Effect of Zinc Nutritional Status on Growth, Protein Metabolism and Levels of Indole–3–acetic Acid and other Phytohormones in Bean (*Phaseolus vulgaris* L.)," *Journal of Experimental Botany*, 40:405–412.

Wright et al., (1986), "Plant regeneration by organogenesis in *Glycine max*," *Plant Cell Reports*, 5:150–154.

Barwale et al., (1986) "Screening of *Glycine max* and *Glycine soja* genotypes for multiple shoot formation at the cotyledonary node," *Theoretical Applied Genetics*, 72:423–438.

Kim et al., (1994) "Synergistic effects of proline and inorganic micronutrients and effects of individual micronutrients on soybean (*Glycine max* shoot regeneration in vitro," *Journal Plant Physiology*, 144:726–734.

Yang et al., (1990) "Comparative studies of organogenesis and plant regeneration in various soybean explants," *Plant Science*, 72:101–108.

Chee et al., (1989) "Transformation of soybean (*Glycine max*) by infecting germinating seeds with *Agrobacterium tumefaceins*," *Plant Physiology*, 91:1212–1218.

Christou et al., (1992) "Prediction of germ–line transformation events in chimeric Ro transgenic soybean plantlets using tissue–specific expression patterns," *The Plant Journal*, 2:283–290.

Falco et al., (1995) "Transgenic canola and soybean seeds with increased lysine," *Bio/Technology*, 13:477–582.

Finer et al., (1991) "Transformation of soybean via particle bombardment of embryogenic suspension culture tissue," *In Vitro Cell. Dev. Biol.*, 27P–175–182.

Hinchee et al., (1988) "Production of transgenic soybean plants using Agrobacterium–mediatedDNA transfer," *Bio/Technology*, 6:915–922.

McCabe et al., (1988) "Stable transformation of soybean (*Glycine max*) by particle acceleration," *Bio/Technology*, 6:923–926.

Owens et al., (1985) "Genotypic variability of soybean response to Agrobacterium strains harboring the Ti or Ri plasmids," *Plant Physiology*, 77:87–94.

Parrott et al., (1994) "Recovery and evaluation of soybean plants transgenic for a *Bacillus thuringiensis* var. *Kurstaki* insecticidal gene," *In Vitro Cell. Dev. Biology*, 30P:144–149.

Padgette et al., (1995) "Development, identification and characterization of a glyphosate–tolerant soybean line," *Crop Science*, 35:1451–1461.

Cheng et al., (1980) "Plant regeneration from soybean cotyledonary node segments in culture," *Plant Science Letters*, 19:91–99.

van der Leji and Witholt, (1995) *Can. J. Microbiol.* 41(Suppl. 1): 222.

Odell et al., (1985) *Nature* 313: 810.

Jun Sim et. al., (1997) *Nature Biotechnology*, 15:63.

Donson et. al., (1991) "Systemic expression of a bacterial gene by a tobacco mosaic virus–based vector," *Proc. Nat'l Acad. Sci.* 88: 7204.

Chapman et. al., (1992) "Potato virus X as a vector for gene expression in plants," *Plant J.* 2: 549.

Boynton et. al., (1988) "Chloroplst Transformation in Chlamydomonas with High Velocity Microprojectiles," *Science* 240: 1534.

Svab et al., (1990) "Stable transformation of plastids in higher plants," *Proc. Nat'l Acad. Sci. USA* 87: 8526.

McBride et. al., (1995) "Amplification of a Chimeric Bacillus Gene in Chloroplasts Leads to an Extraordincary Level of an Insecticidal Protein in Tobacco," *Biotechnology* 13: 362.

Staub and Maliga, (1995) "Expression of a chimeric uidA gene indicateds that polycistronic mRNAs are efficiently translated in tobacco plastids," *Plant J.*, 7:845.

Doyle et al., (1986) "The Glycosylated Seed Storage proteins of *Glycine max* and *Phaseolus vulgaris*," *J. Biol. Chem.* 261: 9228.

Finnegan and McElroy, (1994) "Transgene Inactivation: Plants Fight Back!," *Bio/Technology*, 12:883.

Assaad et al., (1993) "Epigenetic repeat–induced gene silencing (RIGS) in Arabidopsis," *Plant Mol. Biol.*, 22:1067.

Vaucheret, H., (1993) "Identification of a general silencer for 19S and 35S promoters in a transgenic tobacco plant: 90 pb of homology in the promoter sequence are sufficient for trans–inactivation," *C.R. Acad. Sci. Paris, Science de la vie/Life Sciences*, 316:1471.

McElroy and Brettell, (1994) "Foreign gene expression in transgenic cereals," *TIBTECH*, 12:62.

Stief et al., (1989) "A nuclear DNA attachment element mediates elevated and position–independent gene activity," *Nature*, 341:343.

Breyne et al., (1992) " Characterization of a Plant Scaffold Attachment Region in a DNA Fragment That Normalizes Transgene Expression in Tobacco," *Plant Cell*, 4:463.

Allen et al., (1993) "Scaffold Attachment Regions Increase Reporter Gene Expression in Stably Transofrmed Plant Cells," *Plant Cell*, 5:603.

Mlynarova et al., (1994) "Reduced Position Effect in Mature Transgenic Plants Conferred by the Chicken Lysozyme Matrix–Associated Region," *Plant Cell*, 6:417.

Spiker and Thompson, (1996) "Nuclear Matrix Attachment Regions and Transgene Expression in Plants," *Plant Physiol.*, 110:15.

Register et al., (1994) "Structure and function of selectable and non–selectable transgenes in maize after introduction by particle bombardment," *Plant Mol. Biol.*, 25:951.

Yoder and Goldsbrough, (1994) "Transformation Systems for Generating Marker–Free Transgenic Plants," *Bio/Technol.*, 12:263–267.

Söhling and Gottschalk, (1996) "Molecular Analysis of the Anaerobic Succinate Degradation Pathway in *Clostridium kluveri*," *J. Bacteriol.*, 178:871–880.

Sim SJ, et al. "PHA synthase activity controls the molecular weight and polydiversity of polyhydroxybutyrate in vivo." Nature Biotech. 15: 63–67, Jan. 1997.

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Poirier Y, et al. "Polyhydroxybutyrate, a biodegradable thermoplastic, produced in transgenic plants." Science 256: 520–523, Apr. 24, 1992.

POLYHYDROXYALKANOATES OF NARROW MOLECULAR WEIGHT DISTRIBUTION PREPARED IN TRANSGENIC PLANTS

RELATED U.S. APPLICATION DATA

This application is a continuation-in-part of Ser. No. 08/673,388, Jun. 28, 1996, which is a continuation-in-part of Ser. No. 08/628,039, Apr. 4, 1996, now U.S. Pat. No. 5,942,660 which is a continuation-in-part of Ser. No. 08/614,877, Mar. 13, 1996.

FIELD OF INVENTION

The present invention relates to genetically engineered plants and bacteria. In particular, it relates to methods for optimizing substrate pools to facilitate the biosynthetic production of commercially useful levels of polyhydroxyalkanoates (PHAs) in bacteria and plants.

BACKGROUND OF INVENTION

PHAs are bacterial polyesters that accumulate in a wide variety of bacteria. These polymers have properties ranging from stiff and brittle plastics to rubber-like materials, and are biodegradable. Because of these properties, PHAs are an attractive source of nonpolluting plastics and elastomers.

The present invention especially relates to the production of copolyesters of β-hydroxybutyrate (3HB) and β-hydroxyvalerate (3HV), designated P(3HB-co-3HV) copolymer, and derivatives thereof.

Currently, there are approximately a dozen biodegradable plastics in commercial use that possess properties suitable for producing a number of specialty and commodity products (Lindsay, 1992). One such biodegradable plastic in the polyhydroxyalkanoate (PHA) family that is commercially important is Biopol™, a random copolymer of 3-hydroxybutyrate (3HB) and 3-hydroxyvalerate (3HV). This bioplastic is used to produce biodegradable molded material (e.g., bottles), films, coatings, and in drug release applications. Biopol™ is produced via a fermentation process employing the bacterium *Alcaligenes eutrophus* (Byrom, 1987). The current market price is $6–7/lb, and the annual production is 1,000 tons. By best estimates, this price can be reduced only about 2-fold via fermentation (Poirier et al., 1995). Competitive synthetic plastics such as polypropylene and polyethylene cost about 35–45¢/lb (Layman, 1994). The annual global demand for polyethylene alone is about 37 million metric tons (Poirier et al., 1995). It is therefore likely that the cost of producing P(3HB-co-3HV) by microbial fermentation will restrict its use to low-volume specialty applications.

Nakamura et al. (1992) reported using threonine (20 g/L) as the sole carbon source for the production of P(3HB-co-3HV) copolymer in *A. eutrophus*. These workers initially suggested that the copolymer might form via the degradation of threonine by threonine deaminase, with conversion of the resultant α-ketobutyrate to propionyl-CoA. However, they ultimately concluded that threonine was utilized directly, without breaking carbon-carbon bonds, to form valeryl-CoA as the 3HV precursor. The nature of this chemical conversion was not described, but since the breaking of carbon—carbon bonds was not postulated to occur, the pathway could not involve threonine deaminase in conjunction with an α-ketoacid decarboxylating step to form propionate or propionyl-CoA. In the experiments of Nakamura et al., the PHA polymer content was very low (<6% of dry cell weight). This result, in conjunction with the expense of feeding bacteria threonine, makes their approach impractical for the commercial production of P(3HB-co3HV) copolymer.

Yoon et al. (1995) have shown that growth of *Alcaligenes* sp. SH-69 on a medium supplemented with threonine, isoleucine, or valine resulted in significant increases in the 3HV fraction of the P(3HB-co-3HV) copolymer. In addition to these amino acids, glucose (3% wt/vol) was also added to the growth media. In contrast to the results obtained by Nakamura et al. (1992), growth of *A. eutrophus* under the conditions described by Yoon et al. (1995) did not result in the production of P(3HB-co-3HV) copolymer when the medium was supplemented with threonine as the sole carbon source. From their results, Yoon et al. (1995) implied that the synthetic pathway for the 3HV component in P(3HB-co-3HV) copolymer is likely the same as that described in WO 91/18995 and Steinbuichel and Pieper (1992). This postulated synthetic pathway involves the degradation of isoleucine to propionyl-CoA (FIG. 3).

U.S. Pat. No. 5,602,321 teaches the insertion and expression of polymer biosynthesis genes in plants, and preferably in cotton. Genetic constructs encoding ketothiolase, acetoacetyl CoA reductase, and PHB synthase enzymes were introduced into cotton.

Sim et al. (1997) reported that the amount of polyhydroxyalkanoate synthase protein in a bacterial cell affected the molecular weight and polydispersity of polymers produced therein. Increased synthase concentrations led to the biosynthesis of lower molecular weight polymer.

John and Keller (1996) obtained polyhydroxybutyrate from cotton transformed with the phaB and phaC genes from *Alcaligenes eutrophus*. A major fraction of the polymer obtained had a molecular weight in excess of 600,000. Polydispersity of the polymer is not discussed, nor is sufficient data presented to allow calculation thereof.

Poirier et al. (1995b) described the biosynthesis of polyhydroxybutyrate in a suspension culture of *Arabidopsis thaliana* plant cells expressing the phbB and phbC genes from *Alcaligenes eutrophus*. No C3 or C5 3-hydroxyacids were detected by gas chromatography of plant extracts. The polyhydroxybutyrate was found to have a broad molecular weight distribution of 10.5. Unlike bacterially produced polymer, the plant cell produced material displayed a polymodal distribution, comprising at least three distinct subpopulations of molecular weight ranges.

The PHB Biosynthetic Pathway

Polyhydroxybutyrate (PHB) was first discovered in 1926 as a constituent of the bacterium *Bacillus megaterium* (Lemoigne, 1926). Since then, PHAs such as PHB have been found in more than 90 different genera of gram-negative and gram-positive bacteria (Steinbüichel, 1991). These microorganisms produce PHAs using R-β-hydroxyacyl-CoAs as the direct metabolic substrate for a PHA synthase, and produce polymers of R-(3)-hydroxyalkanoates having chain lengths ranging from C3–C14 (Steinbüchel and Valentin, 1995).

To date, the best understood biochemical pathway for PHB production is that found in the bacterium *Alcaligenes eutrophus* (Dawes and Senior, 1973; Slater et al., 1988; Schubert et al., 1988; Peoples and Sinskey, 1989a and 1989b). This pathway, which is also utilized by other microorganisms, is summarized in FIG. 1. In this organism, an operon encoding three gene products, i.e., PHB synthase, O-ketothiolase, and acetoacetyl-CoA reductase, encoded by the phbC, phbA, and phbB genes, respectively, are required to produce the PHA homopolymer R-polyhydroxybutyrate (PHB).

As further shown in FIG. 1, acetyl-CoA is the starting substrate employed in the biosynthetic pathway. This metabolite is naturally available for PHB production in plants and bacteria when these organisms are genetically manipulated to produce the PHB polyester.

Recently, a multi-enzyme pathway was successfully introduced into plants for the generation of polyhydroxybutyrate (PHB) (Poirier et al., 1992).

The P(3HB-co-3HV) Copolymer Biosynthetic Pathway

As noted above, P(3HB-co-3HV) random copolymer, commercially known as Biopol™, is produced by fermentation employing A. eutrophus. A proposed biosynthetic pathway for P(3HB-co-3HV) copolymer production is shown in FIG. 2. Production of this polymer in plants has not yet been demonstrated.

The successful production of P(3HB-co-3HV) copolymer in plants or bacteria requires the generation of substrates that can be utilized by the PHA biosynthetic enzymes. For the 3HB component of the polymer, the substrate naturally exists in plants in sufficient concentration in the form of acetyl-CoA (Nawrath et al., 1994). This is not true for the 3HV component of the copolymer, however. In this case, the starting substrate is propionyl-CoA. The presence of sufficient pools of acetyl-CoA and propionyl-CoA in plants and microorganisms, along with the proper PHA biosynthetic enzymes (i.e., a β-ketothiolase, a β-ketoacyl-CoA reductase, and a PHA synthase), would make it possible to produce copolyesters of P(3HB-co-3HV) in these organisms.

SUMMARY OF THE INVENTION

The present invention provides a variety of different methods for optimizing levels of is substrates employed in the biosynthesis of copolymers of 3-hydroxybutyrate (3HB) and 3-hydroxyvalerate (3HV) in plants and bacteria via manipulation of normal metabolic pathways using recombinant DNA techniques.

In one aspect, the present invention provides methods for the production of enhanced levels of threonine, α-ketobutyrate, propionyl-CoA, β-ketovaleryl-CoA, and β-hydroxyvaleryl-CoA, all of which are metabolites in the biosynthetic pathway of 3HV in the P(3HB-co-3HV) copolymer, from various carbon sources in plants or bacteria. This is achieved by providing a variety of wild-type and/or deregulated enzymes involved in the biosynthesis of the aspartate family of amino acids (i.e., aspartate, threonine, lysine, and methionine), and wild-type or deregulated forms of enzymes involved in the conversion of threonine to P(3HB-co-3HV) copolymer endproduct. Using these enzymes, the levels of the above-noted metabolites can be increased in plants and bacteria in the range of from about 1–10 fold, 1–100 fold, or 1–1000 fold.

In another aspect, the present invention provides methods for the biological production of P(3HB-co-3HV) copolymers in plants and bacteria utilizing propionyl-CoA as a substrate. As shown in FIG. 3, propionyl-CoA can be produced through a variety of engineered metabolic pathways. Introduction into plants and bacteria of appropriate β-ketothiolases capable of condensing acetyl-CoA with itself and/or with propionyl-CoA, along with appropriate β-ketoacyl-CoA reductases and PHA synthases, in combination with various enzymes involved in asparate family amino acid biosynthesis and the conversion of threonine to PHA copolymer precursors, will permit these organisms to produce P(3HB-co-3HV) copolymers. The PHA biosynthetic enzymes can be those of A. eutrophus or other organisms, or enzymes that catalyze reactions involved in fatty acid biosynthesis or degradation, ultimately resulting in the conversion of acetyl-CoA and propionyl-CoA to P(3HB-co-3HV). In plants, these enzymes can be expressed in the cytoplasm or targeted to organelles such as plastids (e.g., those of leaves or seeds) or mitochondria via the use of transit peptides for enhanced production of polyhydroxyalkanoates. Alternatively, plastids can be transformed with recombinant constructs that facilitate expression of these enzymes directly within the plastids themselves.

The enzymes discussed herein can be employed alone or in various combinations in order to enhance the levels of threonine, α-ketobutyrate, propionate, propionyl-CoA, β-ketovaleryl-CoA, and β-hydroxyvaleryl-CoA, and for the production of P(3HB-co-3HV) copolymer.

BRIEF DESCRIPTION OF THE DRAWINGS

The above and other aspects, features, and advantages of the present invention will be better understood from the following detailed description taken in conjunction with the accompanying drawings, all of which are given by way of illustration only and are not limitative of the present invention.

For the sake of brevity, a description of many of the common genetic elements present in each of the plasmid figures is not included in each figure legend. These genetic elements include Amp (ampicillin bacterial resistance); Spec or Spc/Str (spectinomycin bacterial resistance); Kan or Kan903 (kanamycin bacterial resistance); P-Sp6 (Sp6 RNA polymerase promoter); P-T7 (T7 RNA polymerase promoter); ori-pUC; ori-327; and ori-322 (each designation refers to the ColE1 plasmid origin of DNA replication of E. coli); ori-M13 (M13 phage origin of replication); ori-pACYC (plasmid origin of DNA replication of E. coli); ptrc and ptac (IPTG-inducible E. coli Trp/Lac fusion promoters); G10 (T7 gene 10 translational enhancing leader); precA (recA SOS responsive promoter); e35S, p7S, and P-FMV (promoters for plant expression); ARABSSU1A or PEPSPS-transit:2 (chloroplast transit peptides); E9 3' and NOS 3' (plant polyadenylation/transcription termination signals); ori-V (Agrobacterium origin of replication).

DETAILED DESCRIPTION OF THE INVENTION

Figure 1:
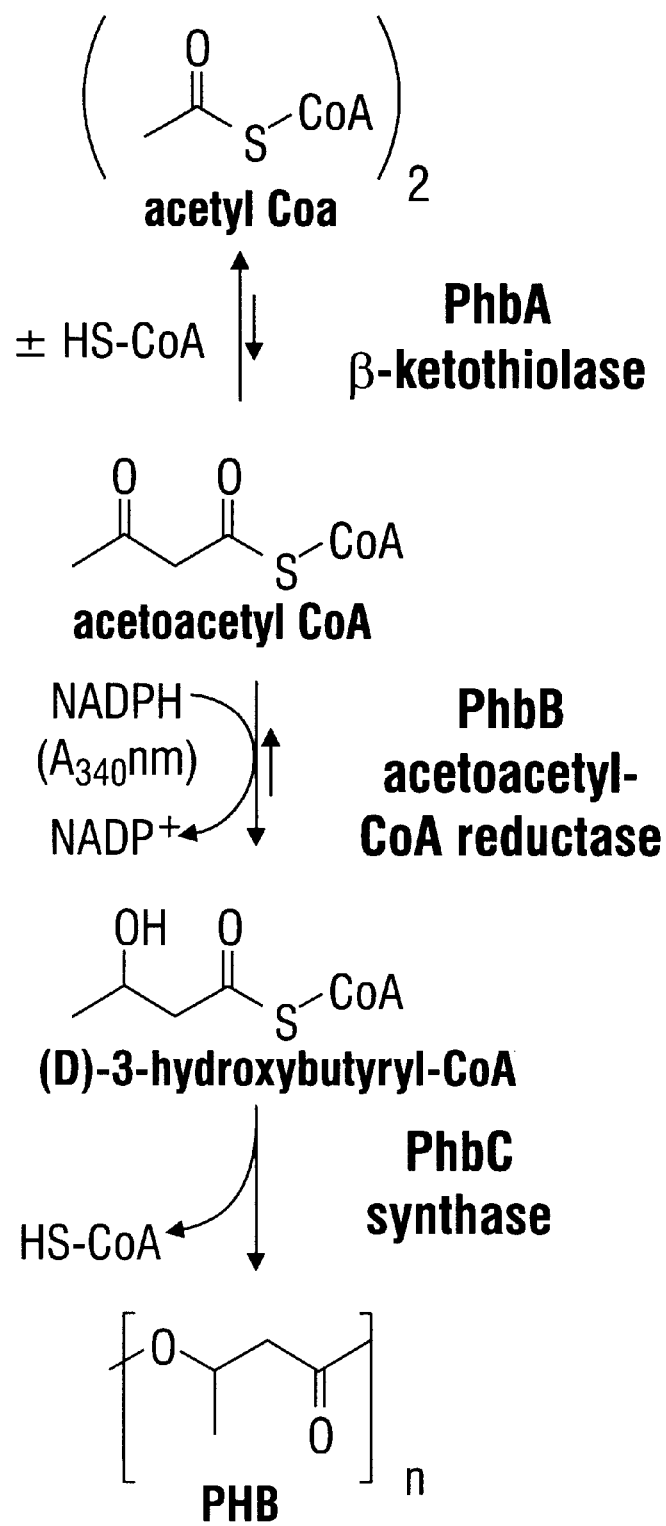
FIG. 1 shows the biochemical steps involved in the production of PHB from acetyl-CoA catalyzed by the A. eutrophus PHB biosynthetic enzymes.

More specifically, the present invention encompasses the following aspects:

is An isoleucine-deregulated mutein of E. coli threonine deaminase, wherein leucine at amino acid position 447 is replaced with an amino acid selected from the group consisting of alanine, isoleucine, valine, proline, phenylalanine, tryptophan, and methionine. In one aspect, leucine at amino acid position 447 can be replaced with phenylalanine.

An isoleucine-deregulated mutein of E. coli threonine deaminase, wherein leucine at amino acid position 447 is replaced with an amino acid selected from the group consisting of alanine, isoleucine, valine, proline, phenylalanine, tryptophan, and methionine, and leucine at amino acid position 481 is replaced with an amino acid selected from the group consisting of alanine, isoleucine, valine, proline, phenylalanine, tryptophan, and methionine. In one aspect, leucine at amino acid position 447 can be replaced with phenylalanine, and leucine at amino acid position 481 can be replaced with phenylalanine.

An α-ketoacid dehydrogenase complex, comprising an α-ketoacid decarboxylase E1 subunit, a dihydrolipoyl transacylase E2 subunit, and a dihydrolipoyl dehydrogenase E3 subunit, wherein said α-ketoacid decarboxylase E1 subunit exhibits improved binding and decarboxylating properties with α-ketobutyrate compared to pyruvate decarboxylase E1 subunit naturally present in a host cell pyruvate dehydrogenase complex. The α-ketoacid decarboxylase E1 subunit can be a branched-chain α-ketoacid decarboxylase E1 subunit such as bovine kidney, Pseudomonas putida, or Bacillus subtilis branched-chain α-ketoacid dehydrogenase E1 subunit.

An α-ketoacid dehydrogenase complex, comprising an α-ketoacid decarboxylase E1 subunit, a dihydrolipoyl transacylase E2 subunit, and a dihydrolipoyl dehydrogenase E3 subunit, wherein said E1 and E2 subunits exhibit improved binding/decarboxylating and transacylase properties, respectively, with α-ketobutyrate compared with pyruvate decarboxylase E1 subunit and dihydrolipoyl transacetylase E2 subunit, respectively, naturally present in a host cell pyruvate dehydrogenase complex. The α-ketoacid decarboxylase E1 and dihydrolipoyl transacylase E2 subunits can be branched-chain α-ketoacid dehydrogenase E1 and E2 subunits such as those from bovine kidney, *Pseudomonas putida*, or *Bacillus subtilis*.

An isolated β-ketothiolase capable of condensing acetyl-CoA and propionyl-CoA to produce β-ketovaleryl-CoA.

An isolated β-ketothiolase capable of condensing acetyl-CoA and butyryl-CoA to produce β-ketocaproyl-CoA.

An isolated β-ketothiolase capable of:
  condensing two molecules of acetyl-CoA to produce acetoacetyl-CoA;
  condensing acetyl-CoA and propionyl-CoA to produce β-ketovaleryl-CoA; and
  condensing acetyl-CoA and butyryl-CoA to produce β-ketcaproyl-CoA.

The foregoing isolated β-ketothiolase is exemplified by BktB β-keto-thiolase having the amino acid sequence shown in SEQ ID NO:11.

Isolated DNA molecules comprising a nucleotide sequence encoding the isoleucine-deregulated muteins of *E. coli* threonine deaminase described herein.

An isolated DNA molecule comprising the nucleotide sequence shown in SEQ ID NO:5.

An isolated DNA molecule comprising the nucleotide sequence shown in SEQ ID NO:8.

An isolated DNA molecule comprising a nucleotide sequence selected from the group consisting of:
  (a) the nucleotide sequence shown in SEQ ID NO:9 or the complement thereof;
  (b) a nucleotide sequence that hybridizes to said nucleotide sequence of (a) under a wash stringency equivalent to 0.5×SSC to 2×SSC, 0.1% SDS, at 55–65° C., and which encodes an enzyme having enzymatic activity similar to that of *A. eutrophus* BktB β-ketothiolase;
  (c) a nucleotide sequence encoding the same genetic information as said nucleotide sequence of (a), but which is degenerate in accordance with the degeneracy of the genetic code; and
  (d) a nucleotide sequence encoding the same genetic information as said nucleotide sequence of (b), but which is degenerate in accordance with the degeneracy of the genetic code.

The foregoing isolated DNA molecule, wherein said wash stringency is equivalent to 2×SSC, 0.1% SDS, at 55° C.

The foregoing isolated DNA molecule, wherein said wash stringency is equivalent to 1×SSC, 0.1% SDS, at 55° C.

The foregoing isolated DNA molecule, wherein said wash stringency is equivalent to 0.5×SSC, 0.1% SDS, at 55° C.

An isolated DNA molecule, comprising the nucleotide sequence shown in SEQ ID NO:9 or the complement thereof.

A recombinant vector, comprising any of the foregoing nucleotide sequences operatively linked to a promoter and 5' and 3' regulatory sequences sufficient to drive expression of said nucleotide sequences in a host cell.

A recombinant vector, comprising a nucleotide sequence encoding *E. coli* threonine deaminase wherein leucine at position 481 is replaced with phenylalanine, operatively linked to a promoter and 5' and 3' regulatory sequences sufficient to drive expression of said nucleotide sequence in a host cell.

The foregoing recombinant vector, wherein said nucleotide sequence comprises the sequence shown in SEQ ID NO:7.

A host cell, comprising any of the foregoing recombinant vectors.

A host cell, comprising an α-ketoacid dehydrogenase complex comprising an α-ketoacid decarboxylase E1 subunit, a dihydrolipoyl transacylase E2 subunit, and a dihydrolipoyl dehydrogenase E3 subunit, wherein said α-ketoacid decarboxylase E1 subunit exhibits improved binding and decarboxylating properties with α-ketobutyrate compared to pyruvate decarboxylase E1 subunit naturally present in a host cell pyruvate dehydrogenase complex, wherein said host cell produces an increased amount of propionyl-CoA compared to a corresponding host cell comprising wild-type pyruvate dehydrogenase complex. The α-ketoacid decarboxylase E1 subunit which exhibits improved binding and decarboxylating properties with α-ketobutyrate can be a branched-chain α-ketoacid decarboxylase E1 subunit.

A host cell, comprising an α-ketoacid dehydrogenase complex, comprising an α-ketoacid decarboxylase E1 subunit, a dihydrolipoyl transacylase E2 subunit, and a dihydrolipoyl dehydrogenase E3 subunit, wherein said E1 and E2 subunits exhibit improved binding/decarboxylating and transacylase properties, respectively, with α-ketobutyrate compared with pyruvate decarboxylase E1 subunit and dihydrolipoyl transacetylase E2 subunit, respectively, naturally present in a host cell pyruvate dehydrogenase complex, wherein said host cell produces an increased amount of propionyl-CoA compared to a corresponding host cell comprising wild-type pyruvate dehydrogenase complex.

A plant, the genome of which comprises introduced DNA encoding a wild-type or deregulated aspartate kinase enzyme;
  wherein said introduced DNA is operatively linked to regulatory signals that cause expression of said introduced DNA; and
  wherein cells of said plant produce an elevated amount of threonine compared to that in cells of a corresponding, wild-type plant not comprising said introduced DNA.

A plant, the genome of which comprises introduced DNAs encoding the following enzymes:
  a wild-type or deregulated aspartate kinase enzyme; and
  threonine synthase;
  wherein said introduced DNAs are operatively linked to regulatory signals that cause expression of said introduced DNAs; and
  wherein cells of said plant produce an elevated amount of threonine compared to that in cells of a corresponding, wild-type plant not comprising said introduced DNAs.

A plant, the genome of which comprises introduced DNAs encoding the following enzymes:
  a wild-type or deregulated aspartate kinase; and
  homoserine dehydrogenase;
  wherein each of said introduced DNAs is operatively linked to regulatory signals that cause expression of said introduced DNAs; and
  wherein cells of said plant produce an elevated amount of threonine compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase; and threonine synthase;

wherein each of said introduced DNAs is operatively linked to regulatory signals that cause expression of said introduced DNAs; and wherein cells of said plant produce an elevated amount of threonine compared to that in cells of a corresponding, wild-type plant not comprising said introduced DNAs.

A plant, the genome of which comprises introduced DNAs encoding the following enzymes:

a wild-type or deregulated aspartate kinase; and a wild-type or deregulated threonine deaminase;

wherein each of said introduced DNAs is operatively linked to regulatory signals that cause expression of said introduced DNAs; and wherein cells of said plant produce an elevated amount of α-ketobutyrate compared to that in cells of a corresponding, wild-type plant not comprising said introduced DNAs.

A plant, the genome of which comprises introduced DNAs encoding the following enzymes:

a wild-type or deregulated aspartate kinase;

threonine synthase; and a wild-type or deregulated threonine deaminase;

wherein each of said introduced DNAs is operatively linked to regulatory signals that cause expression of said introduced DNAs; and wherein cells of said plant produce an elevated amount of α-ketobutyrate compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase; and a wild-type or deregulated threonine deaminase;

wherein each of said introduced DNAs is operatively linked to regulatory signals that cause expression of said introduced DNAs; and wherein cells of said plant produce an increased amount of α-keto-butyrate compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase;

threonine synthase; and a wild-type or deregulated threonine deaminase;

wherein each of said introduced DNAs is operatively linked to regulatory signals that cause expression of said introduced DNAs; and wherein cells of said plant produce an increased amount of α-keto-butyrate compared to that in cells of a corresponding, wild-type plant not comprising said introduced DNAs.

A plant, the genome of which comprises introduced DNAs encoding the following enzymes:

a wild-type or deregulated threonine deaminase; and an α-ketoacid decarboxylase E1 subunit enzyme that exhibits improved binding and decarboxylating activities with α-ketobutyrate compared with pyruvate decarboxylase E1 subunit naturally present in pyruvate dehydrogenase complex of said plant;

wherein each of said introduced DNAs is operatively linked to regulatory signals that cause expression of said introduced DNAs; and wherein cells of said plant produce an elevated amount of propionyl-CoA compared to that in cells of a corresponding, wild-type plant not comprising said introduced DNAs.

The foregoing plant, wherein said α-ketoacid decarboxylase E1 subunit that exhibits improved binding and decarboxylating activities with α-ketobutyrate is a branched chain α-ketoacid decarboxylase E1 subunit such as that from bovine kidney, *Pseudomonas putida*, or *Bacillus subtilis*.

A plant, the genome of which comprises introduced DNAs encoding the following enzymes:

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant; and a dihydrolipoyl transacylase E2 subunit exhibiting improved transacylase activity with α-ketobutyrate compared with dihydrolipoyl transacetylase E2 subunit naturally present in pyruvate dehydrogenase complex in said plant;

wherein each of said introduced DNAs is operatively linked to regulatory signals that cause expression of said introduced DNAs; and wherein cells of said plant produce an elevated amount of propionyl-CoA compared to that in cells of a corresponding, wild-type plant not comprising said introduced DNAs.

The foregoing plant, wherein said α-ketoacid decarboxylase E1 subunit that exhibits improved binding and decarboxylating activities with α-ketobutyrate is a branched chain α-ketoacid decarboxylase E1 subunit such as that from bovine kidney, *Pseudomonas putida*, or *Bacillus subtilis*, and said dihydrolipoyl transacylase E2 subunit exhibiting improved transacylase activity with α-ketobutyrate is a branched chain dihydrolipoyl transacylase E2 subunit such as that from bovine kidney, *Pseudomonas putida*, or *Bacillus subtilis*.

A plant, the genome of which comprises introduced DNAs encoding the following enzymes:

a wild-type or deregulated threonine deaminase; and pyruvate oxidase;

wherein each of said introduced DNAs is operatively linked to regulatory signals that cause expression of said introduced DNAs; and wherein cells of said plant produce an elevated amount of propionyl-CoA compared that in cells of a corresponding, wild-type plant not comprising said introduced DNAs.

A plant, the genome of which comprises introduced DNAs encoding the following enzymes:

threonine synthase;

a wild-type or deregulated threonine deaminase; and pyruvate oxidase;

wherein each of said introduced DNAs is operatively linked to regulatory signals that cause expression of said introduced DNAs; and wherein cells of said plant produce an elevated amount of propionyl-CoA compared to that in cells of a corresponding, wild-type plant not comprising said introduced DNAs.

A plant, the genome of which comprises introduced DNAs encoding the following enzymes:
- a wild-type or deregulated threonine deaminase;
- pyruvate oxidase; and
- an acyl-CoA synthetase;
- wherein each of said introduced DNAs is operatively linked to regulatory signals that cause expression of said introduced DNAs; and
- wherein cells of said plant produce an elevated amount of propionyl-CoA compared to that in cells of a corresponding, wild-type plant not comprising said introduced DNAs.

A plant, the genome of which comprises introduced DNAs encoding the following enzymes:
- threonine synthase;
- a wild-type or deregulated threonine deaminase;
- pyruvate oxidase; and
- an acyl-CoA synthetase;
- wherein each of said introduced DNAs is operatively linked to regulatory signals that cause expression of said introduced DNAs; and
- wherein cells of said plant produce an elevated amount of propionyl-CoA compared to that in cells of a corresponding, wild-type plant not comprising said introduced DNAs.

A plant, the genome of which comprises introduced DNAs encoding the following enzymes:
- a wild-type or deregulated threonine deaminase;
- pyruvate oxidase;
- a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or
- a β-ketothiolase capable of condensing two molecules of acetyl-CoA to produce acetoacetyl-CoA, and capable of condensing acetyl-CoA and propionyl-CoA to produce β-ketovaleryl-CoA;
- a β-ketoacyl-CoA reductase capable of reducing acetoacetyl-CoA and β-ketovaleryl-CoA to produce β-hydroxybutyryl-CoA and β-hydroxy-valeryl-CoA, respectively; and
- a polyhydroxyalkanoate synthase capable of incorporating β-hydroxybutyryl-CoA and β-hydroxyvaleryl-CoA into P(3HB-co-3HV) copolymer;
- wherein each of said introduced DNAs is operatively linked to regulatory signals that cause expression of said introduced DNAs; and
- wherein said plant produces P(3HB-co-3HV) copolymer.

A plant, the genome of which comprises introduced DNAs encoding the following enzymes:
- threonine synthase;
- a wild-type or deregulated threonine deaminase;
- pyruvate oxidase;
- a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or
- a β-ketothiolase capable of condensing two molecules of acetyl-CoA to produce acetoacetyl-CoA, and capable of condensing acetyl-CoA and propionyl-CoA to produce β-ketovaleryl-CoA;
- a β-ketoacyl-CoA reductase capable of reducing acetoacetyl-CoA and β-ketovaleryl-CoA to produce β-hydroxybutyryl-CoA and β-hydroxy-valeryl-CoA, respectively; and
- a polyhydroxyalkanoate synthase capable of incorporating β-hydroxybutyryl-CoA and β-hydroxyvaleryl-CoA into P(3HB-co-3HV) copolymer;
- wherein each of said introduced DNAs is operatively linked to regulatory signals that cause expression of said introduced DNAs; and
- wherein said plant produces P(3HB-co-3HV) copolymer.

A plant, the genome of which comprises introduced DNAs encoding the following enzymes:
- a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or
- a β-ketothiolase capable of condensing two molecules of acetyl-CoA to produce acetoacetyl-CoA, and capable of condensing acetyl-CoA and propionyl-CoA to produce β-ketovaleryl-CoA;
- a β-ketoacyl-CoA reductase capable of reducing acetoacetyl-CoA and β-ketovaleryl-CoA to produce β-hydroxybutyryl-CoA and β-hydroxy-valeryl-CoA, respectively; and
- a polyhydroxyalkanoate synthase capable of incorporating β-hydroxybutyryl-CoA and β-hydroxyvaleryl-CoA into P(3HB-co-3HV) copolymer;
- wherein each of said introduced DNAs is operatively linked to regulatory signals that cause expression of said introduced DNAs; and
- wherein said plant produces P(3HB-co-3HV) copolymer.

The foregoing plant, the genome of which further comprises introduced DNA encoding a wild-type or deregulated threonine deaminase;
- wherein said introduced DNA is operatively linked to regulatory signals that cause expression of said introduced DNA; and
- wherein said plant produces P(3HB-co-3HV) copolymer.

A plant, the genome of which comprises introduced DNAs encoding the following enzymes:
- threonine synthase;
- a wild-type or deregulated threonine deaminase;
- a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or
- a β-ketothiolase capable of condensing two molecules of acetyl-CoA to produce acetoacetyl-CoA, and capable of condensing acetyl-CoA and propionyl-CoA to produce β-ketovaleryl-CoA;
- a β-ketoacyl-CoA reductase capable of reducing acetoacetyl-CoA and β-ketovaleryl-CoA to produce β-hydroxybutyryl-CoA and β-hydroxy-valeryl-CoA, respectively; and
- a polyhydroxyalkanoate synthase capable of incorporating β-hydroxybutyryl-CoA and β-hydroxyvaleryl-CoA into P(3HB-co-3HV) copolymer;
- wherein each of said introduced DNAs is operatively linked to regulatory signals that cause expression of said introduced DNAs; and
- wherein said plant produces P(3HB-co-3HV) copolymer.

Any of the foregoing plants, wherein the β-ketothiolase capable of condensing acetyl-CoA and propionyl-CoA to produce β-ketovaleryl-CoA is BktB.

Any of the foregoing plants, wherein said β-ketoacyl-CoA reductase is obtainable from a microorganism selected from the group consisting of *Alcaligenes eutrophus, Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum*, and *Thiocapsa pfennigii*.

Any of the foregoing plants, wherein said polyhydroxyalkanoate synthase is obtainable from a microorganism selected from the group consisting of *Alcaligenes eutrophus, Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum*, and *Thiocapsa pfennigii*.

A plant, the genome of which comprises introduced DNA encoding a wild-type or deregulated threonine deaminase enzyme;
- wherein said introduced DNA is operatively linked to regulatory signals that cause expression of said introduced DNA; and
- wherein cells of said plant produce an increased amount of α-keto-butyrate compared to that in cells of a corresponding, wild-type plant not comprising said introduced DNA.

A plant, the genome of which comprises introduced DNAs encoding the following enzymes:
- threonine synthase; and
- a wild-type or deregulated threonine deaminase;
- wherein said introduced DNAs are operatively linked to regulatory signals that cause expression of said introduced DNAs; and
- wherein cells of said plant produce an increased amount of α-keto-butyrate compared to that in cells of a corresponding, wild-type plant not comprising said introduced DNAs.

A plant, the genome of which comprises introduced DNAs encoding the following enzymes:
- a wild-type or deregulated aspartate kinase;
- homoserine dehydrogenase;
- a wild-type or deregulated threonine deaminase; and
- pyruvate oxidase;
- wherein each of said introduced DNAs is operatively linked to regulatory signals that cause expression of said introduced DNAs; and
- wherein cells of said plant produce an increased amount of propionyl-CoA compared to that in cells of a corresponding, wild-type plant not comprising said introduced DNAs.

A plant, the genome of which comprises introduced DNAs encoding the following enzymes:
- a wild-type or deregulated aspartate kinase;
- homoserine dehydrogenase;
- threonine synthase;
- a wild-type or deregulated threonine deaminase; and
- pyruvate oxidase;
- wherein each of said introduced DNAs is operatively linked to regulatory signals that cause expression of said introduced DNAs; and
- wherein cells of said plant produce an increased amount of propionyl-CoA compared to that in cells of a corresponding, wild-type plant not comprising said introduced DNAs.

A plant, the genome of which comprises introduced DNAs encoding the following enzymes:
- a wild-type or deregulated aspartate kinase;
- homoserine dehydrogenase;
- a wild-type or deregulated threonine deaminase;
- pyruvate oxidase; and
- an acyl-CoA synthetase;
- wherein each of said introduced DNAs is operatively linked to regulatory signals that cause expression of said introduced DNAs; and
- wherein cells of said plant produce an increased amount of propionyl-CoA compared to that in cells of a corresponding, wild-type plant not comprising said introduced DNAs.

A plant, the genome of which comprises introduced DNAs encoding the following enzymes:
- a wild-type or deregulated aspartate kinase;
- homoserine dehydrogenase;
- threonine synthase;
- a wild-type or deregulated threonine deaminase;
- pyruvate oxidase; and
- an acyl-CoA synthetase;
- wherein each of said introduced DNAs is operatively linked to regulatory signals that cause expression of said introduced DNAs; and
- wherein cells of said plant produce an increased amount of propionyl-CoA compared to that in cells of a corresponding, wild-type plant not comprising said introduced DNAs.

A plant, the genome of which comprises introduced DNAs encoding the following enzymes:
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;
- wherein each of said introduced DNAs is operatively linked to regulatory signals that cause expression of said introduced DNAs; and
- wherein cells of said plant produce an increased amount of propionyl-Co A compared to that in cells of a corresponding, wild-type plant not comprising said introduced DNAs.

A plant, the genome of which comprises introduced DNAs encoding the following enzymes:
- threonine synthase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;
- wherein each of said introduced DNAs is operatively linked to regulatory signals that cause expression of said introduced DNAs; and
- wherein cells of said plant produce an increased amount of propionyl-Co A compared to that in cells of a corresponding, wild-type plant not comprising said introduced DNAs.

A plant, the genome of which comprises introduced DNAs encoding the following enzymes:

a wild-type or deregulated aspartate kinase;

a wild-type or deregulated threonine deaminase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

threonine synthase;

a wild-type or deregulated threonine deaminase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase;

a wild-type or deregulated threonine deaminase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase;

threonine synthase;

a wild-type or deregulated threonine deaminase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated threonine deaminase;

pyruvate oxidase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

threonine synthase;

a wild-type or deregulated threonine deaminase;

pyruvate oxidase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated threonine deaminase;

pyruvate oxidase;

an acyl-CoA synthetase; and an α-ketoacid decarboxylase E1 subunit that exhibits improved binding and decarboxylating is activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

threonine synthase;

a wild-type or deregulated threonine deaminase;

pyruvate oxidase;

an acyl-CoA synthetase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase;

a wild-type or deregulated threonine deaminase;

pyruvate oxidase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated threonine deaminase;

a wild-type or deregulated aspartate kinase;

homoserine dehydrogenase;

pyruvate oxidase;

an acyl-CoA synthetase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated threonine deaminase;

a wild-type or deregulated aspartate kinase;

homoserine dehydrogenase;

threonine synthase;

pyruvate oxidase;

an acyl-CoA synthetase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

wherein each of said introduced DNAs is operatively linked to regulatory signals that cause expression of said introduced DNAs; and wherein cells of said plant produce an increased amount of propionyl-CoA compared to that in cells of a corresponding, wild-type plant not comprising said introduced DNAs.

A plant, the genome of which comprises introduced DNAs encoding the following enzymes:

a wild-type or deregulated aspartate kinase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-oA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

threonine synthase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

threonine synthase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxyvaleryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

threonine synthase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

threonine synthase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E 1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

threonine synthase;

a wild-type or deregulated threonine deaminase;

pyruvate oxidase;

an acyl-CoA synthetase;

an α-ketoacid decarboxylase E 1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

A plant, the genome of which comprises introduced DNAs encoding the following enzymes:

a wild-type or deregulated aspartate kinase;
homoserine dehydrogenase;
threonine synthase;
a wild-type or deregulated threonine deaminase;
pyruvate oxidase;
an acyl-CoA synthetase;
an α-ketoacid decarboxylase E1 subunit that exhibits improved binding and decarboxylating activities with oα-ketobutyrate compared with pyruvate decarboxylase E1 subunit naturally present in pyruvate dehydrogenase complex in said plant;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein each of said introduced DNAs is operatively linked to regulatory signals that cause expression of said introduced DNAs; and wherein cells of said plant produce P(3HB-co-3HV) copolymer.

Any of the foregoing plants, wherein each of said introduced DNAs is further operatively linked to a plastid transit peptide coding region capable of directing transport of said enzyme encoded thereby into a plastid.

A method of producing P(3HB-co-3HV)copolymer, comprising growing any of the foregoing plants, the genome of which comprises introduced DNAs encoding a β-ketothiolase, a β-ketoacyl-CoA reductase, and a polyhydroxyalkanoate synthase, and recovering said P(3HB-co-3HV) copolymer produced thereby.

The foregoing method, wherein said P(3HB-co-3HV) copolymer is recovered from leaves or seeds of said plant.

A plant cell containing P(3HB-co-3HV) copolymer.

A plant comprising cells containing P(3HB-co-3HV) copolymer.

Seeds of the foregoing plant.

The foregoing plant, wherein said cells are located in leaves or seeds of said plant.

A plant, the genome of which comprises introduced DNAs encoding the enzymes PhbA, PhbB, and PhbC;

wherein each of said introduced DNAs is operatively linked to a plastid transit peptide coding region capable of directing transport of said enzymes into a plastid, and regulatory signals that cause expression of said introduced DNAs in seeds of said plant; and wherein P(3HB) homopolymer is produced in seeds of said plant.

A method of producing P(3HB) homopolymer, comprising growing the foregoing plant, and recovering said P(3HB) homopolymer produced thereby.

The foregoing method, wherein said P(3HB) homopolymer is recovered from seeds of said plant.

A bacterium, the genome of which comprises introduced DNA encoding a wild-type or deregulated aspartate kinase;

wherein said introduced DNA is operatively linked to regulatory signals that cause expression of said introduced DNA; and wherein said bacterium produces an elevated amount of threonine compared to that in a corresponding wild-type bacterium not comprising said introduced DNA.

A bacterium, the genome of which comprises introduced DNAs encoding the following enzymes:

a wild-type or deregulated aspartate kinase; and
threonine synthase;

wherein said introduced DNAs are operatively linked to regulatory signals that cause expression of said introduced DNAs; and wherein said bacterium produces an elevated amount of threonine compared to that in a corresponding wild-type bacterium not comprising said introduced DNAs.

A bacterium, the genome of which comprises introduced DNAs encoding the following enzymes:

a wild-type or deregulated aspartate kinase; and
homoserine dehydrogenase;

wherein said introduced DNAs are operatively linked to regulatory signals that cause expression of said introduced DNAs; and wherein said bacterium produces an elevated amount of threonine compared to that in a corresponding wild-type bacterium not comprising said introduced DNAs.

A bacterium, the genome of which comprises introduced DNAs encoding the following enzymes:

a wild-type or deregulated aspartate kinase;
homoserine dehydrogenase; and
threonine synthase;

wherein said introduced DNAs are operatively linked to regulatory signals that cause expression of said introduced DNAs; and wherein said bacterium produces an elevated amount of threonine compared to that in a corresponding wild-type bacterium not comprising said introduced DNAs.

A bacterium, the genome of which comprises introduced DNAs encoding the following enzymes:

a wild-type or deregulated aspartate kinase; and a wild-type or deregulated threonine deaminase;

wherein said introduced DNAs are operatively linked to regulatory signals that cause expression of said introduced DNAs; and wherein said bacterium produces an elevated amount of α-keto-butyrate compared to that in a corresponding wild-type bacterium not comprising said introduced DNAs.

A bacterium, the genome of which comprises introduced DNAs encoding the following enzymes:

a wild-type or deregulated aspartate kinase;

threonine synthase; and a wild-type or deregulated threonine deaminase;

wherein said introduced DNAs are operatively linked to regulatory signals that cause expression of said introduced DNAs; and wherein said bacterium produces an elevated amount of α-keto-butyrate compared to that in a corresponding wild-type bacterium not comprising said introduced DNAs.

A bacterium, the genome of which comprises introduced DNAs encoding the following enzymes:

a wild-type or deregulated aspartate kinase;

homoserine dehydrogenase; and a wild-type or deregulated threonine deaminase;

wherein said introduced DNAs are operatively linked to regulatory signals that cause expression of said introduced DNAs; and wherein said bacterium produces an increased amount of α-keto-butyrate compared to that in a wild-type bacterium not comprising said introduced DNAs.

A bacterium, the genome of which comprises introduced DNAs encoding the following enzymes:

a wild-type or deregulated aspartate kinase;

homoserine dehydrogenase;

threonine synthase; and a wild-type or deregulated threonine deaminase;

wherein said introduced DNAs are operatively linked to regulatory signals that cause expression of said introduced DNAs; and wherein said bacterium produces an increased amount of α-keto-butyrate compared to that in a wild-type bacterium not comprising said introduced DNAs.

A bacterium, the genome of which comprises introduced DNAs encoding the following enzymes:

a wild-type or deregulated threonine deaminase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex of said bacterium;

wherein each of said introduced DNAs is operatively linked to regulatory signals that cause expression of said introduced DNAs; and wherein said bacterium produces an elevated amount of propionyl-CoA compared to that in a corresponding wild-type bacterium not comprising said introduced DNAs.

The foregoing bacterium, wherein said α-ketoacid decarboxylase E1 subunit that exhibits improved binding and decarboxylating activities with α-ketobutyrate is a branched chain α-ketoacid decarboxylase E1 subunit such as that from bovine kidney, *Pseudomonas putida*, or *Bacillus subtilis*.

A bacterium, the genome of which comprises introduced DNAs encoding:

a wild-type or deregulated threonine deaminase;

a pyruvate decarboxylase E1 subunit that exhibits improved binding and decarboxylating activities with α-ketobutyrate compared with pyruvate decarboxylase E1 subunit naturally present in pyruvate dehydrogenase complex in said bacterium; and a dihydrolipoyl transacylase E2 subunit exhibiting improved transacylase activity with α-ketobutyrate compared with dihydrolipoyl transacetylase E2 subunit naturally present in pyruvate dehydrogenase complex in said bacterium;

wherein said introduced DNAs are operatively linked to regulatory signals that cause expression of said introduced DNAs; and wherein said bacterium produces an elevated amount of propionyl-CoA compared to that in a corresponding wild-type bacterium not comprising said introduced DNAs.

The foregoing bacterium, wherein said α-ketoacid decarboxylase E1 subunit that exhibits improved binding and decarboxylating activities with α-ketobutyrate is a branched chain α-ketoacid decarboxylase E 1 subunit such as that from bovine kidney, *Pseudomonas putida*, or *Bacillus subtilis*, and said dihydrolipoyl transacylase E2 subunit exhibiting improved transacylase activity with α-ketobutyrate is one such as that from bovine kidney, *Pseudomonas putida*, or *Bacillus subtilis*.

A bacterium, the genome of which comprises introduced DNAs encoding the following enzymes:

a wild-type or deregulated threonine deaminase; and pyruvate oxidase;

wherein said introduced DNAs are operably linked to regulatory signals that cause expression of said introduced DNAs; and wherein said bacterium produces an elevated amount of propionyl-CoA compared that in a corresponding wild-type bacterium not comprising said introduced DNAs.

A bacterium, the genome of which comprises introduced DNAs encoding the following enzymes:

threonine synthase;

a wild-type or deregulated threonine deaminase; and pyruvate oxidase;

wherein said introduced DNAs are operably linked to regulatory signals that cause expression of said introduced DNAs; and wherein said bacterium produces an elevated amount of propionyl-CoA compared that in a corresponding wild-type bacterium not comprising said introduced DNAs.

The foregoing bacterium, wherein said pyruvate oxidase is encoded by *E. coli* poxB.

A bacterium, the genome of which comprises introduced DNAs encoding the following enzymes:

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

The foregoing bacterium, wherein said β-ketothiolase capable of condensing acetyl-CoA and propionyl-CoA to produce β-ketovaleryl-CoA is BktB.

The foregoing bacterium, wherein said β-ketoacyl-CoA reductase is acetoacetyl-CoA reductase.

The foregoing bacterium, wherein said polyhydroxyalkanoate synthase is obtainable from a microorganism selected from the group consisting of *Alcaligenes eutrophus, Alcaligenes faecalis,* Aphanothece sp., *Azotobacter vinelandii, Bacillus cereus, Bacillus megaterium, Beijerinkia indica, Derxia gummosa,* Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum,* and *Thiocapsa pfennigii.*

A bacterium, the genome of which comprises introduced DNA encoding a wild-type or deregulated threonine deaminase;

wherein said introduced DNA is operatively linked to regulatory signals that cause expression of said introduced DNA; and wherein said bacterium produces an increased amount of α-keto-butyrate compared to that in a corresponding wild-type bacterium not comprising said introduced DNA.

A bacterium, the genome of which comprises introduced DNAs encoding the following enzymes:

threonine synthase; and a wild-type or deregulated threonine deaminase;

wherein said introduced DNAs are operatively linked to regulatory signals that cause expression of said introduced DNAs; and wherein said bacterium produces an increased amount of α-keto-butyrate compared to that in a corresponding wild-type bacterium not comprising said introduced DNAs.

A bacterium, the genome of which comprises introduced DNAs encoding the following enzymes:

a wild-type or deregulated aspartate kinase;

homoserine dehydrogenase;

a wild-type or deregulated threonine dearninase; and pyruvate oxidase;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- threonine synthase;
- a wild-type or deregulated threonine deaminase; and
- pyruvate oxidase;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- a wild-type or deregulated threonine deaminase;
- pyruvate oxidase; and
- an acyl-CoA synthetase;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- threonine synthase;
- a wild-type or deregulated threonine deaminase;
- pyruvate oxidase; and
- an acyl-CoA synthetase;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-Co A compared to that in a corresponding, wild-type bacterium not comprising said introduced DNAs.

A bacterium, the genome of which comprises introduced DNAs encoding the following enzymes:
- threonine synthase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-Co A compared to that in a corresponding, wild-type bacterium not comprising said introduced DNAs.

A bacterium, the genome of which comprises introduced DNAs encoding the following enzymes:
- a wild-type or deregulated aspartate kinase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- threonine synthase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- threonine synthase;
- a wild-type or deregulated threonine deaminase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated threonine deaminase;
- pyruvate oxidase; and
- an α-ketoacid decarboxylase E1 subunit that exhibits improved binding and decarboxylating activities with oα-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- threonine synthase;
- a wild-type or deregulated threonine deaminase;
- pyruvate oxidase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated threonine deaminase;
- pyruvate oxidase;
- an acyl-CoA synthetase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- threonine synthase;
- a wild-type or deregulated threonine deaminase;
- pyruvate oxidase;
- an acyl-CoA synthetase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- a wild-type or deregulated threonine deaminase;
- pyruvate oxidase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;
- threonine synthase;
- a wild-type or deregulated threonine dearninase;
- pyruvate oxidase; and
- an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;
- wherein said introduced DNAs are operatively linked to regulatory signals that cause expression of said introduced DNAs; and
- wherein said bacterium produces an increased amount of propionyl-CoA compared to that in a corresponding, wild-type bacterium not comprising said introduced DNAs.

A bacterium, the genome of which comprises introduced DNAs encoding the following enzymes:
- a wild-type or deregulated aspartate kinase;
- homoserine dehydrogenase;

a wild-type or deregulated threonine deaminase;

pyruvate oxidase;

an acyl-CoA synthetase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an acyl-CoA synthetase; and an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

wherein said introduced DNAs are operatively linked to regulatory signals that cause expression of said introduced DNAs; and wherein said bacterium produces an increased amount of propionyl-CoA compared to that in a corresponding, wild-type bacterium not comprising said introduced DNAs.

A bacterium, the genome of which comprises introduced DNAs encoding the following enzymes:

a wild-type or deregulated aspartate kinase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

threonine synthase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type, partially, or totally lysine feedback inhibition insensitive aspartate kinase;

homoserine dehydrogenase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type, partially, or totally lysine feedback inhibition insensitive aspartate kinase;

homoserine dehydrogenase;

threonine synthase;

a wild-type or deregulated threonine deaminase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and p-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and p-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an acyl-CoA synthetase;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryt-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in is pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

threonine synthase;

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A bacterium, the genome of which comprises introduced DNAs encoding the following enzymes:

a wild-type or deregulated aspartate kinase;

homoserine dehydrogenase;

threonine synthase;

a wild-type or deregulated threonine deaminase;

pyruvate oxidase;

an acyl-CoA synthetase;

an α-ketoacid decarboxylase E1 subunit that exhibits improved binding and decarboxylating activities with α-ketobutyrate compared with pyruvate decarboxylase E1 subunit naturally present in pyruvate dehydrogenase complex in said bacterium;

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

A method of producing P(3HB-co-3HV) copolymer, comprising growing any of the foregoing bacteria, the genome of which comprises introduced DNAs encoding a β-ketothiolase, a β-ketoacyl-CoA reductase, and a polyhydroxy-alkanoate synthase, and recovering said P(3HB-co-3HV)copolymer produced thereby.

A bacterium, the genome of which comprises introduced DNAs encoding the following enzymes:

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer.

The foregoing bacterium can be one that overproduces threonine. The genome thereof can further comprise, in addition to introduced DNAs encoding the enzymes listed above, introduced DNA encoding a wild-type or deregulated threonine deaminase. Alternatively, the foregoing bacterium can be one that produces propionate or propionyl-CoA at levels useful for producing P(3HB-co-3HV) copolymer.

A method of producing P(3HB-co-3HV) copolymer, comprising:

culturing any of the four foregoing mentioned bacteria under conditions and for a time conducive to the formation of P(3HB-co-3HV) copolymer; and recovering said P(3HB-co-3HV) copolymer produced thereby.

A bacterium, the genome of which comprises introduced DNAs encoding the following enzymes:

a β-ketothiolase capable of condensing two molecules of acetyl-CoA to produce acetoacetyl-CoA and a β-ketothiolase capable of condensing acetyl-CoA and propionyl-CoA to produce β-ketovaleryl-CoA; or a β-ketothiolase capable of condensing two molecules of acetyl-CoA to produce acetoacetyl-CoA, and capable of condensing acetyl-CoA and propionyl-CoA to produce β-ketovaleryl-CoA;

a β-ketoacyl-CoA reductase capable of reducing acetoacetyl-CoA and β-ketovaleryl-CoA to produce β-hydroxybutyryl-CoA and β-hydroxy-valeryl-CoA, respectively; and a polyhydroxyalkanoate synthase capable of incorporating β-hydroxybutyryl-CoA and β-hydroxyvaleryl-CoA into P(3HB-co-3HV) copolymer;

wherein said introduced DNAs are operatively linked to regulatory signals that cause expression of said introduced DNAs; and wherein said bacterium produces P(3HB-co-3HV) copolymer when grown on a medium comprising propionic acid.

A method of producing P(3HB-co-3HV) copolymer, comprising:

culturing the foregoing bacterium on a medium comprising propionic acid under conditions and for a time conducive to the formation of P(3HB-co-3HV) copolymer, and recovering said P(3HB-co-3HV) copolymer produced thereby.

A bacterial cell containing P(3HB-co-3HV) copolymer, wherein said P(3HB-co-3HV) copolymer is produced within said bacterial cell as a result of expression of at least one DNA sequence introduced therein that encodes an enzyme necessary for P(3HB-co-3HV) copolymer synthesis.

The foregoing bacterial cell, wherein said at least one DNA sequence is selected from the group consisting of a DNA sequence encoding a β-keto-thiolase capable of condensing two molecules of acetyl-CoA to produce acetoacetyl-Co-A, a DNA sequence encoding a β-ketothiolase capable of condensing acetyl-CoA and propionyl-CoA to produce β-ketovaleryl-CoA, a DNA sequence encoding a β-ketoacyl-CoA reductase, a DNA sequence encoding a polyhydroxyalkanoate synthase capable of incorporating β-hydroxybutyryl-CoA and β-hydroxyvaleryl-CoA into P(3HB-co-3HV) copolymer, and combinations thereof.

The foregoing bacterial cell, further comprising a DNA sequence introduced therein that encodes a wild-type or deregulated threonine deaminase, wherein said DNA sequence encoding said wild-type or deregulated threonine deaminase is expressed.

A method for transforming canola, comprising:

(a) preparing a stem explant from a canola plant by:
  (i) removing leaves and buds along the stem and removing 4–5 inches of said stem below the flower buds; and
  (ii) cutting said 4–5 inches of stem into segments;
(b) inserting DNA to be introduced into said explant of step (a) by inoculating said explant with a disarmed *Agrobacterium tumefaciens* vector containing said DNA;
(c) culturing said explant of step (b) in the basal-side down orientation;
(d) selecting transformed explant tissue; and
(e) regenerating a differentiated transformed plant from said transformed explant tissue of step (d).

A method for transforming soybean, comprising:

(a) preparing a cotyledon explant from a soybean seedling by:
  (i) incubating said seedling at about 0° C. to about 10° C. for at least 24 hours;
  (ii) removing the hypocotyl region by cutting in the region of from about 0.2 to about 1.5 cm below the cotyledonary node;
  (ii) splitting and completely separating the remaining attached hypocotyl segment, also thereby separating the two cotyledons;
  (iii) removing the epicotyl from the cotyledon to which it remains attached; and (iv) wounding the cotyledon in the region of said axillary bud;

(b) inserting DNA to be introduced into said explant of step (a) by inoculating at least the region adjacent to the axillary bud of the explant with a disarmed *Agrobacterium tumefaciens* vector containing said DNA;

(c) selecting transformed explant tissue; and (d) regenerating a differentiated transformed plant from said transformed explant tissue of step (c).

A soybean explant prepared by steps (a)(i)–(a)(iv) of the preceding method.

Soybean tissue prepared from a seedling cotyledon pair containing an epicotyl, axillary buds, and hypocotyl tissue, comprising a single cotyledon containing an axillary bud and associated hypocotyl segment extending from about 0.2 to about 1.5 cm below the cotyledonary node;

wherein said associated hypocotyl segment is completely separated from its adjacent hypocotyl segment attached to the remaining cotyledon, thus separating said cotyledons;

wherein said epicotyl has been removed from the cotyledon to which it is attached;

wherein the cotyledon is wounded in the region of said axillary bud; and wherein said seedling has been incubated at a temperature of from about 0° C. to about 10° C. for at least about 24 hours prior to preparing said soybean tissue.

The present invention provides a novel means towards obtaining biosynthetic hydroxyalkanoate polymers. In a preferred embodiment, the polymers have a single mode molecular weight distribution. As used herein, a single mode molecular weight distribution refers to a plot of molecular weight (x-axis) against population (y-axis), resulting in a single peak. Multiple mode molecular weight distributions display two or more peaks in such a plot. The plot is first 'smoothed' by generally any mathematically valid model, and preferably by the smoothing function described in "Exploratory Data Analysis" (Tukey, J. W. Addison-Wesley publishers, Reading, Mass., 1977, pp 205–235). The three highest peak heights are selected, and their peak heights added together to form a peak sum. In order for a plot to represent a single mode molecular weight distribution, the highest peak height must comprise at least about 80% of the peak sum. Molecular weight may be determined by methods such as size exclusion chromatography or gel permeation chromatography. In a further preferred embodiment, the polymers have a small molecular weight distribution. As used herein, molecular weight distribution, also referred to as polydispersity, is calculated by dividing the weight average molecular weight by the number average molecular weight.

In a preferred embodiment, a plant extract will contain a polyhydroxyalkanoate polymer wherein the polyhydroxyalkanoate polymer was produced by a plant, and where the polyhydroxyalkanoate polymer has a single mode molecular weight distribution. As used herein, a plant extract refers to materials prior to chromatographic separation. The extract may be a plant lysate, or the materials dissolved from contacting the plant or plant materials with a suitable solvent including, but not limited to alcohol or chloroform. Lysates may be prepared by a variety of methods including, but not limited to mechanical damage, chemical treatment, or enzymatic digestion. The polyhydroxyalkanoate polymer preferably has a molecular weight distribution of between about 1 and about 5, preferably between about 1.5 and about 4.5, more preferably between about 2 and about 4, and most preferably about 2.1 or about 2.5. The polyhydroxyalkanoate polymer may be a homopolymer or a copolymer. The polyhydroxyalkanoate polymer may generally be any polyhydroxyalkanoate polymer compatible with the inventive processes, and more preferably a polymer of 3-hydroxybutyrate, 3-hydroxyhexanoate, 3-hydroxyoctanoate, 3-hydroxydecanoate, 3-hydroxydodecanoate, 3-hydroxytetradecanoate, 3-hydroxyhexadecanoate, 3-hydroxyoctadecanoate, 3-hydroxyeicosanoate, 3-hydroxydocosanoate, or copolymers thereof. In more preferred embodiments, the homopolymer is poly(3-hydroxybutyrate) or poly(4-hydroxybutyrate), and the copolymer is poly(3-hydroxybutyrate-co-3-hydroxyvalerate), poly(3-hydroxybutyrate-co-4-hydroxybutyrate), poly(3-hydroxybutyrate-co-3-hydroxyhexanoate), poly(4-hydroxybutyrate-co-3-hydroxyhexanoate), or poly(3-hydroxybutyrate-co-4-hydroxybutyrate-co-3-hydroxyhexanoate). The plant in which the polyhydroxyalkanoate polymer is biosynthesized is generally any plant suitable for the biosynthesis of polyhydroxyalkanoate polymers, and more preferably is tobacco, wheat, potato, Arabidopsis, corn, soybean, canola, oil seed rape, sunflower, flax, peanut, sugarcane, swtichgrass, or alfalfa. The number average molecular weight of the polyhydroxyalkanoate polymer is preferably greater than about 100,000, more preferably greater than about 300,000, and most preferably greater than about 500,000.

The invention further provides methods for the preparation of polyhydroxyalkanoate polymers having a single mode molecular weight distribution. A preferred embodiment comprises the steps of (a) inserting into a plant cell nucleic acid molecules comprising a polyhydroxyalkanoate synthesis pathway, preferably comprising a β-ketoacyl reductase gene, a β-ketothiolase gene, and a polyhydroxyalkanoate synthase gene; (b) isolating a transformed plant cell; (c) regenerating the transformed plant cell to form a transformed plant; (d) selecting a transformed plant which produces a polyhydroxyalkanoate polymer having a single mode molecular weight distribution; and(e) isolating the polyhydroxyalkanoate polymer. The β-ketoacyl reductase, β-ketothiolase, and polyhydroxyalkanoate synthase genes may generally be of any source suitable for participation in the inventive processes, more preferably the genes are *Alcaligenes eutrophus, Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum*, or *Thiocapsa pfennigii* genes, and most preferably are *Alcaligenes eutrophus* genes. The polyhydroxyalkanoate polymer preferably has a molecular weight distribution of between about 1 and about 5, preferably between about 1.5 and about 4.5, more preferably between about 2 and about 4, and most preferably about 2.1 or about 2.5. The polyhydroxyalkanoate polymer may be a homopolymer or a copolymer. The polyhydroxyalkanoate polymer may generally be any polyhydroxyalkanoate polymer compatible with the inventive processes, and more preferably a polymer of 3-hydroxybutyrate, 3-hydroxyhexanoate, 3-hydroxyoctanoate, 3-hydroxydecanoate, 3-hydroxydodecanoate, 3-hydroxytetradecanoate, 3-hydroxyhexadecanoate, 3-hydroxyoctadecanoate, 3-hydroxyeicosanoate, 3-hydroxydocosanoate, or copolymers thereof. In more preferred embodiments, the homopolymer is poly(3-hydroxybutyrate) or poly(4-hydroxybutyrate), and the copolymer is poly(3-hydroxybutyrate-co-3-hydroxyvalerate), poly(3-hydroxybutyrate-co-4-hydroxybutyrate), poly(3-hydroxybutyrate-co-3-hydroxyhexanoate), poly(4-hydroxybutyrate-co-3-hydroxyhexanoate), or poly(3-hydroxybutyrate-co-4-hydroxybutyrate-co-3-hydroxyhexanoate). The plant in which the polyhydroxyalkanoate polymer is biosynthesized is generally any plant suitable for the biosynthesis of polyhydroxyalkanoate polymers, and more preferably is tobacco, wheat, potato, Arabidopsis, corn, soybean, canola, oil seed rape, sunflower, flax, peanut, sugarcane, swtichgrass, or alfalfa. The number average molecular weight of the polyhydroxyalkanoate polymer is preferably greater than about 100,000, more preferably greater than about 300,000, and most preferably greater than about 500,000. The transformed plant cells and plants may further comprise nucleic acid molecules having genes that allow the plant to synthesize additional polyhydroxyalkanoate precursors. In a preferred embodiment, the nucleic acid molecules further comprise succinyl-CoA:acetyl-CoA CoA transferase, succinate semialdehyde dehydrogenase, 4-hydroxybutyrate dehydrogenase, and hydroxybutyryl-CoA:acetyl-CoA CoA transferase genes. The inventive methods may be further extended by including a step of generating a homozygous daughter plant derived from the transformed plant. Conventional methods such as growing daughter plants from seeds, and cross-breeding may be used to generate such a homozygous daughter plant. The transformed plant may be analyzed to determine the copy number of the polyhydroxyalkanoate synthase gene. It is preferable that the synthase gene be present in a low copy number, more preferably less than five, and most preferably present at a single copy. Copy number may be determined by any method known to those of skill in the art, and preferably by Southern blotting.

The invention further provides methods for selecting a transformed plant cell or plant that is particularly suitable for the production of a polyhydroxyalkanoate polymer having a single mode molecular weight distribution. A preferred embodiment comprises the steps of (a) obtaining transformed plant cells or transformed plants, (b) analyzing the plant cells or plants for the presence of a polyhydroxyalkanoate synthase gene, (c) determining the copy number of the polyhydroxyalkanoate synthase gene, and(d) selecting a transformed plant cell or transformed plant having a single copy of the polyhydroxyalkanoate synthase gene. Copy number may be determined by any method known to those of skill in the art, and preferably by Southern blotting.

Further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

Conventional methods of gene isolation, molecular cloning, vector construction, etc., are well known in the art and are summarized in Sambrook et al., 1989, and Ausubel et al., 1989. One skilled in the art can readily reproduce the plasmids vectors described above without undue experimentation employing these methods in conjunction with the cloning information provided by the figures attached hereto. The various DNA sequences, fragments, etc., necessary for this purpose can be readily obtained as components of commercially available plasmids, or are otherwise well known in the art and publicly available.

The following detailed description of the invention is provided to aid those skilled in the art in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The references cited herein evidence the level of skill in the art to which the present invention pertains. The contents of each of these references, including the references cited therein, are herein incorporated by reference in their entirety.

The following Examples describe a variety of different methods for enhancing the levels of threonine, α-ketobutyrate, and propionyl-CoA, the latter being a direct precursor substrate in the synthesis of P(3HB-co-3HV) in bacteria and plants, and for producing PHA copolymers of differing C4/C5 compositions from various carbon sources.

DEFINITIONS

The following definitions are provided in order to aid those skilled in the art in understanding the detailed description of the present invention.

"β-ketoacyl-CoA reductase" refers to a β-ketoacyl-CoA reducing enzyme that can convert a β-ketoacyl-CoA substrate to its corresponding β-hydroxyacyl-CoA product using, for example, NADH or NADPH as the reducing cosubstrate. An example is the PhbB acetoacetyl-CoA reductase of A. eutrophus.

"β-ketothiolase" refers to an enzyme that catalyzes the thiolytic cleavage of a β-ketoacyl-CoA, requiring free CoA, to form two acyl-CoA molecules. However, the term "β-ketothiolase" as used herein also refers to enzymes that catalyze the condensation of two acyl-CoA molecules to form β-ketoacyl-CoA and free CoA, i.e., the reverse of the thiolytic cleavage reaction.

"CoA" refers to coenzyme A.

"C-terminal region" refers to the region of a peptide, polypeptide, or protein chain from the middle thereof to the end that carries the amino acid having a free a carboxyl group.

"Deregulated enzyme" refers to an enzyme that has been modified, for example by mutagenesis, wherein the extent of feedback inhibition of the catalytic activity of the enzyme by a metabolite is reduced such that the enzyme exhibits enhanced activity in the presence of said metabolite compared to the unmodified enzyme. Some organisms possess deregulated forms of such enzymes as the naturally occuring, wild-type form.

The term "encoding DNA" refers to chromosomal DNA, plasmid DNA, cDNA, or synthetic DNA which codes on expression for any of the enzymes discussed herein.

The term "genome" as it applies to bacteria encompasses both the chromosome and plasmids within a bacterial host cell. Encoding DNAs of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally-integrated or organelle-localized.

The terms "microbe" or "microorganism" refer to algae, bacteria, fungi, and protozoa.

The term "mutein" refers to a mutant form of a peptide, polypeptide, or protein.

"N-terminal region" refers to the region of a peptide, polypeptide, or protein chain from the amino acid having a free a amino group to the middle of the chain.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These is organelles are self-replicating, and contain what is commonly referred to as the "chloroplast genome," a circular DNA molecule that ranges in size from about 120 to about 217 kb, depending upon the plant species, and which usually contains an inverted repeat region (Fosket, 1994).

The term "polyhydroxyalkanoate (PHA) synthase" refers to enzymes that convert β-hydroxyacyl-CoAs to polyhydroxyalkanoates and free CoA.

The term "u" refers to an enzyme unit. One unit catalyzes the production of one μmole of product per minute.

EXAMPLE 1

Figure 3:
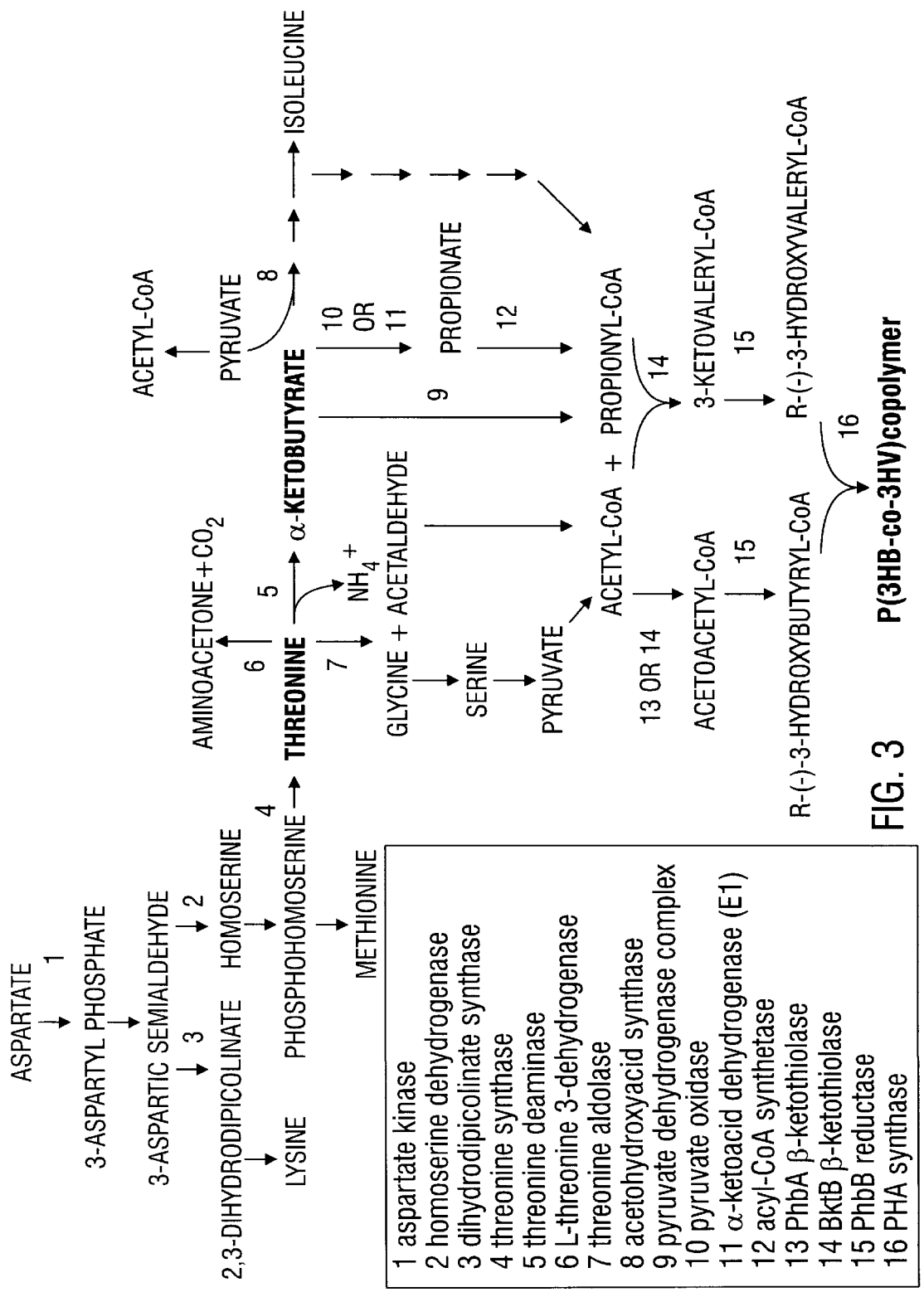
FIG. 3 summarizes the pathways discussed herein that are involved in the production of P(3HB-co-3HV) copolymer.

Increased Production of Amino Acids in Bacterial and Plant Cells Via Modification of the Activity of Aspartate Kinase, Homoserine Dehydrogenase, and Threonine Synthase Biosynthesis of the aspartate family of amino acids in plants occurs in the plastids (Bryan, 1980). FIG. 3 shows the enzymatic steps involved in the biosynthesis of P(3HB-co-3HV) copolymer from L-threonine via α-keto-butyrate. Both acetyl-CoA and propionyl-CoA are precursor substrates in the synthesis of P(3HB-co-3HV) as shown in this figure.

The involvement of L-threonine in the formation of α-ketobutyrate is described in detail below in Examples 2, 3, and 4. The present example describes methods for increasing the available pools of L-threonine in bacterial and plant cells for P(3HB-co-3HV) copolymer biosynthesis.

Overexpression of a threonine or lysine deregulated aspartate kinase (AK), the enzyme that catalyzes the first step in the biosynthesis of threonine, lysine, and methionine (FIG. 3), results in an increase in the intracellular levels of free L-threonine in the leaf by 55% (Shaul and Galili, 1992a), and in the seed by 15-fold (Karchi et al., 1993).

A downstream enzyme in the aspartate pathway is dihydrodipicolinate synthase (DHPS), which catalyzes the first committed step in lysine synthesis (FIG. 3). Plants that overexpress a deregulated form of DHPS exhibit a 15-fold increase in free lysine (Shaul and Galili, 1992b). Plants expressing deregulated forms of both AK and DHPS exhibit a dramatic increase in free lysine, but lower levels of free threonine (Shaul and Galili, 1993). Recently Falco et al., (1995) demonstrated increased lysine in seeds of canola by 45% and in soybean by 33% by overexpressing deregulated aspartate kinase and dihydrodipicolinate synthase. Since both the AK and DHPS enzymes were overexpressed relative to the wild-type enzymes, the biosynthetic pathway favored the formation of lysine over threonine (FIG. 3). In all cases, the amount of available aspartate was not limiting in the formation of the end products.

In accordance with the present invention, threonine is an important metabolite in PHA biosynthesis as shown in FIG. 3. Overexpression of either a wild-type or deregulated aspartate kinase will increase the available pools of free threonine in the plastids. As discussed in Examples 2–4, below, overexpression of a deregulated threonine deaminase in bacterial or plant cells will greatly enhance threonine turnover to α-ketobutyrate. A possible effect of this enhanced threonine turnover may be depletion of other aspartate family amino acids (see FIG. 3). Increasing the level of aspartate kinase can ameliorate this possible negative effect by increasing the pools of metabolic precursors involved in the biosynthesis of lysine, threonine, and methionine. This will result in enhancement of the free pools of lysine and methionine in the cell (i.e., in the plastids), thereby preventing starvation for lysine and/or methionine in the event that overexpression of threonine deaminase causes such starvation. In addition to aspartate kinase (AK), homoserine dehydrogenase (HSD) and threonine synthase can be used to increase further the levels of free threonine (see FIG. 3).

Deregulated aspartate kinases useful in the present invention can possess a level of threonine and/or lysine insensitivity such that at 0.1 mM threonine and/or 0.1 mM lysine and the Km concentration of aspartate, the enzymes exhibit ≧10% activity relative to assay conditions in which threonine and/or lysine is absent. Deregulated homoserine dehydrogenases useful in the present invention preferably possess a level of threonine insensitivity such that at 0.1 mM threonine and the Km concentration of aspartate semialdehyde, the enzymes exhibit ≧10% activity relative to assay conditions in which threonine is absent. The Vmax values for the aspartate kinase and homoserine dehydrogenase enzymes can fall within the range of 0.1–100 times that of their corresponding wild-type enzymes. The Km values for the aspartate kinase and homoserine dehydrogenase enzymes can fall within the range of 0.01–10 times that of their corresponding wild-type enzymes.

Threonine synthase, the enzyme responsible for converting phosphohomoserine to threonine, has been shown to enhance the level of threonine about 10-fold over the endogenous level when overexpressed in *Methylobacillus glycogenes* (Motoyama et al., 1994). In addition, *E. coli* threonine synthase overexpressed in tobacco cell culture resulted in a 10-fold enhanced level of threonine from is a six-fold increase in total threonine synthase activity (Muhitch, 1995). It is apparent from these results that overexpressed levels of threonine synthase in plants or other organisms will have the effect of increasing threonine levels therein. This can be employed in the present invention to insure an enhanced supply of threonine for α-ketobutyrate and propionyl-CoA production, the latter by the action of the next enzyme, threonine deaminase (described in Examples 2, 3, 4.). In conjunction with the PHA biosynthetic enzymes described herein, threonine synthase can enhance the formation of P(3HB-co-3HV) copolymer.

EXAMPLE 2

Increased Production of α-Ketobutyrate From L-Threonine Via Modified *E. coli* Biosynthetic Threonine Deaminases L-threonine can be degraded by several metabolic routes (FIG. 3). Threonine aldolase (E.C. 4.1.2.5), a pyridoxal phosphate-containing enzyme, catalyzes threonine degradation to produce glycine and acetaldehyde, both of which can be metabolized to acetyl-CoA (Marcus and Dekker, 1993). Acetyl-CoA is the precursor of the C4 monomer in PHB (FIG. 1). L-threonine 3-dehydrogenase (E.C. 1.1.1.103) converts threonine into aminoacetone and $CO_2$ (Boylan and Dekker, 1981). Alternatively, L-threonine can be converted to α-ketobutyrate by threonine deaminase (also designated threonine dehydratase, E.C. 4.2.1.16), as shown in FIG. 3. α-ketobutyrate is a direct metabolic precursor of propionyl-CoA (FIG. 3). There is also competition for α-ketobutyrate in isoleucine biosynthesis (FIG. 3), and in transamination to produce 2-aminobutyrate (Shaner and Singh, 1993).

Biodegradative Threonine Deaminase

Threonine deaminase exists in two forms. One form is a biodegradative enzyme, encoded by, for example, the tdcB gene of E. coli. Biodegradative threonine deaminase permits threonine to be used as a carbon source. The structural gene for this enzyme has been isolated from E. coli K-12 (Goss and Datta, 1985), and the nucleotide sequence has been determined (Datta et. al., 1987). The biodegradative form of threonine deaminase is allosterically activated by high levels of AMP (Shizuta and Hayashi, 1976), and is inactivated by glucose, pyruvate, and other metabolites (Feldman and Datta, 1975). Biodegradative threonine deaminase is not feedback-inhibited by isoleucine. The $K_m$ of E. coli biodegradative threonine deaminase for threonine has been determined to be 11 mM in the presence of activator (10 mM AMP) and 91 mM in its absence (Shizuta and Tokushige, 1971). The $V_{max}$ for the enzyme decreases by a factor of six in the absence of activators (Shizuta and Tokushige, 1971). Due to their requirement for activation by AMP to exhibit optimal activity in vivo, most degradative threonine deaminases may not be optimal for purposes of the present invention.

Biosynthetic Threonine Deaminase

Another form of threonine deaminase is a biosynthetic enzyme that catalyzes the committed step in isoleucine biosynthesis (FIG. 3). In E. coli, this enzyme is encoded by the ilvA gene. It has recently been reported (Colón et. al., 1995) that overexpression of the biosynthetic threonine deaminase from C. glutamicum in C. lactofermentum leads to an increase in the amount of isoleucine produced in the latter. In most cases reported, the goal of utilizing an overexpressed threonine deaminase was to increase the available pools of the essential amino acid isoleucine.

Biosynthetic threonine deaminase was the first enzyme reported to be feedback inhibited by the endproduct of its biosynthetic pathway (i.e., isoleucine), and served as a model for the development of the concept of allosteric regulation (Changeux, 1961; Monod et. al., 1963). Biosynthetic threonine deaminase is strongly inhibited by isoleucine, and may not be optimal for producing enhanced levels of α-ketobutyrate in its natural form, even when overexpressed in recombinant systems. The results reported in Table 3, infra, support this conclusion. These results are discussed in greater detail in the section entitled "Biochemical Analysis of Wild-type and Mutant E. coli Threonine Deaminases", below.

In addition to being inhibited by isoleucine, biosynthetic threonine deaminase exhibits kinetic positive cooperativity. This results in much slower substrate turnover at low concentrations of threonine as compared to an enzyme that behaves in a normal Michaelis-Menten manner (also discussed in detail in the section entitled "Biochemical Analysis of Wild-type and Mutant E. coli Threonine Deaminases", below). This too is an undesirable property for a threonine deaminase employed to produce high levels of α-ketobutyrate.

Isoleucine Deregulated Mutants of Biosynthetic Threonine Deaminase

Isoleucine-deregulated mutants of biosynthetic threonine deaminase have been described in the literature in both bacteria and plants. One mutant, isolated from S. typhimurium, is referred to as ilvA219 (LaRossa et. al., 1987). The ilvA219 mutation results from a change in amino acid 447 from leucine (L) to phenylalanine (F). Another isoleucine-deregulated mutant of biosynthetic threonine deaminase, identified in E. coli, is referred to as ilvA466 (Taillon et al., 1988). The ilvA466 mutation results from a change in amino acid 481 from leucine (L) to phenylalanine (F). A third isoleucine-deregulated mutant of threonine deaminase has been described in C. glutamicum, and results from a change in amino acid 323 from valine (V) to alanine (A) (Möckel et al., 1994).

There have been two published reports of isoleucine-deregulated threonine deaminases in plants (Strauss et al., 1985; Mourad and King, 1995). In neither case was the mutation in the threonine deaminase identified.

Cloning and Expression of the Wild-type E. coli Biosynthetic Threonine Deaminase Gene Conventional molecular biological techniques for routine cloning, transformation, expression, etc., are well known to those of ordinary skill in the art and are described in detail in Sambrook et al., 1989 and Ausubel et al., 1989.

The nucleotide sequence of the wild-type E. coli ilvA threonine deaminase gene is available in the Genbank database (accession number K03503), and has also been published by Lawther et al. (1987). This sequence is shown in SEQ ID NO:1.

In order to produce various isoleucine-deregulated mutant forms of E. coli threonine deaminase, the encoding genomic DNA was first isolated from E. coli DH5α. Primers having the sequences shown in SEQ ID NO:2 and SEQ ID NO:3, respectively, were synthesized for use in the polymerase chain reaction (PCR) to amplify the gene encoding E. coli biosynthetic threonine deaminase:

SEQ ID NO:2
TTTTTGGATCCGATATCTTAACCCGC-CAAAAAGAACCTGAACGCCG

SEQ ID NO:3
TTTTTGGATCCATGGCTGACTCGCAAC-CCCTGTCCGG

Figure 4:
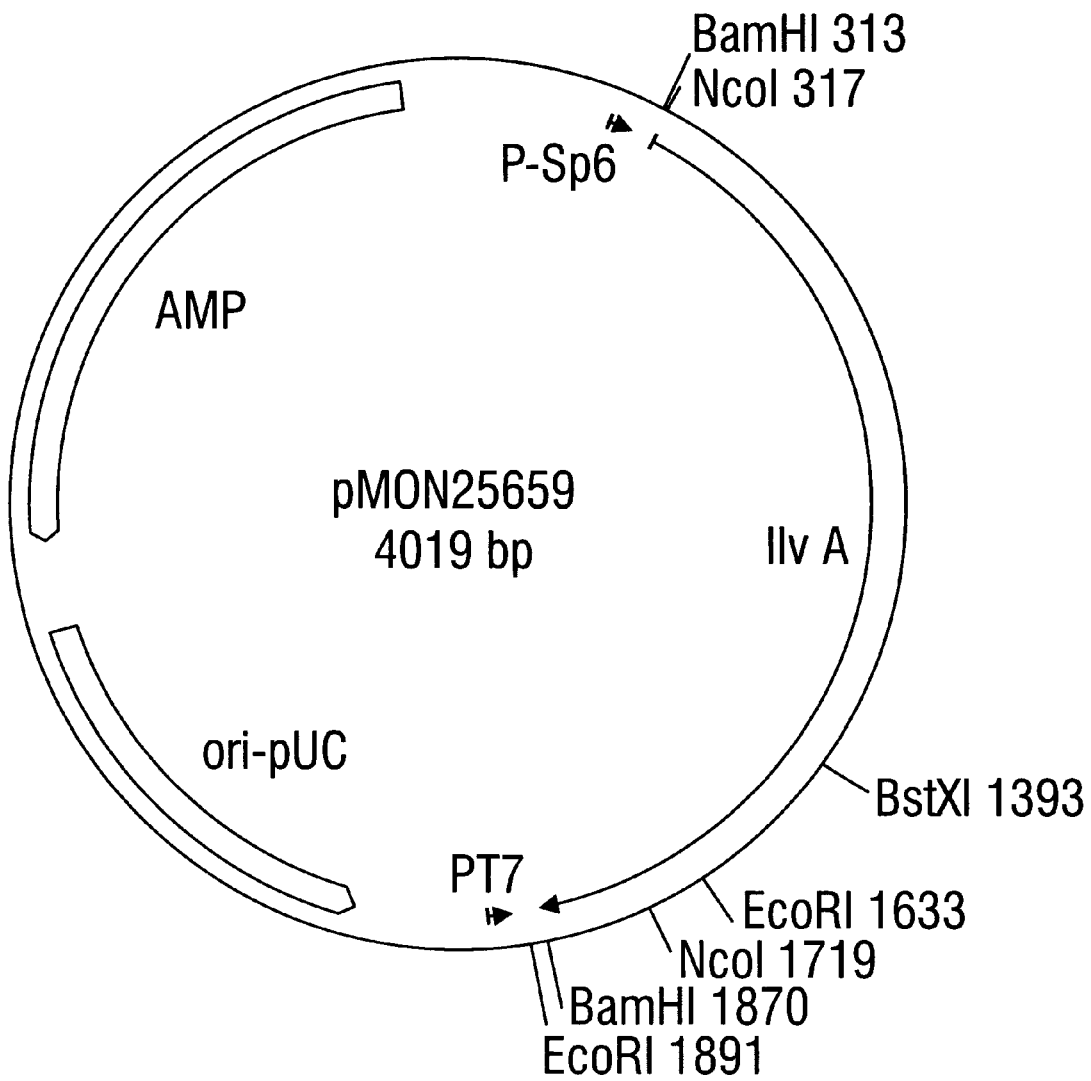
FIG. 4 shows the structure of pMON25659. pMON25659 contains the wild-type E. coli biosynthetic threonine deaminase (ilvA) gene derived by PCR. The nucleotide sequence of the wild-type biosynthetic threonine deaminase gene is shown in SEQ ID NO: 1.
Figure 5:
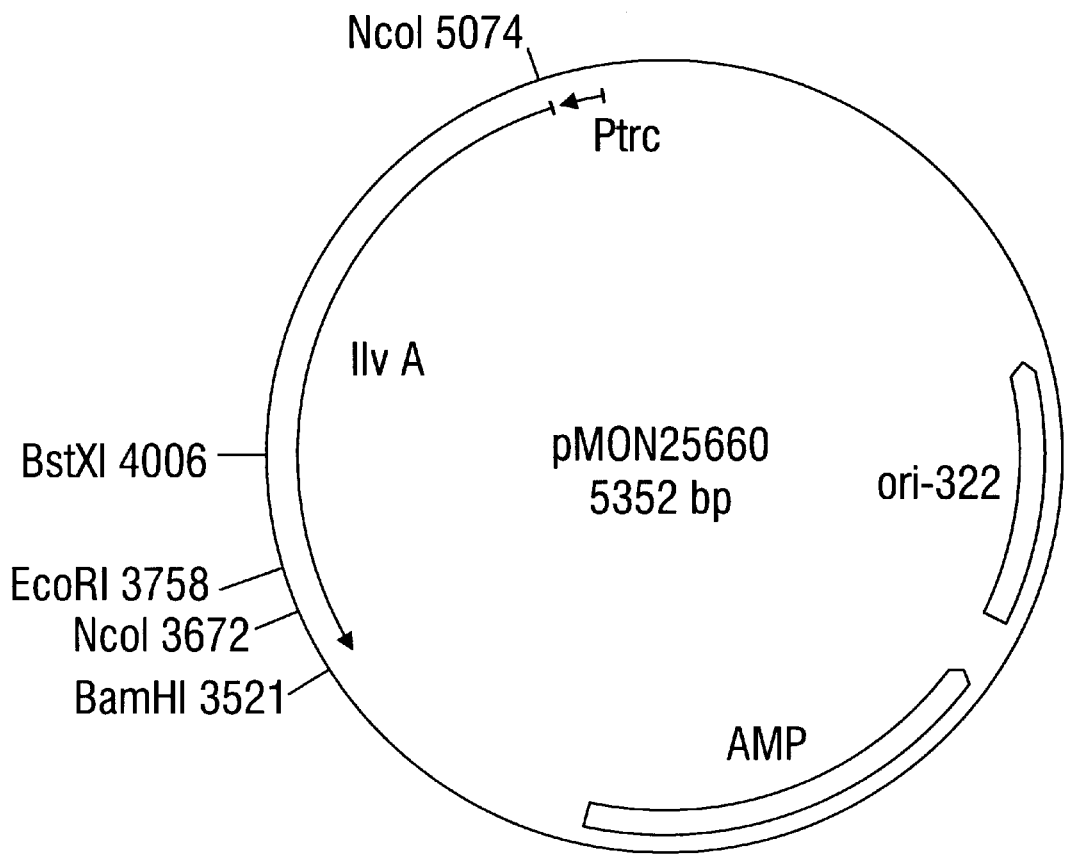
FIG. 5 shows the structure of pMON25660. pMON25660 was used for the overexpression of the wild-type biosynthetic threonine deaminase (IlvA) from the ptrc promoter in E. coli.

The 1,573 base pair PCR fragment thus obtained was subcloned as a BamHI restriction fragment into BamHI-digested plasmid pSP72 (Promega), creating pMON25659 (FIG. 4). pMON25659 was digested with NcoI, BstXI, and BamHI, and the two fragments containing the ilvA gene were purified and cloned as a triple ligation into NcoI and BamHI-digested pSE280 (Invitrogen), creating plasmid pMON25660 (FIG. 5). Plasmid pMON25660 contains the IPTG-inducible ptrc promoter fused to the wild-type E. coli biosynthetic threonine deaminase gene (ilvA) for expression in E. coli.

IlvA was expressed from plasmid pMON25660 by growing E. coli cells transformed with pMON25660 by $CaCl_2$/heatshock treatment in Luria Broth (LB) at 37° C. to early log phase and inducing the cells with 0.5 mM IPTG. The addition of IPTG to the cells results in high level transcriptional activity from the ptrc promoter and expression of the IlvA.

IlvA protein extracts were prepared by pelleting induced cells, resuspending in 50 mM KPi and 5% glycerol, sonicating, and removing cellular debris by centrifugation. Extracts of *E. coli* containing IlvA were employed for biochemical studies as discussed below in the section entitled "Biochemical Analysis of Wild-type and Mutant *E. coli* Threonine Deaminases."

IlvA was further purified by the addition of protamine sulfate to the protein extract (3% final concentration) and incubation on ice for one hour. The precipitate was removed by centrifugation and discarded. The supernatant was brought to 20% ammonium sulfate concentration, incubated at 4° C. for one hour, and the precipitate was removed by centrifugation and discarded. Ammonium sulfate was added to the supernatant to 50% final concentration, and the precipitate was pelleted by centrifugation. The pellet was resuspended in Buffer A: 10 mM Bis-Tris-Propane, pH7.0, 1 mM EDTA, 1 mM DTT, and 1 mM isoleucine. The protein solution was dialyzed (molecular weight cutoff of 12–14 K) overnight in Buffer A. The dialyzed solution was loaded onto a Q-sepharose fast flow column (2.5 cm×40 cm, Pharmacia) pre-equilibrated with Buffer A. Elution of threonine deaminase was performed using 1250 ml Buffer A and 750 ml Buffer A plus 0.5M KCl (Buffer B). The elution gradient was increased from 0% to 75% B over 200 min. The flow rate was 10 ml/min and fractions were collected every 2.5 min. Active fractions were pooled and the enzyme precipitated by bringing the protein solution to 80% ammonium sulfate saturation. Precipitated protein was pelleted by centrifugation, the pellet was dissolved in a small about of Buffer A, and dialyzed overnight against Buffer A plus 0.01 mM pyridoxal phosphate. The dialyzed protein solution was loaded onto a Mono-Q 10/10 column pre-equilibrated with Buffer A. Elution of threonine deaminase was performed using 400 ml Buffer A and 200 ml Buffer B in a gradient from 0% to 70% B over 140 min. The flow rate was 4 ml/min and 2 min fractions were collected. Active fractions with the highest specific activity were analyzed by SDS-PAGE/Coomassie Blue staining (data not shown). The purest fractions were pooled and used for the production of polyclonal antibodies in rabbits. The remainder of the protein was stored at −80° C.

Mutagenesis of the *E. coli* Biosynthetic Threonine Deaminase Gene Single Replacement of Leucine With Phenylalanine at Amino Acid Position 447

The cloned wild-type *E. coli* threonine deaminase gene (ilvA) (SEQ ID NO:1) was modified by substituting a leucine (L) codon for a phenylalanine (F) codon at amino acid position 447 as in the *S. typhimurium* ilvA219 enzyme (LaRossa et al., 1987) as follows.

Figure 6:
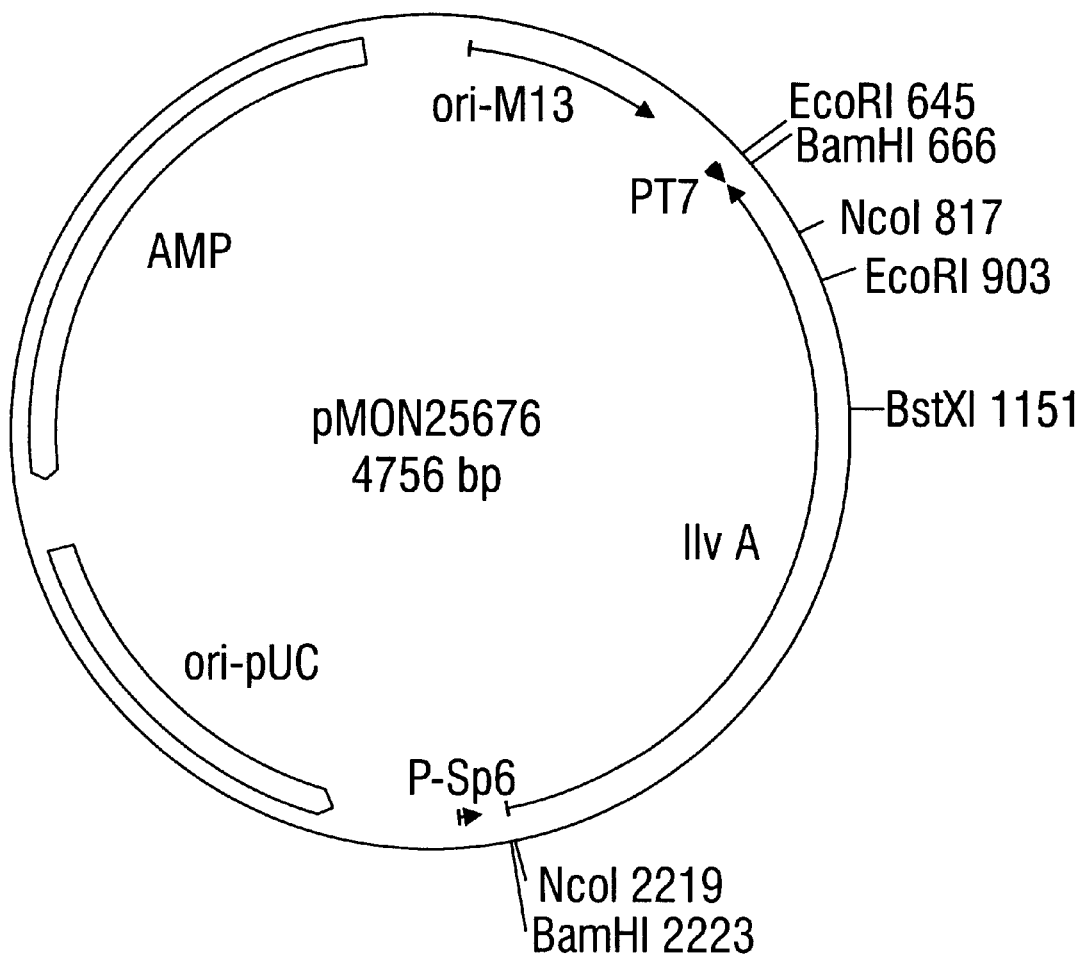
FIG. 6 shows the structure of pMON25676. pMON25676 contains the same BamHI fragment as is present in pMON25659. This plasmid was used for preparation of ssDNA for in vitro mutagenesis.

The cloned *E. coli* ilvA threonine deaminase gene sequence in plasmid pMON25659 was excised as a BamHI fragment and cloned into BamHI-digested pGEM-3zf(−) (Promega Corp.), creating pMON25676 (FIG. 6). Plasmid pMON25676 contains the M13 origin of replication for generation of single strand DNA (ssDNA). Single strand DNA from plasmid pMON25676 was prepared according to the pGEM® Single Strand systems procedure (Promega). The leucine codon corresponding to amino acid position 447 was modified by site-directed mutagenesis using BioRad's Muta-Gene® phagemid in vitro mutagenesis protocol employing the following synthetic mutagenic oligonucleotide (SEQ ID NO:4):

SEQ ID NO:4
CAGCTTCGAGTTCCCGGAATCAC-
CGGGCGCGTTCCTGCGCTTCC

Specifically, the use of this synthetic mutagenic oligonucleotide modified SEQ ID NO:1 at nucleotide positions 1,317 (changing adenine to guanine, therefore removing an EcoRI restriction enzyme site), 1,339 (changing cytosine to thymine), and 1,341 (changing guanine to cytosine). The combined substitutions at nucleotides 1,339 and 1,341 changed the codon for amino acid 447 from one encoding leucine to one encoding phenylalanine. The mutagenesis successfully recreated the *S. typhimurium* ilvA219 mutation in the *E. coli* biosynthetic threonine deaminase. The removal of the EcoRI restriction enzyme site allowed for rapid screening of the resultant transformants following mutagenesis. Successful mutagenesis was confirmed by testing the putative mutants for insensitivity to feedback inhibition by isoleucine, as discussed below in the section entitled "Biochemical Analysis of Wild-type and Mutant *E. coli* Threonine Deaminases."

Figure 7:
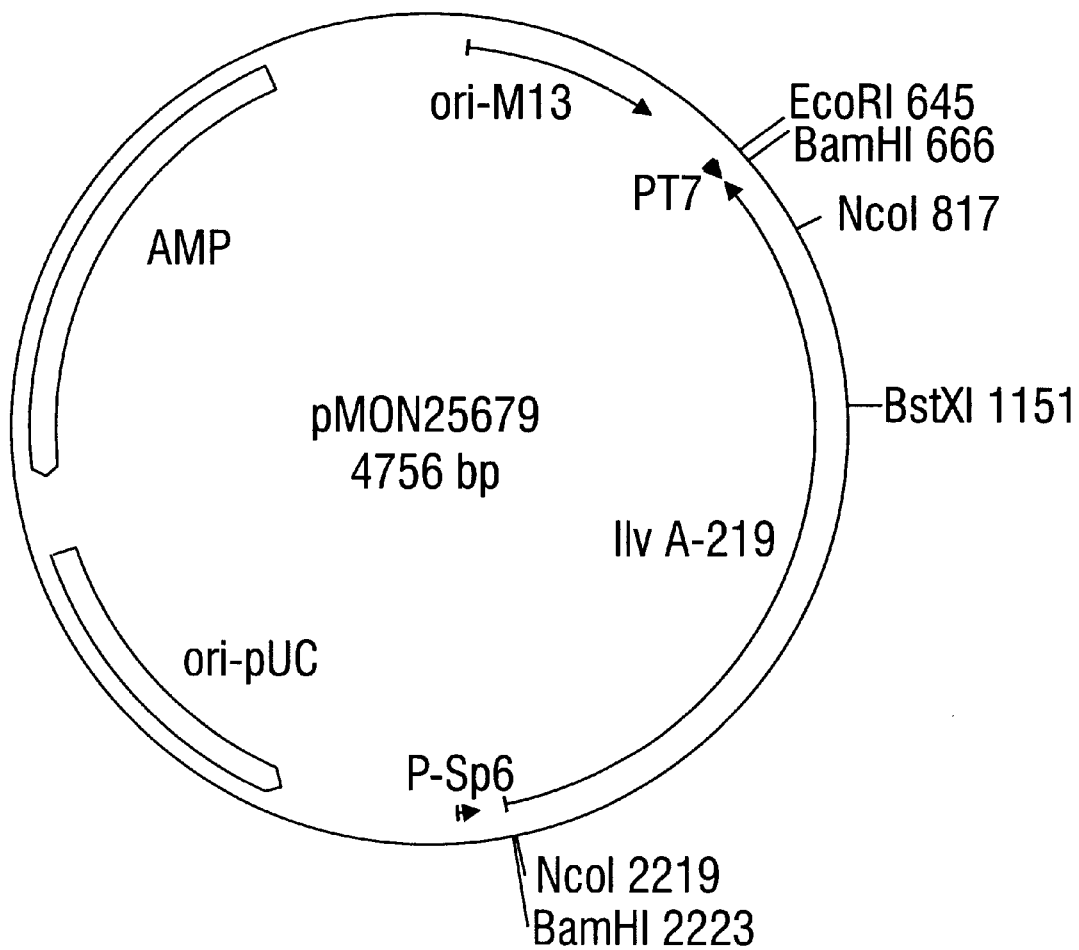
FIG. 7 shows the structure of pMON25679. pMON25679 contains the ilvA219 (L447F) gene encoding the mutant E. coli biosynthetic threonine deaminase created by site-directed mutagenesis of the wild-type threonine deaminase gene contained in plasmid pMON25676. The nucleotide sequence of the ilvA219 biosynthetic threonine deaminase gene is shown in SEQ ID NO:5.

The nucleotide sequence of the mutagenized *E. coli* biosynthetic threonine deaminase gene containing the ilvA219 (L447F) mutation is shown in SEQ ID NO:5. This mutant gene is contained in plasmid pMON25679 (FIG. 7).

Single Replacement of Leucine With Phenylalanine at Amino Acid Position 481

The cloned wild-type *E. coli* threonine deaminase gene in pMON25676 was modified by site-directed mutagenesis by substituting a leucine (L) codon for a phenylalanine (F) codon at amino acid position 481 as in the *E. coli* IlvA466 enzyme (Taillon et al., 1988) using the mutagenic oligonucleotide of SEQ ID NO:6 as follows.

SEQ ID NO:6
TATCGCAGCCACGGCACCGAC-
TACGGGCGCGTACTGGCGGCGTTC-
GAATTTGGC GACCATGAACC

Use of this synthetic mutagenic oligonucleotide changed the codon for amino acid 481 from one encoding leucine to one encoding phenylalanine by changing nucleotide 1,441 of SEQ ID NO:1 from cytosine to thymine. This substitution successfully recreated the *E. coli* ilvA466 (L481F) mutation. This mutagenic oligonucleotide also changed nucleotide position 1,404 from thymine (T) to cytosine (C), thereby removing an NcoI restriction enzyme recognition site. The removal of the NcoI restriction enzyme site allowed for rapid screening of the resultant transformants following mutagenesis. Successful mutagenesis was confirmed by testing the putative mutants for insensitivity to feedback inhibition by isoleucine as discussed below in the section entitled "Biochemical Analysis of Wild-type and Mutant *E. coli* Threonine Deaminases."

Figure 8:
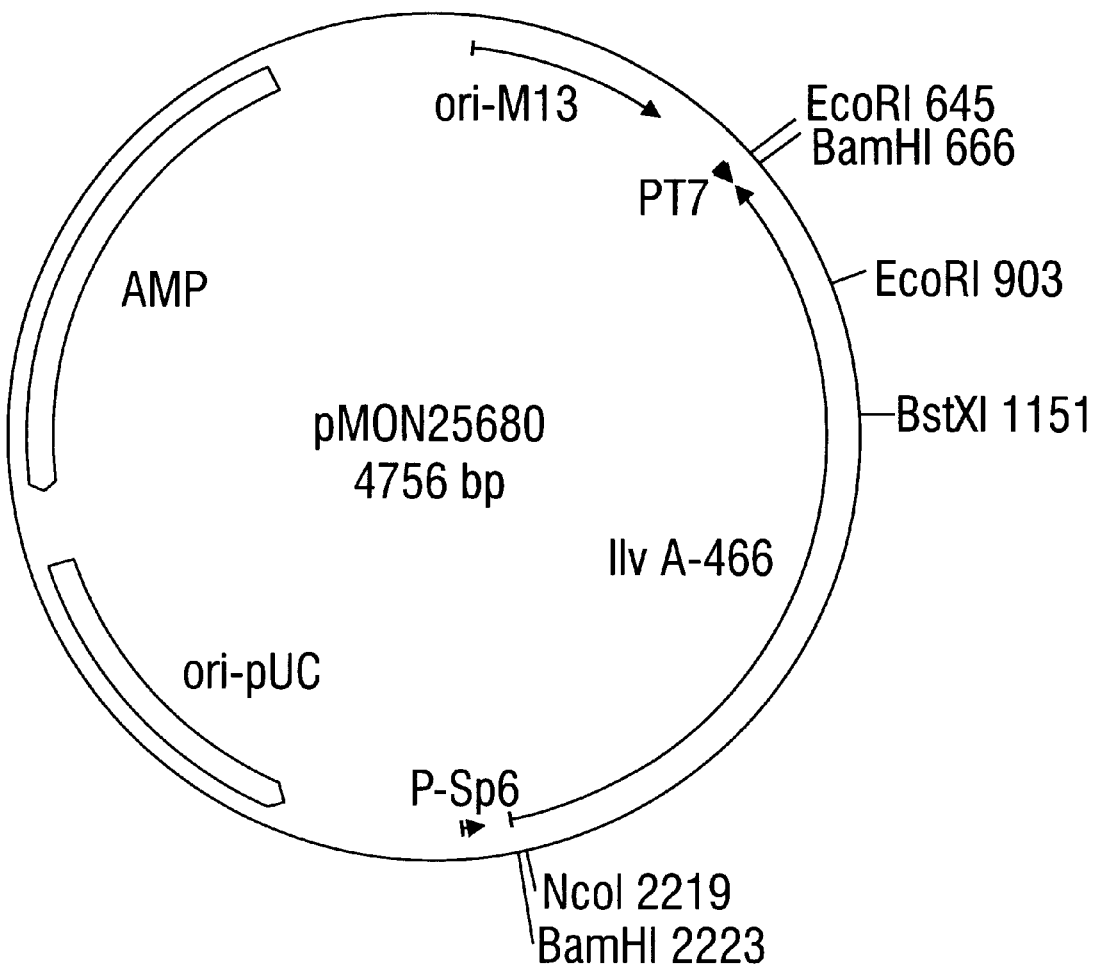
FIG. 8 shows the structure of pMON25680. pMON25680 contains the ilvA466 (L481F) gene encoding the mutant E. coli biosynthetic threonine deaminase created by site-directed mutagenesis of the wild-type threonine deaminase gene contained in plasmid pMON25676. The nucleotide sequence of the ilvA466 biosynthetic threonine deaminase gene is shown in SEQ ID NO:7.

The nucleotide sequence of the mutagenized *E. coli* biosynthetic threonine deaminase gene containing the ilvA466 (L481F) mutation is shown in SEQ ID NO:7. This mutant gene is contained in plasmid pMON25680 (FIG. 8).

Double Replacement of Leucine With Phenylalanine at Amino Acid Positions 447 and 481

Figure 9:
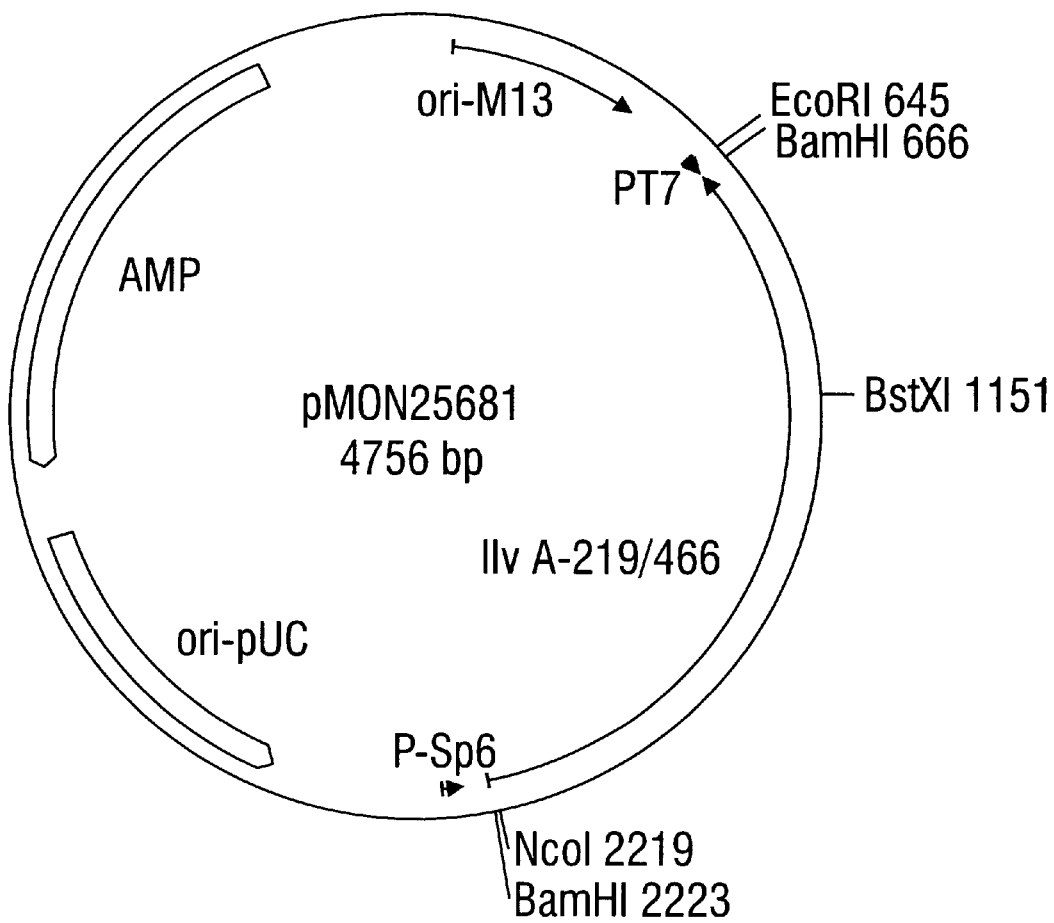
FIG. 9 shows the structure of pMON25681. pMON25681 contains the ilvA219/466 (L447F/L481F) gene encoding the mutant E. coli biosynthetic threonine deaminase created by site-directed mutagenesis of the wild-type threonine deaminase gene contained in plasmid pMON25676. The nucleotide sequence of the ilvA219/466 biosynthetic threonine deaminase gene is shown in SEQ ID NO:8.

Synthetic mutagenic oligonucleotides SEQ ID NO:4 and SEQ ID NO:6 were used in concert to create a double *E. coli* mutant gene (L447F and L481F), referred to as ilvA219/466. The nucleotide sequence of this double mutant gene is shown in SEQ ID NO:8. The removal of the NcoI and EcoRI restriction enzyme sites allowed for rapid screening of the resultant transformants following mutagenesis. Successful mutagenesis was confirmed by testing the putative mutants for insensitivity to feedback inhibition by isoleucine as discussed below in the section entitled "Biochemical Analysis of Wild-type and Mutant E. coli Threonine Deaminases." The IlvA219/466 double mutant gene is contained in pMON25681 (FIG. 9).

Cloning and Expression of the Mutant Threonine Deaminase Genes in E. coli

Figure 10:
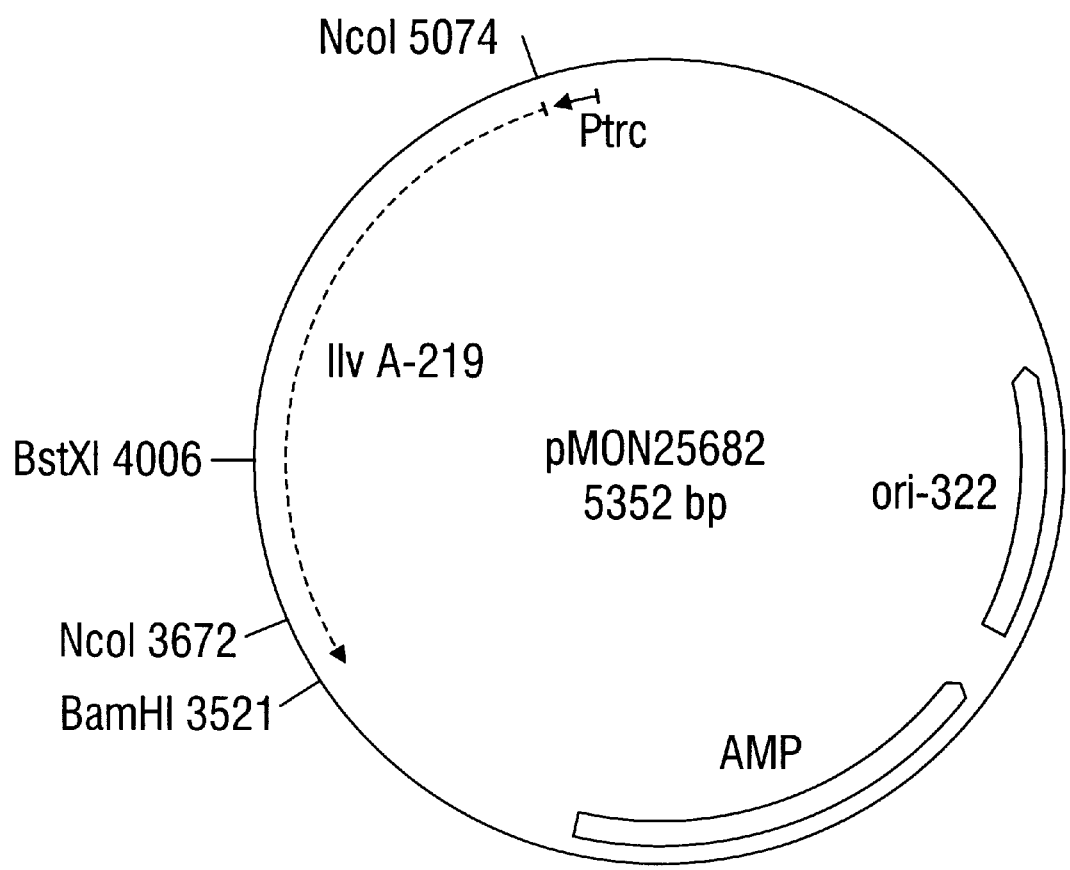
FIG. 10 shows the structure of pMON25682. pMON25682 was used for the overexpression in E. coli of the IlvA219 (L447F) mutant biosynthetic threonine deaminase from the ptrc promoter.

The plasmids pMON25679, pMON25680, and pMON25681 were separately digested with BstXI and BamHI, and the three mutant threonine deaminase genes obtained thereby were cloned into BstXI and BamHI-digested pMON25660 (FIG. 5). The resultant E. coli expression plasmids contained the ptrc promoter fused to the mutant ilvA genes for overexpression in E. coli. The cloning resulted in the following plasmids: pMON25682 (FIG. 10), containing the ilvA219 mutation (L447F); pMON25683 (FIG. 11), containing the ilvA466 mutation (L481F); and pMON25684 (FIG. 12), containing the ilvA219/466 mutations (L447F/L481F). Expression of all the IlvA mutant enzymes was performed as described above in "Cloning and Expression of the Wild-type E. coli Biosynthetic Threonine Deaminase." Extracts of E. coli containing the overexpressed mutant IlvAs were assayed for insensitivity to feedback inhibition by isoleucine as discussed below in the section entitled "Biochemical Analysis of Wild-type and Mutant E. coli Threonine Deaminases."

Biochemical Analysis of Wild-type and Mutant Threonine Deaminases

Kinetic analysis of the wild-type and mutant threonine deaminases was performed by determining threonine turnover catalyzed by these threonine deaminases as assayed by the method of Burns (1971). Specifically, α-keto-butyrate production was monitored by coupling to L-lactic dehydrogenase (LDH)-catalyzed reduction of the α-ketoacid in the presence of NADH to form (L)-2-hydroxybutyrate and $NAD^+$. The disappearance of NADH absorbance at 340 nm provides a measure of the threonine deaminase activity. Final reaction conditions were 100 mM KPi, pH 7.8, 0.20 mM NADH, 10 units/mL LDH (defined as LDH turnover of α-ketobutyrate, not pyruvate), and variable threonine. R. rubrum was grown according to Brandl et al., 1989. The growth and induction of E. coli cells overexpressing the mutant and wild-type biosynthetic threonine deaminases is described above. Cell extracts of R. rubrum and E. coli were prepared by sonicating pelleted cells (≈0.5 g from 100 ml of culture) in 2 ml of 100 mM KPi, pH 7.0, containing 5% (v/v) glycerol. After centrifugation to remove cellular debris, protein concentrations were determined by the method of Bradford (1976), and threonine deaminase activity was measured.

The kinetic parameters $K_m$ and $V_{max}$, and the level of positive cooperativity, i.e., the deviation from normal saturation kinetics where at low substrate concentration the substrate turnover rate is less than a non-cooperative system, were determined. These values were found by fitting the rate data to the Hill equation (Equation 1), which incorporates the coefficient n into the normal Michaelis-Menten equation (n=1 for a noncooperative system). An enzyme that displays no positive cooperativity exhibits an n value of ≤1.

$$v = V_{max} S^n / (K_m + S)^n \quad (1)$$

In addition to the kinetic parameters, the degree of inhibition of threonine deaminase by isoleucine was also measured at fixed levels of threonine.

The results are shown in Tables 1 and 2.

TABLE 1

General Rate Effects of Isoleucine on Mutant and Wild-Type Threonine Deaminases

| Threonine deaminase | Threonine Deaminase Specific Activity, u/mg (%)[1] | | |
|---|---|---|---|
| | 0 mM Isoleucine | 1.0 mM Isoleucine | 10.0 mM Isoleucine |
| E. coli wild-type | 16.7 | 0.3 (<2) | 0.3 (<2) |
| E. coli L447F | 16.0 | 16.3 (102) | 14.9 (93) |
| E. coli L481F | 20.3 | 11.3 (56) | 0.3 (<2) |
| E. coli L447F/L481F | 22.0 | 22.8 (103) | 21.9 (99) |
| R. rubrum wild-type | 11.2 | no data | 10.0 (90) |
| R. rubrum wild-type (0.5 mM threonine) | 1.2 | no data | 1.1 (90) |

[1]Rates were determined using 10 mM threonine as substrate, except where indicated, at the indicated concentrations of isoleucine. Values in parenthesis are % activity relative to the results with 0 mM isoleucine.

As shown in Table 1, the E. coli IlvA219 enzyme (E. coli L447F mutant) is insensitive to isoleucine inhibition up to a concentration of 10 mM isoleucine. The E. coli IlvA466 enzyme (E. coli L48 1F mutant) exhibits a more modest level of insensitivity to inhibition by isoleucine, exhibiting 44% inhibition of enzyme activity at 1 mM isoleucine and 98% inhibition at 10 mM isoleucine. The novel double mutant enzyme (E. coli L447F/L48 1F mutant) is an improvement over the L447F mutant, exhibiting no inhibition at all in the presence of 10 mM isoleucine.

In addition to greatly enhanced insensitivity to isoleucine, the three mutant enzymes exhibit other enhanced kinetic properties. As shown in Table 2, the three mutant threonine deaminases exhibit lower $K_m$ values and reduced or eliminated positive cooperativity compared to the wild-type enzyme. The latter is indicated by n values less than that of wild-type E. coli threonine deaminase (Table 2). The combination of a reduced n value and lower $K_m$ can have a profound effect on the rate of substrate turnover, especially at low substrate concentrations. For example, using the reported $K_m$ and n values for the threonine deaminases reported in Table 2, with equivalent $V_{max}$ values and threonine=0.5 mM, the L447F mutant is approximately a factor of 10 faster in substrate turnover than the wild-type enzyme.

TABLE 2

Kinetic Parameters for Mutant and Wild-type Threonine Deaminases

| Enzyme[1] | $K_m$ Threonine (mM) | Hill Coefficient (n) |
|---|---|---|
| E. coli wild-type | 5 ± 1 | 1.5 ± 0.2 |
| E. coli L447F | 2.01 ± 0.06 | 0.91 ± 0.03 |
| E. coli L481F | 3.08 ± 0.03 | 1.22 ± 0.01 |
| E. coli L447F/L481F | 2.15 ± 0.07 | 0.91 ± 0.04 |
| R. rubrum wild-type | 8.6 ± 0.3 | 0.79 ± 0.03 |

[1]The $V_{max}$ for all threonine deaminases are within a factor of two of each other, being approximately 250–500 units/mg.

In vivo Analysis of Cloned E. coli ilvA Genes

In order to determine if overexpression of the wild-type E. coli biosynthetic threonine deaminase (IlvA) or an isoleucine-deregulated threonine deaminase mutant (for example, the IlvA466 (L481F) mutant E. coli threonine deaminase) could produce enhanced α-ketobutyrate levels or P(3HB-co-3HV) copolymer from glucose and threonine in combination with the PHB biosynthetic operon of A. eutrophus, the following experiment was performed.

E. coli DH5α cells were transformed with pJM9238 (Kidwell et al., 1995) containing the PHB operon of A. eutrophus by CaCl₂/heat shock treatment The PHB operon was under the inducible control of of the ptac promoter. E. coli containing pJM9236 were used as a background control with respect to threonine deaminase activity.

E. coli DH5α cells were also cotransformed by CaCl₂/heat shock treatment with pJM9238 and pMON25660 (FIG. 5) containing the wild-type E. coli threonine deaminase, under ptrc inducible control.

In a third experiment, E. coli DH5α cells were cotransformed with pJM9238 and pMON25683 (FIG. 11) containing the mutant E. coli ilvA466 (L481F) threonine deaminase, under ptrc inducible control.

Transformed cells were grown on M9 minimal salts plus 0.2% gluconate and 25 mM L-threonine. At early log phase, the cells were induced with IPTG to induce expression of all four enzymes (i.e., PhbA, PhbB, PhbC, and IlvA or IlvA466). Threonine deaminase activity was measured in cell extracts as described above in the section entitled "Biochemical Analysis of Wild-type and Mutant E. coli Threonine Deaminases." Intracellular α-ketobutyrate was isolated from approximately 50 mg (wet weight) of cells pelleted by centrifugation and then resuspended and sonicated in 1 ml of 100 mM KPi, pH 7.0, containing 5% glycerol (v/v). The level of α-ketobutyrate was determined by reverse-phase HPLC isolation of the dinitrophenylhydrazine derivative of the α-ketoacid according to Qureshi et al., (1982). Quantitation was based on peak integration comparisons to a standard curve.

The PHA produced by the cells was extracted, hydrolyzed to the methylester, and analyzed by gas chromatography (GC) according to the following procedure. The polymer was first extracted by centrifuging the cells at 7,000 rpm for 20 min., washing with 25 ml methanol, recentrifuging, washing with 15 ml hexane, and recentrifuging. Cell pellets were dried under N₂ for two hours, and the dry cell weights determined. 6.5 ml of chloroform were added to extract the PHA at 100° C. for one hour. The solution was cooled and filtered through a PTFE syringe filter (13 mm diameter, 0.45 μm pore). The PHA was precipitated by the addition of 50 ml of methanol, collected by centrifugation, and then washed with hexane. The polymer was dried at 70° C. for two hours, and after drying, the polymer weight was determined.

The recovered PHAs were subjected to methanolysis by the method described by Brandl et al., (1988), with some modifications. Three to four milligrams of the polymer were dissolved in one ml chloroform containing a known amount (3.157 μmol/ml in a typical example) of methyl benzoate internal standard (Aldrich Chemical Company, USA) in a small screw-cap test tube. To this, 0.85 ml of methanol and 0.15 ml of concentrated sulfuric acid were added, and the mixture was refluxed at 100° C. for 140 min. At the end of the reaction, 0.5 ml of deionized water was added and the tube vortexed for one min. After phase separation, the organic phase (bottom layer), which contains the methyl esters of the constituent β-hydroxy-carboxylic acids from the PHAs, was removed and dried over sodium sulfate, and then used for analysis.

The methyl esters were assayed by gas chromatography in order to determine the original copolymer composition, using a Varian 3400 gas chromatograph equipped with a DB-5 capillary column (0.25 mm×30 m, 0.25μ film thickness; J&W Scientific, USA), a flame ionization detector, a Varian 8200 Autosampler, and a workstation with the Varian Star Chromatography software. 1 μl of the sample was injected by split injection (split ratio of 50:1), using helium as the carrier gas (flow rate 2.5 ml/min). The temperatures of the injector and detector were kept at 250° C. A temperature program was used which separated the β-hydroxybutyric acid and β-hydroxyvaleric acid methyl esters efficiently (60° C. for 3 min; temperature ramp of 12° C./min to 120° C.; temperature ramp of 30° C./min to 300° C.; 300° C. for 10 min). Under these conditions, the retention times of the methyl esters of β-hydroxybutyric acid and β-hydroxyvaleric acid were approximately 3.1 min and 4.8 min, respectively, while that of the methyl benzoate was 7.02 min. Quantitation was carried out based on standard curves generated using methyl-3-(D)-hydroxybutyrate and methyl-3-(D)-hydroxyvalerate (both obtained from Fluka, USA) as external calibration standards. In order to take into account the partitioning (Jan et al., 1995) of the methyl esters between the organic and aqueous phases, as well as to correct for the differences in partition coefficients of the respective methyl esters, the standards were treated in a manner identical to that described above for the PHAs (except for the omission of the reflux step) prior to generating the standard curves.

The mol % C5 (3HV component) was determined in the isolated polymer. The results are shown in Table 3.

TABLE 3

Effect of Threonine Deaminase on α-Ketobutyrate Production and % C5 Content in PHBV[3]

| Tda[1] E. coli construc | Threonine Deaminase Specific Activity, u/mg (%)[2] | | [α-keto-butyrate] μM | % PHBV Dry Weight (% C5) |
|---|---|---|---|---|
| | 0 mM Isoleucine | 0.1 mM Isoleucine | | |
| pJM9238[4] | <0.04 | <0.04 | 13.4 | 35 (1.3) |
| pJM9238/pMON25660[5] | 4.20 | 0.16 (3.8) | 41.8 | 22 (1.1) |
| pJM9238/pMON25683[6] | 0.59 | 0.56 (95) | 579 | 27 (0.9) |

[1]Tda refers to threonine deaminase.
[2]Rates were determined using 10 mM threonine as substrate, at the indicated concentrations of isoleucine. Values in parenthesis are % activity relative to the 0 mM isoleucine results.
[3]PHBV refers to P(3HB-co-3HV) copolymer.
[4]pJM9238 contains the A. eutrophus PHB operon.
[5]pMON25660 contains the wild-type E. coli threonine deaminase.
[6]pMON25683 contains the L481F mutant E. coli threonine deaminase.

Table 3 shows that there is about a three-fold increase in α-ketobutyrate concentration for the overexpressed wild-type threonine deaminase compared to cells not overexpressing a threonine deaminase (41.8 μM vs. 13.4 μM α-keto-butyrate). This is evidently a reflection of the strong feedback regulation of the wild-type enzyme by isoleucine in vivo. In contrast, the transformed cells containing the L481F mutant threonine deaminase accumulated α-ketobutyrate to a level greater than 40 times that in cells containing no overexpressed threonine deaminase (579 μM vs. 13.4 μM). This occurred despite the fact that the threonine deaminase activity in the transformants containing overexpressed wild-type enzyme was much greater than that in transformants containing the L481F mutant (4.20 u/mg vs. 0.59 u/mg in the absence of isoleucine). It is also noteworthy that the α-ketobutyrate concentrations reported in Table 3 are for a 1 ml extract solution from approximately 50 mg of cells, and therefore represent a significant dilution of the intracellular metabolite, probably by a minimum factor of 10.

Figure 2:
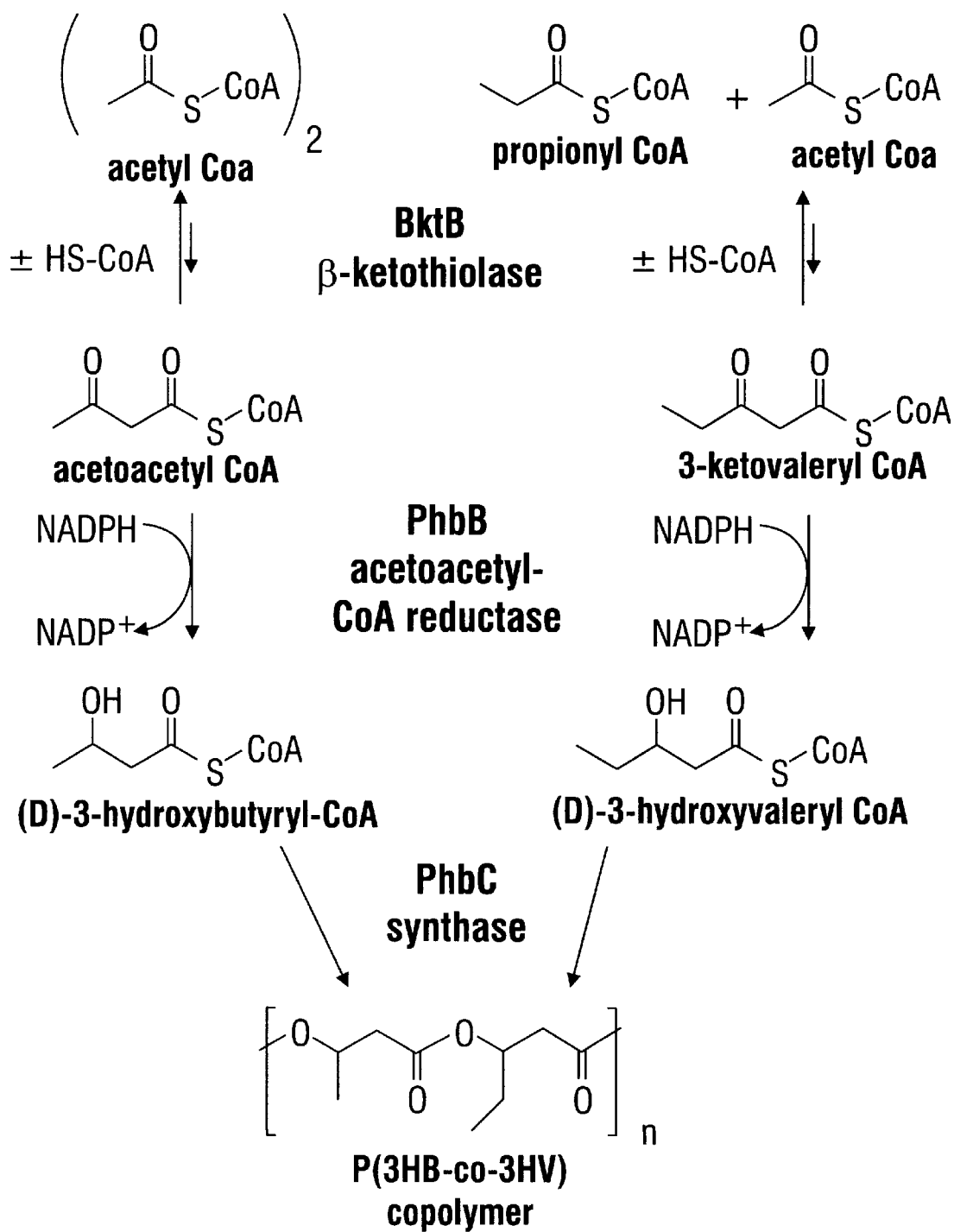
FIG. 2 shows the biochemical steps involved in the production of P(3HB-co-3HV) copolymer from acetyl-CoA and propionyl-CoA catalyzed by PHA biosynthetic enzymes of A. eutrophus.

If simply increasing the levels of α-ketobutyrate was sufficient to produce a significant 3HV component in the P(3HB-co-3HV) copolymer, then there should have been significantly more 3HV in the copolymer when employing pJM9238/pMON25683 than when employing pJM9238/pMON25660. As shown in Table 3, this was not the case. This result suggests either that the α-ketobutyrate was not being converted to propionyl-CoA, or that the *A. eutrophus* PHB biosynthetic enzymes encoded by pJM9238 could not efficiently catalyze formation of the C5 substrate ((D)-3-hydroxy-valeryl-CoA, FIG. 2) for incorporation into the polymer. The results presented in Example 8 strongly suggest that this is at least partially due to a block in the ability of the *A. eutrophus* PhbA to catalyze the condensation of acetyl-CoA and propionyl-CoA.

In summary, it is evident from the data in Tables 1–3 that mutant, deregulated threonine deaminases similar to those described herein possess a desirable deregulated phenotypic property useful in enhancing the level of α-ketobutyrate in organisms such as bacteria and plants targeted for the production of P(3HB-co-3HV). Isoleucine-deregulated threonine deaminases useful in the present invention preferably possess a level of isoleucine insensitivity such that at 100 μM isoleucine and 10 mM threonine, the enzymes exhibit ≧10% activity relative to assay conditions in which isoleucine is absent. In addition to exhibiting reduced isoleucine sensitivity, threonine deaminases useful in the present invention can also exhibit reduced or no positive cooperativity compared to the corresponding wild-type enzymes (Hill coefficient<1.5), and have kinetic parameters of $K_m$ and $V_{max}$ in the range of the wild-type enzyme (e. g., $V_{max}$=10–1000 U/mg, $K_m$=0.1 to 20 mM).

The present invention encompasses not only the DNA sequences shown in SEQ ID NOS: 5,7, and 8 and the proteins encoded thereby, but also biologically functional equivalent nucleotide and amino acid sequences. The phrase "biologically functional equivalent nucleotide sequences" denotes DNAs and RNAs, including chromosomal DNA, plasmid DNA, cDNA, synthetic DNA, and mRNA nucleotide sequences, that encode peptides, polypeptides, and proteins exhibiting the same or similar threonine deaminase enzymatic activity as that of the mutant *E. coli* threonine deaminases encoded by SEQ ID NOS: 5, 7, and 8, respectively, when assayed enzymatically by the methods described herein, or by complementation. Such biologically functional equivalent nucleotide sequences can encode peptides, polypeptides, and proteins that contain a region or moiety exhibiting sequence similarity to the corresponding region or moiety of the *E. coli* IlvA muteins.

One can isolate threonine deaminases useful in the present invention from various organisms based on homology or sequence identity. Although particular embodiments of nucleotide sequences encoding deregulated threonine deaminases are shown in SEQ ID NOS: 5, 7, and 8, it should be understood that other biologically functional equivalent forms of such deregulated threonine deaminase-encoding nucleic acids can be readily isolated using conventional DNA-DNA or DNA-RNA hybridization techniques. Thus, the present invention also includes nucleotide sequences that hybridize to any of SEQ ID NOS: 5, 7, and 8 and their complementary sequences, and that code on expression for peptides, polypeptides, and proteins exhibiting the same or similar enzymatic activity as that of these deregulated threonine deaminases. Such nucleotide sequences preferably hybridize to SEQ ID NOS: 5, 7, or 8 or their complementary sequences under moderate to high stringency (see Sambrook et al., 1989). Exemplary conditions include initial hybridization in 6×SSC, 5× Denhardt's solution, 100 mg/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize under salt and temperature conditions equivalent to those described above to genomic DNA, plasmid DNA, cDNA, or synthetic DNA molecules that encode the same amino acid sequences as these nucleotide sequences, and genetically degenerate forms thereof due to the degenerancy of the genetic code, and that code on expression for a peptide, polypeptide, or protein that has the same or similar threonine deaminase enzymatic activity as that of the deregulated threonine deaminases disclosed herein.

Biologically functional equivalent nucleotide sequences of the present invention also include nucleotide sequences that encode conservative amino acid changes within the amino acid sequences of the present deregulated threonine deaminases, producing silent changes therein. Such nucleotide sequences thus contain corresponding base substitutions based upon the genetic code compared to the nucleotide sequences encoding the present deregulated threonine deaminases. Substitutes for an amino acid within the fundamental mutant deregulated *E. coli* threonine deaminase amino acid sequences discussed herein can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid changes within the present mutant deregulated *E. coli* threonine deaminase sequences can be made by substituting one amino acid within one of these groups with another amino acid within the same group. While biologically functional equivalents of these mutant deregulated threonine deaminases can have any number of conservative amino acid changes that do not significantly affect the threonine deaminase enzymatic activity of this enzyme, 10 or fewer conservative amino acid changes may be preferred. More preferably, seven or fewer conservative amino acid changes may be preferred; most preferably, five or fewer conservative amino acid changes may be preferred. The encoding nucleotide sequences (gene, plasmid DNA, cDNA, synthetic DNA, or mRNA) will thus have corresponding base substitutions, permitting them to code on expression for the biologically functional equivalent forms of the mutant deregulated *E. coli* threonine deaminases.

In addition to nucleotide sequences encoding conservative amino acid changes within the amino acid sequences of the present mutant threonine deaminases, biologically functional equivalent nucleotide sequences of the present invention also include genomic DNA, plasmid DNA, cDNA, synthetic DNA, and mRNA nucleotide sequences encoding non-conservative amino acid substitutions, additions, or deletions. These include nucleic acids that contain the same inherent genetic information as that contained in the DNA of SEQ ID NOS:5, 7, and 8, and which encode peptides, polypeptides, or proteins exhibiting the same or similar enzymatic activity as that of the present mutant deregulated threonine deaminases. Such nucleotide sequences can encode fragments or variants of these threonine deaminases. The enzymatic activity of such fragments and variants can be determined by complementation or enzymatic assays as described above. These biologically functional equivalent nucleotide sequences can possess from 40% sequence identity, or from 60% sequence identity, or from 80% sequence identity, to 100% sequence identity to the DNAs encoding the present deregulated threonine deaminases, or corresponding regions or moieties thereof. However, regardless of the percent sequence identity of these biologically functional equivalent nucleotide sequences, the encoded proteins would possess the same or similar enzymatic activity as the deregulated threonine deaminases disclosed herein. Thus, biologically functional equivalent nucleotide sequences encompassed by the present invention include sequences having less than 40% sequence identity to any of SEQ ID NOS: 5, 7, and 8, so long as they encode peptides, polypeptides, or proteins having the same or similar enzymatic activity as the deregulated threonine deaminases disclosed herein.

Mutations made in *E. coli* threonine deaminase cDNA, chromosomal DNA, plasmid DNA, synthetic DNA, mRNA, or other nucleic acid preferably preserve the reading frame of the coding sequence. Furthermore, these mutations preferably do not create complementary regions that could hybridize to produce secondary mRNA structures, such as loops or hairpins, that would adversely affect mRNA translation.

Useful biologically functional equivalent forms of the DNAs of SEQ ID NOS:5, 7, and 8 include DNAs comprising nucleotide sequences that exhibit a level of sequence identity to corresponding regions or moieties of these DNA sequences from 40% sequence identity, or from 60% sequence identity, or from 80% sequence identity, to 100% sequence identity to the DNAs encoding the present deregulated threonine deaminases, or corresponding regions or moieties thereof However, regardless of the percent sequence identity of these nucleotide sequences, the encoded proteins would possess the same or similar enzymatic activity as the deregulated threonine deaminases disclosed herein. Thus, biologically functional equivalent nucleotide sequences encompassed by the present invention include sequences having less than 40% sequence identity to any of SEQ ID NOS:5, 7, and 8, so long as they encode peptides, polypeptides, or proteins having the same or similar enzymatic activity as the deregulated threonine deaminases disclosed herein. Sequence identity can be determined using the "BestFit" or "Gap" programs of the Sequence Analysis Software Package, Genetics Computer Group, Inc., University of Wisconsin Biotechnology Center, Madison, Wis. 53711.

Due to the degeneracy of the genetic code, i.e., the existence of more than one codon for most of the amino acids naturally occuring in proteins, genetically degenerate DNA (and RNA) sequences that contain the same essential genetic information as the DNAs of SEQ ID NOS:5, 7, and 8 of the present invention, and which encode the same amino acid sequences as these nucleotide sequences, are encompassed by the present invention. Genetically degenerate forms of any of the other nucleic acid sequences discussed herein are encompassed by the present invention as well.

The nucleotide sequences described above are considered to possess a biological function substantially equivalent to that of the mutant *E. coli* threonine deaminase-encoding DNAs of the present invention if they encode peptides, polypeptides, or proteins having isoleucine-deregulated threonine deaminase enzymatic activity differing from that of any of the mutant *E. coli* threonine deaminases disclosed herein by about ±30% or less, preferably by about ±20% or less, and more preferably by about ±10% or less when assayed in vivo by complementation or by the enzymatic assays discussed above.

EXAMPLE 3

Increased Production of α-Ketobutyrate Via Use of the Threonine Deaminase of *Rhodospirillum rubrum*

The phototrophic, non-sulfur purple bacterium *Rhodospirillum rubrum* (ATCC 25903) is the source of a natural deregulated threonine deaminase (Feldberg and Datta, 1971). As shown in Tables 1 and 2, above, the threonine deaminase from *R. rubrum* displays normal Michaelis-Menten behavior, and is not significantly feedback inhibited by isoleucine. This enzyme is also unaffected by activators of the degradative enzyme (Feldberg and Datta, 1971). The *R. rubrum* threonine deaminase can therefore also be expressed in bacteria and plants in order to enhance the production of α-ketobutyrate from L-threonine.

SDS-PAGE analysis indicates that the monomeric molecular weight of the *R. rubrum* threonine deaminase is approximately 42 kD (data not shown). This is intermediate between the molecular weight of the *E. coli* biosynthetic (56 kD) and biodegradative enzymes (35 kD). The *R. rubrum* enzyme may therefore represent a third class of threonine deaminase useful in the present invention. Möckel et al. (1994) similarly observed that the threonine deaminase of *C. glutamicium* was of intermediate molecular weight, having a C-terminal deletion of 95 amino acids.

From what is known of other threonine deaminases, it is probable that the C-terminal domain of the *R. rubrum* enzyme is truncated, resulting in the deregulated phenotype of the enzyme. Taillon et al. (1988) published an amino acid comparison of three biosynthetic threonine deaminases and one biodegradative threonine deaminase. This comparison revealed N-terminal conservation between the two forms of threonine deaminase. The N-terminus appears to be involved in catalysis. The biodegradative form of the enzyme is truncated at the C-terminus, and it has been suggested that this deletion results in the isoleucine-deregulated phenotype (Taillon et al., 1988). Based on SDS-PAGE analysis of the *R. rubrum* threonine deaminase which indicates that the *R. rubrum* enzyme posses a molecular weight intermediate between that of the biosynthetic and degradative enzymes, the *R. rubrum* threonine deaminase may have a truncated C-terminus, effectively deleting the regulatory domain.

EXAMPLE 4

Increased Production of α-Ketobutyrate Using Other Modified or Naturally-Occurring Forms of Threonine Deaminase Deregulated threonine deaminases useful in the present invention can be either naturally-occurring, or produced by recombinant DNA techniques such as those employed in Example 2. If naturally-occurring, such threonine deaminases can be identified by screening organisms for threonine deaminase activity, followed by measuring the sensitivity of that activity to isoleucine inhibition using the standard assay methods described above. Genes for these enzymes can then be isolated by complementation into threonine deaminase-negative bacteria (Fisher and Eisenstein, 1993). The levels of isoleucine analogs such a L-O-methylthreonine (OMT) in the growth medium can be varied during the complementation procedure to select organisms that express isoleucine-deregulated biosynthetic threonine deaminases. Alternatively, genes for threonine deaminases can be obtained by hybridization techniques using an appropriate probe, preferably based upon the nucleotide sequence comprising the N-terminal region of the biosynthetic threonine deaminase. Following expression of these isolated genes in an appropriate host, they can be tested for isoleucine insensitivity as described previously.

Alternatively, deregulated threonine deaminases can be created by physical or chemical mutagenesis of wild-type threonine deaminase genes utilizing a variety of techniques known in the art to introduce either specific or random mutations into such genes (Eisenstadt et al., 1994; as described in Example 2; Feldmann et al., 1994). Muteins created in this way can be analyzed by methods such as those described in Example 2 to determine catalytic efficiencies and the extent of inhibition by isoleucine.

One strategy for creating deregulated threonine deaminases useful in the present invention is based upon knowledge of the functional domains of this enzyme. The functional domains of both the degradative and biosynthetic types of threonine deaminase have been analyzed (Taillon et al., 1988). All known mutations affecting feedback inhibition of the biosynthetic threonine deaminase are C-terminal region mutations. If the biosynthetic threonine deaminase is compared to the biodegradative threonine deaminase at the amino acid level, it can be seen that the regions of homology between the two forms exist only in the N-terminal regions of the polypeptides. Since the biodegradative form of the enzyme is not regulated by isoleucine, the N-terminal region is likely responsible for the catalytic activity, while the C-terminal region is likely involved in the feedback regulation (Fisher and Eisenstein, 1993). This knowledge of the regulatory domains of the enzyme suggests that modification of the C-terminal region will produce mutants with desirable properties for the purposes disclosed herein. For example, portions of the C-terminal region of the biosynthetic threonine deaminase can be sequentially deleted, and the remainder of the enzyme polypeptide assayed for activity to isolate deregulated deletion mutants. Deletions of the C-terminal region of the biosynthetic deaminase can be produced by a variety of techniques known in the art. For example, Exonuclease III can be used to create a ladder of 3' deletions. Following expression of the truncated genes, the enzymatic activity of the modified deaminases can be assayed as described above.

Alternatively, various domains of different threonine deaminases can be replaced with one another to determine their effect on enzyme regulation. For example, the C-terminal region of a biosynthetic threonine deaminase can be replaced with the C-terminal region of a biodegradative threonine deaminase such as that from E. coli, and the resulting polypeptide assayed for feedback inhibition by isoleucine. Domain swapping has been discused in Cohen and Curran 1990; Czerny et. al., 1993; and Zinszner et. al., 1994.

Mutants of biodegradative threonine deaminase that are not inhibited by pyruvate, or which do not require activation by AMP, can be generated by random mutagenesis of a cloned biodegradative threonine deaminase, or by swapping domains of the biodegradative threonine deaminase with those of the biosynthetic enzyme. Such mutant biodegradative threonine deaminases can be use to generate high levels of α-ketobutyrate in plants or bacteria. No biodegradative threonine deaminase has yet been reported that does not require a metabolite for activation.

EXAMPLE 5

Figure 13:
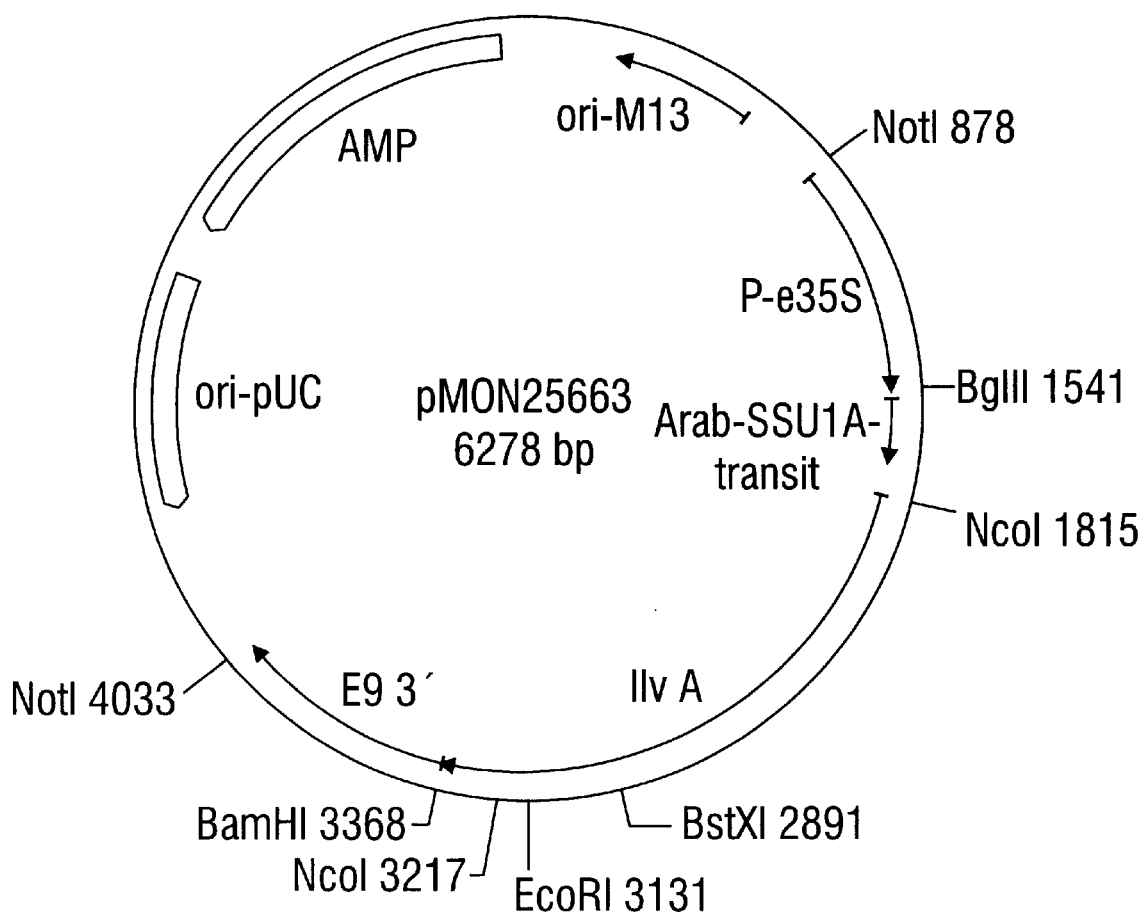
FIG. 13 shows the structure of pMON25663. pMON25663 was used for transient expression of the wild-type E. coli threonine deaminase (IlvA) in tobacco protoplasts.
Figure 14:
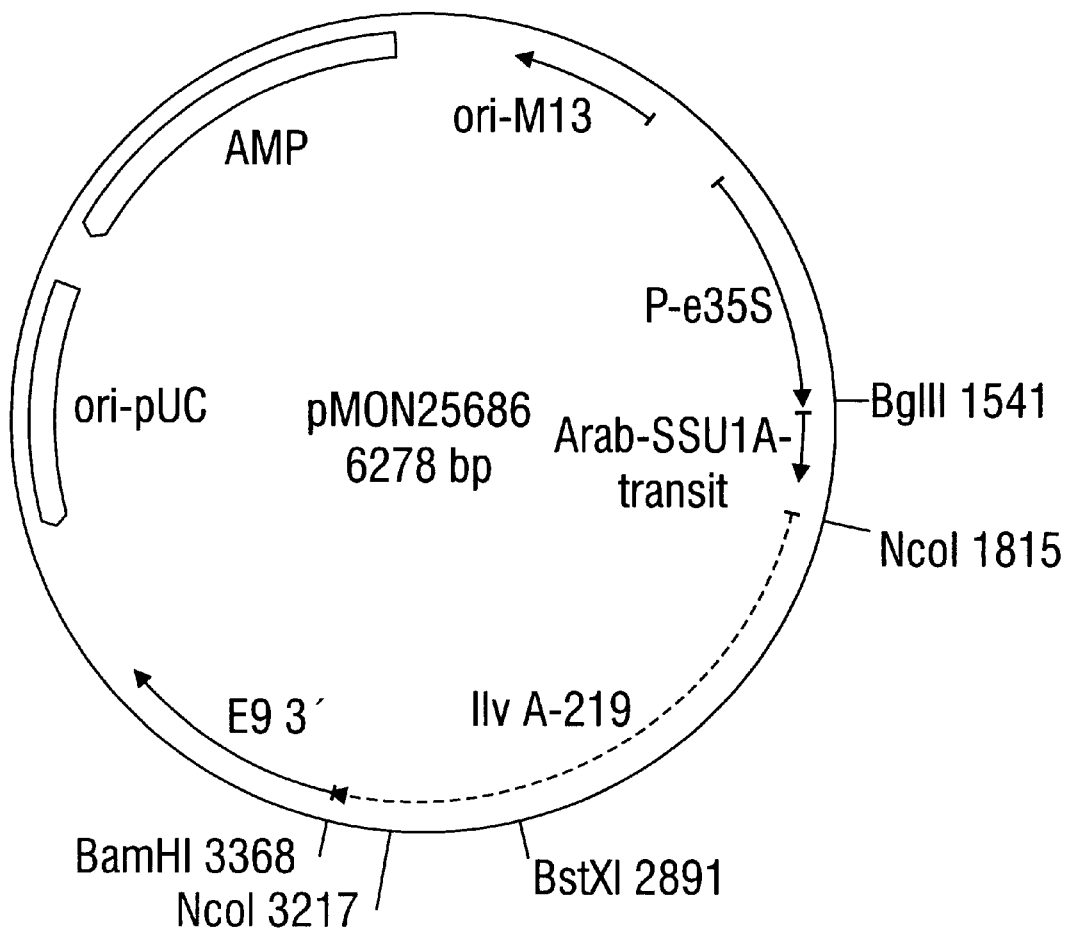
FIG. 14 shows the structure of pMON25686. pMON25686 was used for transient expression of the IlvA219 (L447F) mutant threonine deaminase in tobacco protoplasts.
Figure 15:
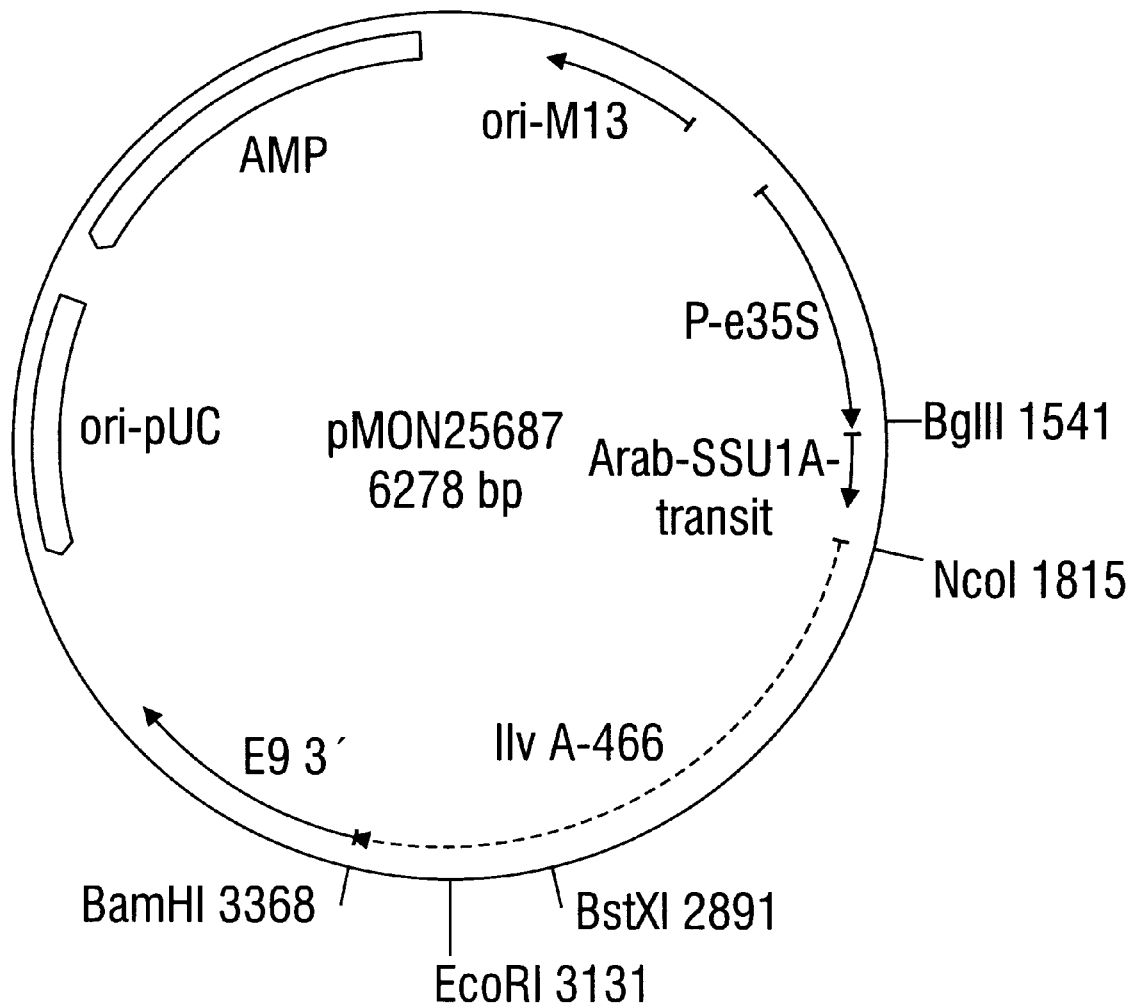
FIG. 15 shows the structure of pMON25687. pMON25687 was used for transient expression of the IlvA466 (L481F) mutant threonine deaminase in tobacco protoplasts.
Figure 16:
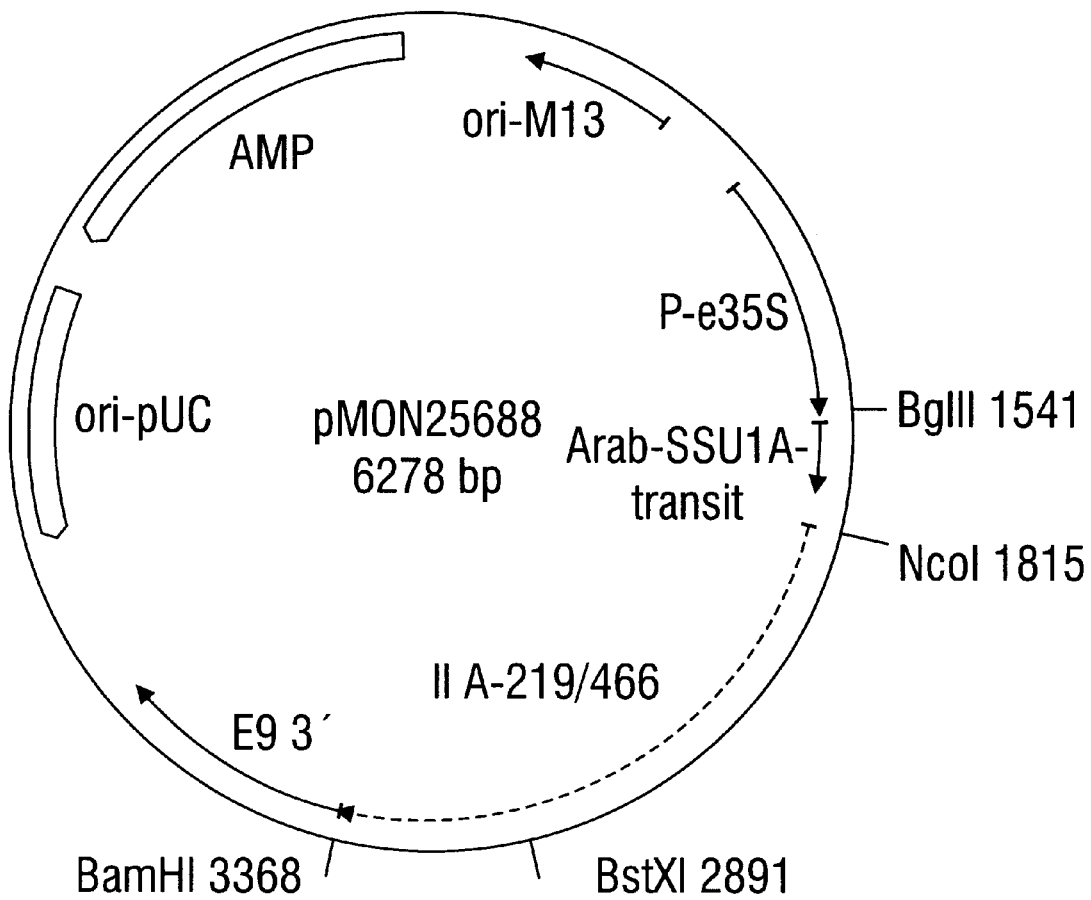
FIG. 16 shows the structure of pMON25688. pMON25688 was used for transient expression of the IlvA219/466 (L447F/L481F) mutant threonine deaminase in tobacco protoplasts.
Figure 17:
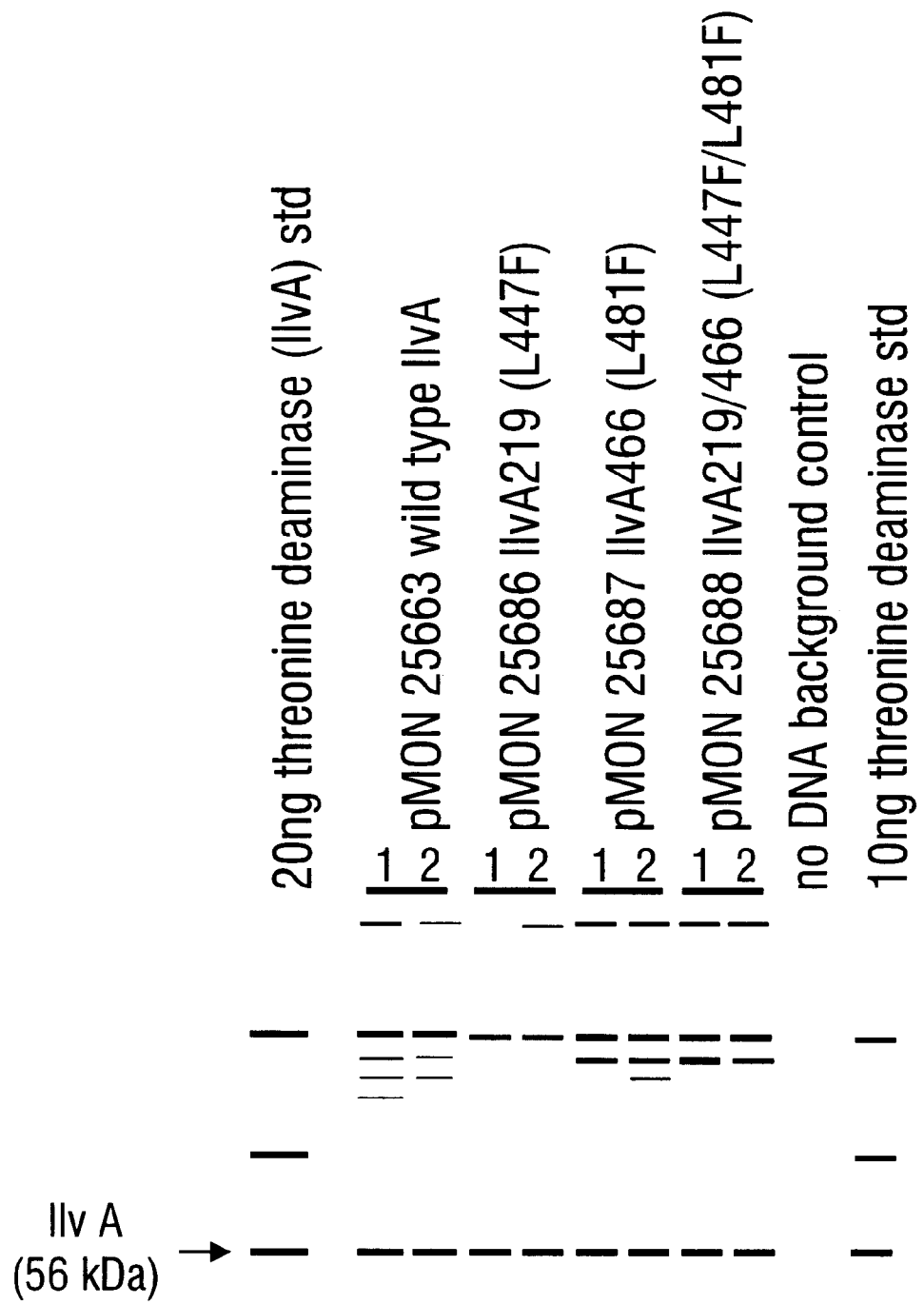
FIG. 17 shows the expression, confirmed by Western blot analysis, of wild-type and mutant biosynthetic E. coli threonine deaminases in tobacco protoplasts via electroporation with plasmids pMON26663, pMON25686, pMON25687, and pMON25688. Immunoreactive bands corresponding to the predicted molecular weight of each threonine deaminase (56 kDa) were observed in replicates, designated "1" and "2".

Expression and Activity of Wild-type and Mutant Threonine Deaminases in Plant Cells Expression and Activity in Electroporated Tobacco Protoplasts In order to test the expression and enzymatic activity of the cloned E. coli biosynthetic threonine deaminases in plant cells, several plant expression plasmids were constructed for transient expression in tobacco leaf protoplasts. The plant expression plasmids contain all the necessary elements for plant cell expression, including a promoter (i.e., e35S (Odell et al., 1985)), the 5' untrans-lated leader sequence within the e35 S promoter, a coding sequence, and a transcription termination and polyadenylation signal (i.e., E9 (Coruzzi et al., 1984)). The wild-type E. coli biosynthetic threonine deaminase (IlvA) encoded by the insert in pMON25663 (FIG. 13) and the three mutant, deregulated E. coli biosynthetic threonine deaminases encoded by the inserts in pMON25686 (FIG. 14), pMON25687 (FIG. 15), and pMON25688 (FIG. 16) containing the IlvA 219 (L447F), IlvA466 (L481F), and IlvA219/466 (L447F/L481F) mutations, respectively, were cloned downstream of the e35S constitutive plant promoter (Odell et al., 1985) and targeted to chloroplasts using a translational fusion to the Arabidopsis rubisco small subunit chloroplast transit peptide (ArabSSU1A; Stark et al., 1992). The four plasmids containing the various threonine deaminase-encoding DNAs were independently electroporated into tobacco leaf protoplasts by the method of Hinchee et al. (1994). Tobacco protoplasts electroporated with the various DNA's were sonicated to lyse the protoplasts. FIG. 17 shows the expression of the various IlvA enzymes determined by Western blot analysis using rabbit polyclonal antibodies generated to the wild-type IlvA. Enzyme activity was monitored in extracts of lysed protoplasts in the presence and absence of isoleucine as described above, and is reported in Table 4.

TABLE 4

Activity of Threonine Deaminases Introduced Into Tobacco Protoplasts

| Electroporated Plasmid | Threonine Deaminase Specific Activity, u/mg (%)[1] | |
|---|---|---|
| | 0 mM Isoleucine | 1 mM Isoleucine |
| no plasmid DNA | 0.000 | 0.000 |
| pMON25663 (wt IlvA) | 0.089 | 0.006 (6.7) |
| pMON25686 (IlvA 219 L447F) | 0.101 | 0.091 (90.1) |
| pMON25687 (IlvA 466 L481F) | 0.162 | 0.048 (29.6) |
| pMON25688 (IlvA 219/466 L447F/L481F) | 0.181 | 0.181 (100) |

[1]Rates were determined using 10 mM threonine as substrate, at the indicated concentrations of isoleucine. Values in parenthesis are % activity relative to the results with 0 mM isoleucine.

As shown in FIG. 17, the "no DNA" control tobacco protoplasts did not exhibit any immunoreactive bands corresponding to threonine deaminase by Western blotting. In contrast, extracts of lysed tobacco protoplasts into which plasmids pMON25663, pMON25686, pMON25687, and pMON25688 were electroporated contained immunoreactive bands corresponding to the predicted molecular weight of the threonine deaminase encoded by the inserts of the respective plasmids. The enzymatic activity data reported in Table 4 demonstrate that both wild-type and deregulated threonine deaminases exhibit their predicted isoleucine deregulated enzymatic activities when expressed in plant cells based upon the results reported in the section entitled "Biochemical Analysis of Wild-type and Mutant E. coli Threonine Deaminases" of Example 2.

Expression and Activity in Transformed Soybean Callus

As shown above, the E. coli IlvA proteins can be functionally expressed in a plant transient expression system. In order to test the expression of a biosynthetic threonine deaminase in a stably transformed plant tissue, non-differentiating callus derived from soybean hypocotyl tissue was transformed with a plasmid containing the E. coli wild-type ilvA threonine deaminase gene using Agrobacterium tumefaciens ABI (Koncz and Schell, 1986).

Transformation Vector

Figure 18:
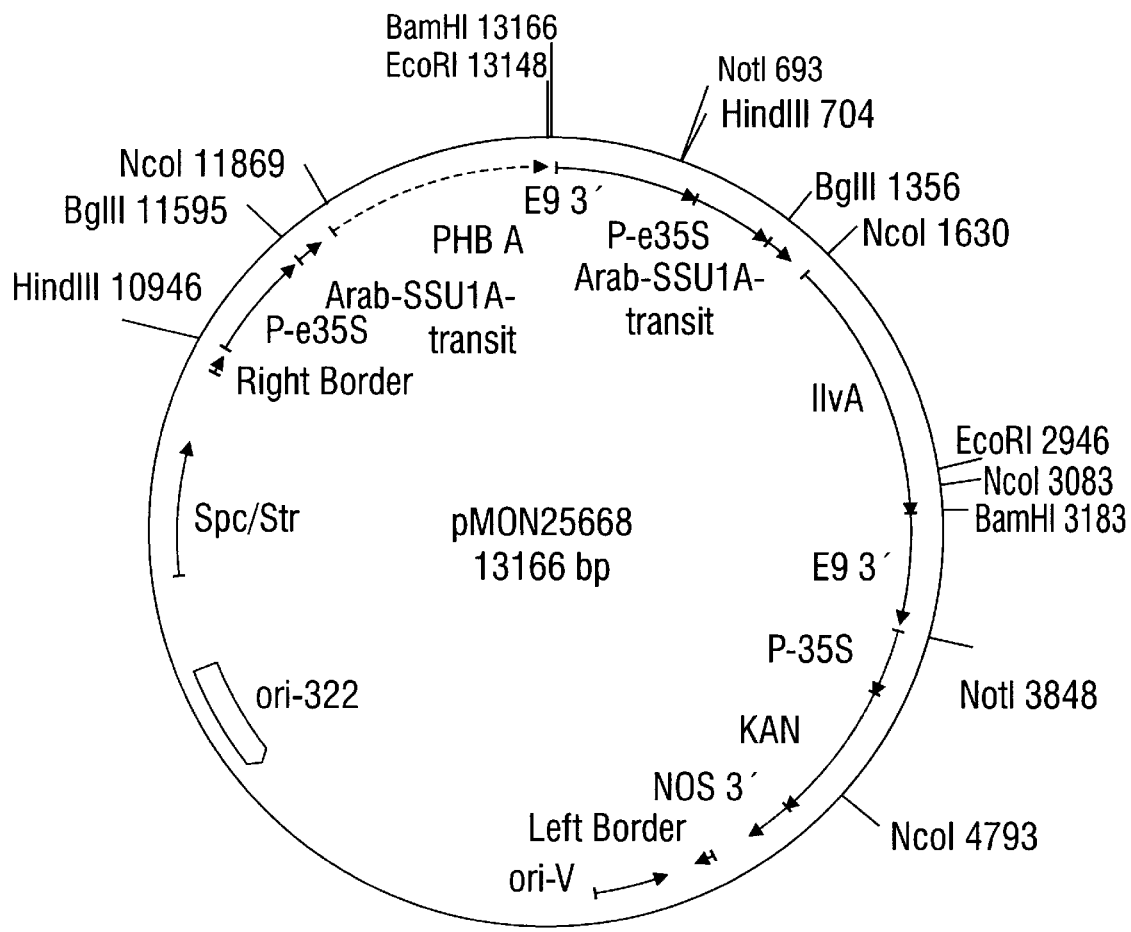
FIG. 18 shows the structure of pMON25668. pMON25668 is the Agrobacterium plant transformation plasmid used to test expression of the wild-type E. coli threonine deaminase (IlvA) in soybean callus. The phbA gene on plasmid pMON25668 was not required for the expression of threonine deamninase.

Soybean callus tissue was transformed with binary Ti plasmid pMON25668 (FIG. 18). Plasmid pMON25668 contains the e35S-expressed, plastid-targeted (ARABSSU1A) E. coli wild-type ilvA threonine deaminase gene, the e35S-expressed, plastid-targeted (ARABSSU1A) A. eutrophus phbA (β-ketothiolase) gene, and the e35s-expressed neomycin phosphotransferase type II (NptII) gene for kanamycin resistance. pMON26668 contains two border sequences for T-DNA transfer into the plant chromosome. The right border sequence is the only border required for T-DNA transfer into the plant; however, including the left border sequence terminates T-DNA integration at that point, thereby limiting the unnecessary incorporation of "extra" DNA sequences into the plant chromosome. pMON25668 also contains the minimun sequence of ori-322 for replication and maintence in E. coli as well as ori-V of the broad host origin RK2 for replication in Agrobacterium. TrfA is supplied in trans for proper replication in Agrobacterium. Further details of these vectors can be found in Glick et al., (1993) and the references cited therein.

Seedling Growth

The bottom of a 100×25 mm Petri dish was covered with Asgrow A3237 soybean seeds and the lid was replaced. Four Petri dishes containing seeds were placed inside a vacuum bubble containing a glass beaker holding 200 mls of Chlorox (sodium hypochlorite). The bubble was placed in a chemical fume hood. Two mls of HCl were added to the Chlorox, and the bubble lid was placed on quickly. A vacuum was pulled just long enough for the lid to stay on tightly, and the seeds were exposed to the resulting fumes overnight. The following day, the Petri dishes were removed from the bubble, and dry Captan (⅛ tsp) was added to each dish. The seeds were covered with sterile water and incubated in the Captan slurry for 5–7 minutes, after which the Captan slurry was removed.

After pipetting off the liquid from all of the plates, the seeds (20–25 per plate) were placed on 0.8% water agar plates. Only good quality seeds were chosen, i.e., no seeds with cracked seedcoats, discoloration, or other damage were used. Five plate high stacks of Petri plates were then wrapped with a rubberband, covered with a clear plastic bag, and incubated in a warm room set at 25° C. under continuous cool white light (60 $\mu$En m$^{-2}$s$^{-1}$; this can range from about 20–80 $\mu$En m$^{-2}$s$^{-1}$) for 6 days to obtain seedlings.

Preparation of Agrobacterium

About one week prior to inoculation, Agrobacterium tumefaciens ABI was streaked from a glycerol stock onto LB agar-solidified plates (1.5% agar) containing 100 mg/l spectinomycin, 50 mg/l kanamycin, and 25 mg/l chloramphenicol, and grown at room temperature.

The day before explant inoculation, Agrobacterium cultures were started in clear plastic tubes containing 2 mls of YEP (Sambrook et al., 1989) containing the same levels of spectinomycin, kanamycin, and chloramphenicol as above. About ¼ loopful of bacteria was placed in each YEP tube. The tubes were placed on a rotator in a warm room set at 25° C. Eight hours later, each 2 ml culture was added to 25 mls liquid YEP containing the same amounts of antibiotics as above, as well as 200 $\mu$M acetosyringone and 1 mM galacturonic acid, in a sterile 250 ml flask. The cultures were grown overnight in the dark at 28° C. with shaking (170 rpm).

On the day of explant inoculation, 12 ml aliquots of Agrobacterium were placed in sterile 50 ml centrifuge tubes. The tubes were centrifuged for 12 minutes at 2,000 rpm in order to pellet the cells. The supernatants were poured off and the pellets were resuspended in 20 mls of co-culture medium containing 1/10 MS salts and 1/10 B5 vitamins (Sigma, M 0404) and 15 g/l glucose, 20 mM MES, pH 5.4, and combined. The cell density was adjusted to a final OD$_{660}$ in the range from 0.3–0.35 from an initial OD$_{660}$ of 0.5–0.6. Thirty mls of this Agrobacterium suspension were used to inoculate each batch of 50 hypocotyl explants.

Explant Inoculation and Co-culturing

One day prior to explant inoculation, the plates containing the 6 day old seedlings were taken from the warm room and placed in a refrigerator at 0–10° C. (average temperature of 4° C.) for approximately 24 hrs. On the day of explant inoculation, the stacks of seedlings were taken from the cold one at a time just prior to explanting to maintain coldness. The hypocotyls were cut into 5 mm sections, and batches of 50 sections were inoculated by incubating them with 30 mls of Agrobacterium suspension in a Petri plate (100×25 mm) for 30 min. After 30 min, the Agrobacterium suspension was pipetted off. The explants were blotted on sterile qualitative Whatman filter paper, and then placed 10 per plate in 100×15 mm Petri plates containing one 8.5 cm sheet of sterile Whatman filter paper and 4 mls/plate of liquid co-culture medium containing 1/10 MS salts and 1/10 B5 vitamins, 15 g/l glucose, 3.9 g/l MES, 4.68 mg/l naphthaleneacetic acid (this can range from about 1–8 mg/l), 2.5 mg/l kinetin (this can range from about 0.5–4 mg/l), 200 $\mu$M acetosryingone (this can range from about 50–300 $\mu$M), and 1 mM galacturonic acid (this can range from about 0.1–2 mM), at pH 5.4. The plates were wrapped with parafilm and incubated for two days in a warm room set at 25° C. under continuous cool white light (40 $\mu$En m$^{-2}$s$^{-1}$; this can range from about 20–60 $\mu$En m$^{-2}$s$^{-1}$).

Selection

After the two day co-culture period, the explants were placed 10 per plate onto solid selection medium containing 1× MS salts and 1× B5 vitamins (Sigma, M 0404), 3% sucrose (this can range from about 1–6%), 4.68 mg/l naphthalene- acetic acid (this can range from about 1–8 mg/l), 2.15 mg/l kinetin (this can range from about 0.5–4 mg/l), 500 mg/l ticarcillin (this can range from about 25–250 mg/l), 100 mg/l kanamycin (this can range from about 25–250 mg/l), and 0.7% purified agar (Sigma, B 11853), at pH 5.7. The plates were wrapped with white 3M filter tape and cultured in a warm room set at 25° C. under continuous cool white light (40 μEn m$^{-2}$s$^{-1}$; this can range from about 20–60 μEn m$^{-2}$s$^{-1}$). Explants were transferred to fresh medium every two weeks. At the six week timepoint, the calli were excised from the hypocotyls and again transferred to the same selection medium for an additional two weeks. All calli were maintained on this selection medium until they were ready for assaying at 10–16 weeks.

Kanamycin-resistant calli were analyzed by Western blotting and enzymatic assays as described above to determine if *E. coli* IlvA was expressed and exhibited enzymatic activity in stably transformed soybean cells. The results are shown in FIG. 19.

Figure 19:
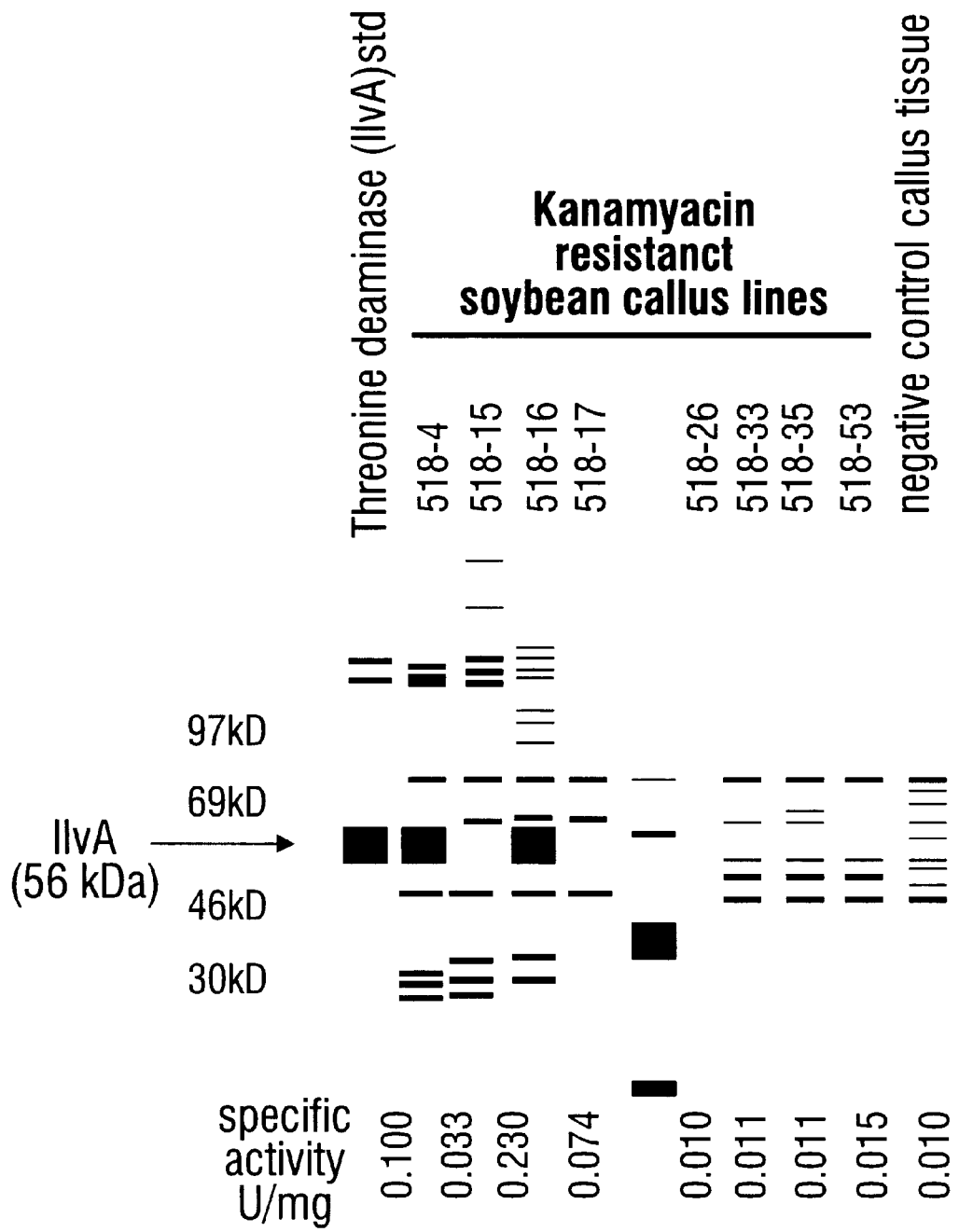
FIG. 19 shows the expression and activity of wild-type E. coli biosynthetic threonine deaminase in transformed soybean callus.

The data in FIG. 19 demonstrate that in four transformed calli (i.e., 518-4, 518-15, 518-16, and 518-17), the *E. coli* IlvA biosynthetic threonine deaminase was detectable by Western blot analysis. Enzymatic activity of the IlvA was also confirmed in the same transformed calli, correlating with the positive Western events. These results demonstrate that the *E. coli* IlvA can be expressed and maintain enzymatic activity in stably transformed plant tissue.

Colau et al., (1987) expressed the *S. cerevisiae* wild-type Ilvl gene in tobacco (*N. plumbaginifolia*) mutants deficient in threonine deaminase. Expression of this threonine deaminase in these mutants was sufficient to complement the isoleucine auxotrophy.

EXAMPLE 6

Increased Propionyl-CoA Production From α-Ketobutyrate Via Modification of the Pyruvate Dehydrogenase Complex or Expression of a Branched-Chain α-Ketoacid Dehydrogenase Complex As demonstrated for the bacterial (Danchin et al., 1984; Bisswanger, 1981) and pea chloroplast complexes (Camp et al., 1988; Camp and Randall, 1985), pyruvate dehydrogenase complex (PDC) catalyzes the oxidative decarboxylation of α-ketobutyrate to produce propionyl-CoA (FIG. 3). The rates of turnover of α-ketobutyrate with both the bacterial and chloroplast PDCs are approximately 10% of that relative to pyruvate at 1.5 mM concentration of α-ketoacid. The effect on kinetic constants with the bacterial enzyme is a 10-fold increase in $K_m$, and a five-fold decrease in $V_{max}$ (Bisswanger, 1981). Therefore, if steady-state concentrations of α-ketobutyrate rise to high μM or low mM levels, turnover of α-ketobutyrate to propionyl-CoA catalyzed by the pyruvate dehydrogenase complex should occur in plants and bacteria. Van Dyk and LaRossa (1987) demonstrated in wild-type *Salmonella typhimurium*, under conditions where acetohydroxyacid synthase (AHAS, FIG. 3) activity is reduced by inhibition with sulfometuron methyl, that the concentration of α-ketobutyrate increases significantly, and propionyl-CoA accumulates (acetohydroxyacid synthase condenses α-ketobutyrate and pyruvate to produce 2-aceto-2-hydroxy isovalerate as the second step in the biosynthesis of isoleucine, see FIG. 3). With respect to the P(3HB-co-3HV) copolymer biosynthetic pathway depicted in FIG. 3 and as discussed in Examples 2–4 above, high levels of α-ketobutyrate produced by the overexpression of a deregulated threonine deaminase should be sufficient for propionyl-CoA formation, even when there is competing demand for the α-ketoacid in isoleucine biosynthesis. Results presented in Table 3 demonstrating elevated levels of α-ketobutyrate in vivo from the presence of a deregulated threonine deaminase support this hypothesis.

The pyruvate dehydrogenase complex is a multienzyme complex that contains three activities: a pyruvate decarboxylase (E1), a dihydrolipoyl transacetylase (E2), and a dihydrolipoyl dehydrogenase (E3). Other α-ketoacid dehydrogenase complexes exist that use the same catalytic scheme with α-ketoacids other than pyruvate. The TCA cycle α-ketoglutarate dehydrogenase complex is an example. The branched-chain α-ketoacid dehydrogenases are also multienzyme complexes constructed in a manner similar to that of the pyruvate dehydrogenase complex. If the endogenous pyruvate dehydrogenase complex is not sufficiently active in catalyzing the turnover of α-ketobutyrate to propionyl-CoA for copolymer production, it can be modified to enhance its activity.

One way to accomplish this, for example, is to overexpress a branched-chain α-ketoacid decarboxylase E1 subunit having better binding and decarboxylating properties with α-ketobutyrate than does the native PDC E1. For example, the branched chain α-ketoacid dehydrogenase complex of bovine kidney has substantial activity with α-ketobutyrate as substrate, comparable to that with the normal substrate α-ketoisovalerate ($K_m$=56 μM and 40 μM, respectively; specific activity=12†μmol/min•mg, Pettit et al., 1978). Other examples of branched chain α-ketoacid dehydrogenase compleses are those from *Pseudomonas putida* (Burns et al, 1988), and *Bacillus subtilis* (Lowe et al, 1983). An overexpressed branched-chain α-ketoacid decarboxylase E1 subunit could effectively compete with the endogenous pyruvate dehydrogenase complex E1 subunit, and combine with the pyruvate dehydrogenase complex E2E3 subcomplex to create a functional hybrid complex. This has in fact been shown to occur naturally with the *E. coli* α-ketoglutarate dehydrogenase complex, where approximately 10% of the total E1 component is the pyruvate dehydrogenase complex E1 (Steginsky et al., 1985). The pyruvate dehydrogenase complex E1 component accounts for the pyruvate activity of the α-ketoglutarate dehydrogenase complex. An artificially produced hybrid of E1 (pyruvate decarboxylase) with E2E3 (dihydrolipoyl transsuccinylase-dihydrolipoyl dehydrogenase subcomplex) has higher turnover rates with pyruvate compared to the naturally isolated aketoglutarate dehydrogenase complex, but understandably lower rates than that of the pyruvate dehydrogenase complex itself (Steginsky et al., 1985).

Alternatively, both the E1 and E2 components of a branched-chain α-ketoacid dehydrogenase complex that has significant activity with α-keto-butyrate, such as the bovine kidney complex mentioned above, can be expressed. Since the dihydrolipoyl dehydrogenase (E3) is common to all α-ketoacid dehydrogenase complexes, and would be naturally produced for the pyruvate dehydrogenase complex, overexpression of this component may not be necessary. The endproduct would be a fully functional, branched-chain α-keto-acid dehydrogenase complex. If additional E3 is required to interact with overexpressed and endogenous E1 and E2 components, one could overexpress a plant or bacterial E3 (Camp & Randall, 1985, and Camp et al., 1988), or the specific E3 of the branched-chain α-ketoacid dehydrogenase complex, for example the bovine kidney complex (Pettit et al., 1978).

In addition to an E1 α-ketoacid decarboxylase catalyzing the decarboxylation of an α-ketoacid in an intact complex, unassociated E1 in the presence of an oxidizing agent will catalyze the decarboxylation of an α-ketoacid to form $CO_2$ and the free acid (Gruys et al., 1989; Speckhard & Frey, 1975; Reed & Willms, 1966). Thus, it is possible that an unassociated branched-chain E1, such as that from bovine kidney, when overexpressed in plants or bacteria, will produce propionate and $CO_2$ from α-ketobutyrate in the presence of an endogenous oxidizing agent such as ferredoxin. Propionate can be activated to propionyl-CoA by endogenous or overexpressed acyl-CoA synthetase (refer to Example 7).

Mutagenesis of the endogenous E1 of the host PDC is another approach to enhancing its activity toward α-ketobutyrate. Recent reports of mutagenesis of the E2 component from Bacillus (Wallis & Perham, 1994), Azotobacter (Schulze et al., 1992 & 1993), and the human E3 component (Kim and Patel, 1992), have demonstrated that one can modify both the activity of these enzymes towards substrates as well as their binding affinity to the complex. Similar manipulations can be carried out on the E1 component to enhance its catalytic turnover of α-ketobutyrate.

EXAMPLE 7

Increased Propionyl-CoA Production From α-Ketobutyrate Via Overexpression of Pyruvate Oxidase and Acyl-CoA Synthetase Another method of enhancing the level of propionyl-CoA in bacteria and plants involves, in a first step, the oxidative decarboxylation of α-ketobutyrate (the amount of which can be increased in vivo by utilizing a deregulated threonine deaminase as described above in Examples 2–4), to propionate and $CO_2$, catalyzed by pyruvate oxidase (E.C. 1.2.3.3) (FIG. 3). Unpublished results have shown that pyruvate oxidase efficiently catalyzes this reaction (J. E. Cronan, University of Illinois, personal communication). The poxB gene of *E. coli* encodes the pyruvate oxidase enzyme (Grabau and Cronan, 1986). Another example is the pyruvate oxidase from *Lactobacillus plantarum* (Miller and Schulz 1993). This homotetrameric protein of 62 kDa has been thoroughly characterized (Chang & Cronan, 1995, and references cited therein).

In a second step following pyruvate oxidase, endogenous bacterial or plastid acyl-CoA synthetases such as acetyl-CoA synthetase will activate the free propionate to propionyl-CoA (Doi et al., 1986; Nakamura et al., 1991). Yeast acetyl-CoA synthetase has been shown to catalyze the activation of propionate to propionyl-CoA (Patel and Walt, 1987). In addition to yeast, the *A. eutrophus* acoE gene has been cloned and shown to be active with propionyl-CoA (Priefert and Steinbüchel, 1992). If the endogenous acetyl-CoA synthetase activity proves to be insufficient for producing propionyl-CoA, the enzyme, for example that from yeast, can be overexpressed in the plant, or in a bacterial host.

Another system for activating propionate to propionyl-CoA has been described by Rhie and Dennis (1995). In *E. coli*, the actions of acetate kinase (ackA) and phosphotransacetylase (pta) are predominately responsible for the conversion of propionate to propionyl-CoA. Thus acetyl-CoA synthetase can be replaced by acetate kinase (ackA) and phosphotransacetylase (pta) in the present invention.

Enhanced propionyl-CoA production can thus be achieved by overexpressing any of the foregoing enzymes in a plant or bacterial host. Overexpression of the foregoing enzymes in combination with an overexpressed deregulated threonine deaminase and overexpressed PHA β-ketothiolase, β-ketoacyl-CoA reductase, and PHA synthase enzymes is expected to result in the production of P(3HB-co-3HV) copolymer.

EXAMPLE 8

Optimization of β-Ketothiolase, β-Ketoacyl-CoA Reductase, and PHA Synthase Activity for Production of P(3HB-co-3HV) Copolymer in Bacteria and Plants

*Alcaligenes eutrophus* can produce both PHB homopolymer and, when provided with an appropriate precursor such as propionate, P(3HB-co-3HV) copolymer (U.S. Pat. No. 4,477,654). It was expected that P(3HB-co-3HV) copolymer would also be produced if *E. coli* transformed with the *A. eutrophus* PHB biosynthetic genes was provided with the appropriate precursor, for example, propionate or α-ketobutyrate (see FIG. 3).

The experiment reported in Table 3, supra, was designed in part to test this hypothesis. Introduction of a deregulated threonine deaminase (L481F) into *E. coli* was expected to provide α-ketobutyrate for incorporation of a C5 monomer into the PHA polymer. However, the data in Table 3 demonstrate that while the α-ketobutyrate concentration in cells containing the overexpressed threonine deaminase was dramatically elevated, PHA polymer content and composition were essentially identical in both wild-type cells and cells expressing the introduced threonine deaminase. These results suggest the presence of a metabolic block in the conversion of α-ketobutyrate to P(3HB-co-3HV) copolymer.

As shown in FIG. 3, there are four reactions required to convert α-ketobutyrate to P(3HB-co-3HV) copolymer. These reactions are catalyzed successively by the pyruvate dehydrogenase complex, β-ketothiolase, acetoacetyl-CoA reductase, and PHB synthase. The metabolic block may therefore involve the inability of one of these enzymes to utilize substrate derived from α-ketobutyrate. However, the literature suggests that all of these enzymes possess the appropriate substrate specificities (Bisswanger, 1981; Haywood et al., 1988a; Haywood et al, 1988b; Haywood et al, 1989). Thus, the substrate specificities of some of these enzymes were reevaluated.

Substrate Specificity of PhbB Acetoacetyl-CoA Reductase from *A. eutrophus* and β-Ketothiolases from Various Sources PhbB Acetoacetyl-CoA Reductase Analysis of *A. eutrophus* PhbB acetoacetyl-CoA reductase substrate specificity in the forward reaction was carried out using β-ketobutyryl-CoA (acetoacetyl-CoA) and β-ketovaleryl-CoA. These β-ketoacyl-CoAs were reduced to the corresponding D-β-hydroxyacyl-CoAs using NADPH (FIG. 1) This analysis was previously performed by Haywood et al. (1988a), but in the reverse reaction where in situ-generated D-β-hydroxyacyl-CoA was oxidized with $NADP^+$. It is important to establish that this enzyme can catalyze the forward reaction with bet β-ketovaleryl-CoA and NADPH to be confident that it does not represent a metabolic block in copolymer production.

*E. coli* transformed with plasmid pMON25628 (FIG. 20) encoding *A. eutrophus* PhbB acetoacetyl-CoA reductase were grown on LB to early log phase and induced with nalidixic acid (60 µg/ml). Protein extracts were obtained by pelleting induced cells, resuspending in 50 mM KPi and 5% glycerol, sonicating, and removing cellular debris by centrifugation. The assay was conducted at pH 7.0 with 100 mM KPi, 0.15 mM NADPH, and 60 μM β-ketoacyl-CoA. The reaction was initiated with acetoacetyl-CoA reductase. Synthesis of β-ketovaleryl-CoA was accomplished through a scaled-up version (10 μmol of acyl-CoA in 2 ml total volume) of the in situ-generated β-ketoacyl-CoA procedure described below in the section entitlted "Thiolysis Activity of A. eutrophus BktB." Purification was accomplished through semi-prep C8-reverse-phase HPLC using the following gradient per sample run (Buffer A is 100 mM ammonium acetate, pH 6.0, B is acetonitrile) with a 4.0 ml/min flow rate: 0–25 min, 5–45% B; 25–30 min, hold at 45% B; 30–32 min, 45–5% B; 32–42 min, hold at 5% B. β-ketovaleryl-CoA eluted and was collected from 8.5 to 10.5 min.

Rate results for β-ketobutyryl-CoA and β-ketovaleryl-CoA with PhbB acetoacetyl-CoA reductase gave specific activities of 103 and 28 units/mg protein, respectively, which is 27% relative rate for the C5 versus the C4 substrate under the conditions of the assay. This is consistent with the results described by Haywood et al. (1988a), but further demonstrates that this enzyme is catalytically sufficient for the metabolic conversion of β-ketovaleryl-CoA to D-β-hydroxyvaleryl-CoA in the production of copolymer.

β-Ketothiolases

Condensation Activity of A. eutrophus PhbA and BktB

The data presented above demonstrate that the substrate specificity of PhbB is sufficient for production of C5 monomer for incorporation into PHA. Therefore, the substrate specificity of PhbA, as well as of other A. eutrophus β-ketothiolases, was investigated.

As noted above, A. eutrophus can produce P(3HB-co-3HV) copolymer when provided with an appropriate C5 precursor. Slater et al. (1988) demonstrated the presence of genes other than phbA encoding β-ketothiolase activity in A. eutrophus. One of these β-ketothiolases, designated BktB herein, was encoded on plasmid pBK6. A. eutrophus BktB was obtained from E. coli DH5α transformed with plasmid pMON25754. pMON25754 was produced from the A. eutrophus pBK6 clone (Slater et al., 1988) by deleting a 5.0 kb XhoI fragment (there is an additional XhoI site approximately 5.0 kb 5' to the XhoI site shown in FIG. 1 of Slater et al.). The pBK6 clone was produced by Slater et al. (1988) from A. eutrophus H16, i.e., ATCC accession number 17699, which is publicly available from the American Type Culture Collection, 12301 Parklawn Drive, Rockville, Md. 20852. BktB was overexpressed from its native promoter on the high copy plasmid pMON25754 by growing the cells overnight at 37° C. to stationary phase in LB broth containing ampicillin (100 μg/ml). A. eutrophus PhbA was obtained from E. coli DH5α transformed with pMON25636 (FIG. 22) by growing the cells at 37° C. in LB broth containing ampicillin (100 μg/ml) to early log phase and then inducing with IPTG. Cells were harvested after two hours of further growth. PhbA and BktB protein extracts were prepared by pelleting the cells, resuspending in 50 mM KPi and 5% glycerol, sonicating, and removing cellular debris by centrifugation.

The activity of β-ketothiolases can be assayed in both the condensation and thiolysis directions. However, condensation activity for products that are the result of a mixed condensation of acetyl-CoA and a longer chain acyl-CoA are difficult to measure. This is due to the difficulty in distinguishing between acetoacetyl-CoA, the product of condensing two acetyl-CoA molecules, and the mixed condensation reaction product, both of which form simultaneously. To date, condensation assays have been spectrophotometrically-based, but these are valid only when there is a single acyl-CoA substrate present (i.e., acetyl-CoA) since they cannot discriminate between the products formed. The assay described below represents the first reported assay that permits complete quantitation of all condensation products regardless of the nature of starting substrates.

β-ketothiolase assays designed to measure the condensation activity with acetyl-CoA plus either propionyl-CoA or butyryl-CoA were performed using 1-$^{14}$C-labelled acetyl-CoA. Since the equilibrium for the reaction lies heavily toward the starting acyl-CoAs rather than the condensed β-ketoacyl-CoA product, the latter was "pulled" to the corresponding β-hydroxyacyl-CoA using NADH and β-ketoacyl-CoA dehydrogenase. In addition, to avoid the strong feedback inhibition of β-ketothiolase by free CoA, each assay solution contained 5,5'-dithio-bis(2-nitrobenzoic acid) (DTNB) to trap chemically the free CoA produced by the reaction.

The condensation assay mixture (0.5 ml final volume) contained 100 mM KPi, pH 7.8, 0.5 mM NADH, 0.30 mM 1-$^{14}$C-acetyl-CoA (0.15 μCi), 5 units β-ketoacyl-CoA dehydrogenase, 0.5 mM DTNB, and variable propionyl- or butyryl-CoA as indicated in Table 5. The reaction was initiated by the addition of β-ketothiolase. Following 20 minutes at 30° C., each reaction mixture was quenched by the addition of 25 μl of 10% formic acid. Thirty μl of 25% H$_2$SO$_4$ were added to 200 μl of quenched reaction mix; this mixture was then incubated at 70° C. for 24 hours to hydrolyze all CoA thioesters to their free acids. Sixty μl of 5 M sodium formate were added to the sample to neutralize the pH, followed by analysis of a 130 μl aliquot using C18-reverse-phase HPLC (0.5×25 cm column). Detection and quantitation were carried out by monitoring flow-through with a Radiomatic flow detector. A gradient elution was employed using aqueous 1% acetic acid (solvent A) and acetonitrile (solvent B). The following gradient program was used per sample run with a flow rate of 1.0 ml/min: 0–15 min, 0–35% B; 15–20 min hold at 35% B; 20–21 min, 35–0% B; 21–30 min hold at 0% B. Retention times for $^{14}$C-labelled compounds are as follows; acetic acid, 5.1 min; β-hydroxybutyric acid, 7.5 min; β-hydroxyvaleric acid, 11.7 min; and β-hydroxycaproic acid, 15.3 min. Calculation of the percent turnover of 1-$^{14}$C-acetyl-CoA to product was based on the $^{14}$C-peak integration, correcting for the double label which occurs in β-hydroxybutyric acid (i.e., from two molecules of 1-$^{14}$C-acetyl-CoA). The results are shown in Table 5.

TABLE 5

Substrate Specificity of A. eutrophus PhbA and BktB
β-Ketothiolases in the Condensation Reaction
with Acetyl-CoA plus Propionyl-CoA or Butyryl-CoA[1]

| Enzyme Sample | Propionyl-CoA (mM) | % Turnover C4 Product | % Turnover C5 Product | % Turnover C6 Product |
|---|---|---|---|---|
| PhbA | 0 | 16.9 | | |
| PhbA | 0.6 | 13.5 | 0 | |
| PhbA | 1.2 | 10.3 | 0 | |
| PhbA | 2.4 | 7.0 | 0 | |
| BktB | 0 | 4.2 | | |
| BktB | 0.6 | 1.8 | 13.2 | |
| BktB | 1.2 | 1.0 | 15.6 | |
| BktB | 2.4 | 0.7 | 17.8 | |

TABLE 5-continued

Substrate Specificity of *A. eutrophus* PhbA and BktB
β-Ketothiolases in the Condensation Reaction
with Acetyl-CoA plus Propionyl-CoA or Butyryl-CoA[1]

| Enzyme Sample | Propionyl-CoA (mM) | % Turnover C4 Product | % Turnover C5 Product | % Turnover C6 Product |
|---|---|---|---|---|
| | Butyryl-CoA (mM) | | | |
| BktB | 0.6 | 1.0 | | 4.9 |
| BktB | 1.2 | 0.6 | | 7.3 |
| BktB | 2.4 | 0.4 | | 7.9 |

[1]For all reactions, the acetyl-CoA concentration was 0.30 mM (0.15 μCi $^{14}$C-acetyl-CoA per 0.50 ml reaction). The concentration of propionyl-CoA or butyryl-CoA refers to the concentration in the assay. % turnover to product refers to the amount of acetyl-CoA converted to C4, C5, or C6 product. PhbA β-ketothiolase was not tested for C6 product formation with butyryl-CoA. Blank spaces indicate products that were not detected in the experiment, probably because the appropriate acyl-CoAs were not present in the individual reaction mixture.

The data in Table 5 clearly demonstrate that the β-ketothiolase activity of PhbA is restricted to the catalytic formation of the C4 compound acetoacetyl-CoA. These results can explain the metabolic block to P(3HB-co-3HV) copolymer production in recombinant *E. coli* containing phbA, is phbB, phbC and *E. coli* ilvA466 (L481F) (Table 3). The data in Table 5 for *A. eutrophus* PhbA contrast with the suggestions of Haywood et al. (1988b) that propose, based on thiolysis data, that the activity of PhbA β-ketothiolase alone can account for the β-ketovaleryl-CoA needed for the C5 component in P(3HB-co-3HV) copolymer production. The data presented herein demonstrate that PhbA cannot efficiently catalyze the formation of the C5 monomer. Thus, a β-ketothiolase other than PhbA appears to be involved in the production of P(3HB-co-3HV) copolymer in *A. eutrophus*.

As shown in Table 5, the *A. eutrophus* BktB enzyme catalyzes the production of C4, C5, and C6 β-ketoacyl-CoA compounds, with an apparent preference for the formation of the C5 product. These results suggest that the biochemical pathway of P(3HB-co-3HV) copolymer production in *A. eutrophus* involves the BktB β-ketothiolase and/or another β-ketothiolase capable of forming the C5 product. These results further suggest that the biosynthesis of significant amounts of P(3HB-co-3HV) copolymer in heterologous host bacteria and plants can be facilitated by the use of a β-ketothiolase having condensation substrate specificity similar or identical to that of BktB, i.e., being capable of condensing acetyl-CoA with propionyl-CoA to form β-ketovaleryl-CoA.

In addition to its ability to catalyze the formation of β-ketovaleryl-CoA, the BktB β-ketothiolase can also catalyze the formation of β-keto-caproyl-CoA (Table 5). Based on this observation, the BktB β-ketothiolase can also be utilized for the production of copolymers containing monomers ranging in size from C4 to C6. Although the condensing activity of the BktB β-ketothiolase beyond C6 has not been tested, it is possible that this enzyme can catalyze the formation of β-ketoacyl-CoA compounds greater than C6. It is likely that plant and bacterial cells containing BktB and also expressing appropriate β-ketoacyl-CoA reductases and PHA synthases capable of utilizing the range of β-ketoacyl-CoA substrates produced by BktB (for example, *Nocardia corallina* PHA synthase; Dennis, 1994) can produce copolymers containing monomer units ranging from C4 to C6, and possibly beyond. One example is a copolymer comprising β-hydroxy-butyrate (3HB) and β-hydroxycaproate (3HC), designated P(3HB-co-3HC) copolymer.

Thiolysis Activity of *A. eutrophus* BktB

To enhance further our understanding of the kinetic characteristics of BktB β-ketothiolase, a thorough kinetic analysis of the enzyme's thiolysis activity was conducted using purified protein. The assay to determine the kinetic parameters $K_m$ and $V_{max}$ for β-ketobutyryl-CoA (C4), β-ketovaleryl-CoA (C5), and β-ketocaproyl-CoA (C6), was performed at 25° C. by the in situ generation of the β-keto compounds from their corresponding trans-2,3-enoyl-CoAs essentially as described by Haywood et al. (1988). Utilization of variable substrate concentrations permitted the determination of the descriptive kinetic parameters of the β-ketothiolase. Kinetic rates were determined only at fixed substrate concentrations in the Haywood et al. communication.

Purified BktB protein was prepared by growing *E. coli* EE36 transformed with pMON25754 in LB broth containing ampicillin (100 μg/ml) overnight at 37° C. Cells were then harvested by centrifugation, and the pellet was resuspended in 50 mM KPi and 5% glycerol, sonicated, and the sonicate centrifuged to remove cellular debris. The cell extract was desalted using a PD-10 column (Pharmacia), and proteins resolved using a Pharmacia FPLC system and MonoQ anion-exchange column (Pharmacia). Buffer A was 10 mM Tris buffer, pH 7.8, plus 1 mM DTT; buffer B was buffer A plus 1 M KCl. The gradient was 0 to 10% B in 10 min, then to 35% B in 40 min. The flow rate was 1 ml/min, and the resolved proteins were collected at the rate of 1 ml/fraction. The BktB protein was found in fractions 20 to 27, with the maximum activity peak at fraction 23. Fraction 23 used for N-terminal sequencing was desalted, washed, and stored in 10 mM sodium bicarbonate using a Centricon-10 concentrator (Amicon, Inc.). Protein was found to be pure according to SDS-PAGE analysis, with an apparent molecular weight of 39.5 kD (data not shown). The enzyme was stored in 10 mM Tris-HCl, pH 7.8, 1 mM DTT, 50% glycerol at −20° C. Activity remained constant for a minimum of two months under these conditions.

The purified BktB β-ketothiolase was diluted to approximately 1 mg/ml in 10 mM Tris-HCl, pH 7.8, 50% glycerol. Two rabbits were boosted initially with 200 μg of purified protein in a total volume of 1 ml by Scientific Associates Inc. (St. Louis, Mo.). Bleeds after the first boost yielded polyclonal antibodies which produced a single immunoreactive band at approximately 45 kD on Western blots containing a range of dilutions of purified BktB. The detection limit of the antibodies was determined to be 1 ng. These antibodies can be used to detect proteins having similar immunoreactive properties to BktB β-ketothiolase, thus making it possible to detect ketothiolases having similar enzymatic activity to BktB in crude extracts.

The C5 and C6 enoyl-CoAs were synthesized according to Schulz (1974) and purified using semi-prep C8-reverse-phase HPLC as described above for β-ketovaleryl-CoA. β-ketobutyryl-CoA (acetoacetyl-CoA) was purchased from Sigma (St. Louis, Mo.). The assay mixture (1 ml final volume) contained 150 mM EPPS, pH 8.0, 50 mM $MgCl_2$, 1.5 mM pyruvate, 0.4 mM $NAD^+$, and a coupling enzyme cocktail of three units crotonase, five units β-hydroxyacyl-CoA dehydrogenase, and 10 units lactic dehydrogenase. The enoyl-CoA was added to this mixture and the absorbance at 304 nm was monitored until it reached a plateau (typically about 5 min). CoA was added to this mixture, followed by BktB β-ketothiolase to initiate the reaction. The decrease in absorbance at 304 nm due to the thiolysis of the β-ketoacyl-CoA was utilized as a direct measure of activity. Extinction coefficients to convert absorbance units to μmol of product were 19.5, 12.2, and 14.0 cm$^{-1}$mM$^{-1}$ for β-ketobutyryl-CoA, β-ketovaleryl-CoA, and β-ketocaproyl-CoA, respectively. β-ketoacyl-CoA concentration was varied from 5 to 80 μM (CoA was fixed at 200 μM), and CoA concentration was varied from 20 to 400 μM (β-ketocaproyl-CoA was fixed at 60 μM) for determining kinetic parameters for β-ketoacyl-CoA and CoA, respectively. Reaction rates were calculated in the steady-state within the first minute following initiation. All data were fitted to the normal Michaelis-Menten equation using a non-linear regression analysis. The results are shown in Table 6.

TABLE 6

Kinetic Parameters for BktB β-Ketothiolase in the Thiolysis Reaction

| Substrate | $K_m$ (μM) | $V_{max}$ (u/mg)[1] | $V_{max}/K_m$ |
|---|---|---|---|
| B-ketobutyryl-CoA[2] | 37 ± 3 | 122 ± 5 | 3.0 |
| B-ketovaleryl-CoA[2] | 15 ± 1 | 236 ± 8 | 16 |
| B-ketocaproyl-CoA[2] | 6.0 ± 0.7 | 103 ± 3 | 17 |
| CoA[3] | 53 ± 6 | 98 ± 3 | 1.8 |

[1]A unit, u, refers to μmol product formed per minute.
[2]Kinetic parameters were determined using a fixed concentration of CoA of 200 μM.
[3]Kinetic parameters were determined using a fixed concentration of β-keto-caproyl-CoA of 60 μM.

The results in Table 6 show that β-ketovaleryl-CoA can be turned over by BktB by about a factor of two faster than the other two substrates according to the $V_{max}$ values. This faster turnover is somewhat modulated by a higher $K_m$ compared to β-ketocaproyl-CoA. Overall, based on $V_{max}/K_m$, the enzyme utilizes C5 and C6 substrates about equivalently, whereas β-keto-butyryl-CoA is approximately five-fold less efficient in catalytic turnover. These results are consistent with the condensation data for BktB shown in Table 5. From this, and in combination with the condensation and thiolysis results on PhbA β-ketothiolase, one might hypothesize that gathering thiolysis data alone for a particular β-keto-thiolase would be sufficient to suggest the activity of the enzyme in the condensation direction. However, as shown below, this is not necessarily true.

Thiolysis and Condensation Activity of Other β-Ketothiolases

Two additional β-ketothiolases from *A. eutrophus* (cosmid clones AE65 and AE902; Slater et. al., 1988), plus two β-ketothiolases from *Zoogloea ramigera*, were analyzed for thiolysis and condensation activity using the assays described above. *Zoogloea ramigera* (ATCC 19623) was grown at 30° C. for 48 hours in medium containing; 9.4 g/l K$_2$HPO$_4$; 2.2 g/l K H$_2$PO$_4$; 2.5 g/l MgSO$_4$•7H$_2$O; 3 g/l N-Z Amine; and 10 g/l Na-gluconate. *E. coli* containing cosmid clones AE65 and AE902 were grown for 16 hours at 37° C. in LB supplemented with 50 μg/ml kanamycin. For the thiolysis assay, activity was monitored at a fixed concentration of β-ketoacyl-CoA at 40 μM and CoA at 100 μM. All of the protein extracts were partially purified using the Pharmacia FPLC MonoQ separation described above. Table 7 shows the thiolysis results.

TABLE 7

Substrate Specificity of Various β-Ketothiolases in the Thiolysis Reaction[1]

| Enzyme Sample | β-keto-butyryl-CoA (u/mg) | β-keto-valeryl-CoA (u/mg) | β-keto-caproyl-CoA (u/mg) |
|---|---|---|---|
| Z. ramigera (A)[2] | 0.41 | 0.15 | 0.02 |
| Z. ramigera (B)[2] | 0.21 | 0.19 | 0.11 |
| pAE65 | 0.156 | 0.502 | 3.16 |
| pAE902 | 0.585 | 1.25 | 0.561 |

[1]Activity was determined using partially purified enzymes. The concentration of substrate was 40 μM. pAE designations are *A. eutrophus* cosmid clones.
[2]The *Z. ramigera* protein sample yielded two active ketothiolase peaks upon FPLC MonoQ resolution, designated A and B.

MonoQ separation of the *Z. ramigera* protein extract resulted in two resolved active β-ketothiolase peaks. The first peak, designated A, shows thiolysis activity with C4 and C5 substrate, but little if any with C6. Based on this activity, this β-ketothiolase in all likelihood is the enzyme purified and described by Davis et al., (1987), and is the protein expressed specifically for PHB production in this organism. *Z. ramigera* peak B, which has not been previously described, appears to have broadened specificity, at least to C6.

*A. eutrophus* cosmid clones pAE65 and pAE902, when similarly analyzed for thiolysis activity, both showed specificity at least to C6. Clone pAE65, in fact, likely has significant activity with β-ketoacyl-CoAs of higher chain-length then C6 based on the significant increase in activity when going from C4 to C6. Additional results (not shown) for pAE65 demonstrate dehydratase and β-keto-acyl-CoA dehydrogenase activity in the same resolved MonoQ fraction. This suggests that the pAE65 clone contains the genes for the fatty acid β-oxidative complex proteins of *A. eutrophus*. Interestingly, clone pAE902 encodes an enzyme having thiolysis activity with β-ketoacyl-CoA substrates ranging from C4 to C6 similar to that of BktB. As such, considering only the tholysis results in Table 7, pAE902 might be considered a good candidate for β-ketovaleryl-CoA condensation production from acetyl-CoA and propionyl-CoA. However, it is important to consider condensation direction activity as well. Condensation results for this clone, along with that of the other β-ketothiolases, are shown in Table 8.

TABLE 8

Substrate Specificity of Various β-Ketothiolases in the Condensation Reaction with Acetyl-CoA Plus Propionyl-CoA or Butyryl-CoA

| Enzyme Sample | Substrates[1] | % Turnover C4 Product | % Turnover C5 Product | % Turnover C6 Product |
|---|---|---|---|---|
| Z. ramigera (A)[2] | C2 | 23.3 | | |
| Z. ramigera (A)[2] | C2 + C3 | 12.4 | 7.1 | |
| Z. ramigera (A)[2] | C2 + C4 | 18.9 | | 0 |
| Z. ramigera (B)[2] | C2 | 3.4 | | |
| Z. ramigera (B)[2] | C2 + C3 | 1.1 | 2.7 | |
| Z. ramigera (B)[2] | C2 + C4 | 1.2 | | 2.6 |
| pAE65 | C2 | 5.7 | | |
| pAE65 | C2 + C3 | 2.2 | 58.6 | |
| pAE65 | C2 + C4 | 0.5 | | 84.3 |
| pAE902 | C2 | 0 | | |

TABLE 8-continued

Substrate Specificity of Various
β-Ketothiolases in the Condensation Reaction with Acetyl-
CoA Plus Propionyl-CoA or Butyryl-CoA

| Enzyme Sample | Sub-strates[1] | % Turnover C4 Product | % Turnover C5 Product | % Turnover C6 Product |
|---|---|---|---|---|
| pAE902 | C2 + C3 | 0 | 0 | |
| pAE902 | C2 + C4 | 0 | | 0 |

[1]For all reactions, the acetyl-CoA (C2) concentration was 0.40 mM (0.15 μCi $^{14}$C-acetyl-CoA per 0.50 ml reaction). The concentration of propionyl-CoA (C3) or butyryl-CoA (C4) was 2.0 mM when present. % turnover to product refers to the amount of acetyl-CoA converted to C4, C5, or C6 product. pAE designations are *A. eutrophus* cosmid clones.
[2]The *Z. ramigera* protein sample yielded two active ketothiolase peaks upon FPLC Mono-Q resolution, designated A and B.

The data presented in Table 8 demonstrate condensation activity for all samples tested, excluding pAE902. Consistent with the pattern shown in the thiolysis results, the *Z. ramigera* enzymes are capable of producing C5, and C5 and C6 condensation products, for peaks A and B, respectively. These then represent two possible alternative candidates for use in the biosynthesis of P(3HB-co-3HV) copolymer in recombinant systems. Similarly, cosmid clone pAE65 shows activity that parallels that seen in the thiolysis assay.

The pAE902 cosmid clone showed no condensation products, and in addition exhibited greater than 50% hydrolysis of the starting $^{14}$C-acetyl-CoA in the time-course of the reaction (hydrolysis data not shown). This result shows that it is important to demonstrate condensation substrate specificity activity for a particular β-ketothiolase to evaluate whether or not it is useful in producing P(3HB-Co-3HV) copolymer. That is, from this result with pAE902, it is not obvious that the thiolysis activity of a particular β-ketothiolase will necessarily translate to useful information regarding its condensation activity. This also demonstrates the utility of a quantitative assay such as the one described herein for measuring condensation activity.

Cloning of the *A. eutrophus* bktB Gene

As noted above, Slater et. al. (1988) identified several putative *A. eutrophus* β-ketothiolase clones, including pBK6, by screening *E. coli* harboring an *A. eutrophus* cosmid library for β-ketothiolase activity.

The β-ketothiolase gene encoded on pBK6 was mapped by serial subcloning and deletion analysis, and sequenced (Sambrook et al., 1989). The sequence is shown in SEQ ID NO:9. For the purpose of the present invention, this gene has been designated as the bktB gene of *A. eutrophus*. This gene was deposited under the terms of the Budapest Treaty in the American Type Culture Collection, 12301 Parklawn Drive, Rockville, Md. 20852, U.S.A., as an insert in plasmid pMON25728 contained in *E. coli* DH5α on Mar. 6, 1996, designated ATCC 98007.

pMON25728 contains a fragment of approximately 3.9 Kb extending from a Bgl II site approximately 550 bp upstream of the bktB open reading frame to a Nco I site downstream of bktB. There is a single additional Nco I site in this fragment, and it is within bktB. The Bgl II site upstream of bktB is the single Bgl II site shown in plasmid pBK6 (Slater et al, 1988). pMON25728 contains the 3.9 Kb Bgl II-NcoI fragment in which both sites have been end-filled and ligated to DNA of pBluescipt KS+ (Stratagene). pBluescript KS+ polylinker sites were cut with Sac I and Eco RV, and the Sac I site was treated with exonuclease to create a blunt end. The Bgl II site of the *A. eutrophus* DNA has been fused to the EcoRV site of pBluescript KS+.

Automated Edman degradation chemistry was used to determine the NH$_2$-terminal protein sequence (Hunkapiller et al., 1983) of purified BktB protein. A Perkin Elmer Applied Biosystems Division sequencer (Foster City, Calif.) was employed for the analysis. The respective PTH-aa derivatives were identified by RP-HPLC analysis in an on-line fashion employing a Brownlee 2.1 mm I.D. PTH-C18 column.

Amino acid sequencing of the protein purified (0.9 mg/ml) as described above revealed that the N-terminal sequence minus the initiating methionine (TREVVVVSGVRTAIG, SEQ ID NO:10) corresponds to that predicted by the DNA sequence shown in SEQ ID NO:9, as well as the deduced amino acid sequence shown in SEQ ID NO: 11.

P(3HB-co-3HV) Copolymer Production and Active Expression of bktB in *E. coli*

The data reported in Table 3 (Example 2) suggested the presence of a metabolic block to P(3HB-co-3HV) copolymer production in *E. coli* transformed with the *A. eutrophus* phbA, phbB, phbC, and *E. coli* ilvA466 (L481F) genes. To determine whether the expression of the *A. eutrophus* bktB gene in *E. coli* is catalytically effective in P(3HB-co-3HV) copolymer biosynthesis in vivo, the following experiment was performed.

Two sets of *E. coli* DH5α cells were transformed with the plasmid combinations shown in Table 9 as described in Example 2 in the section entitled "In vivo Analysis of Cloned *E. coli* ilvA genes":

TABLE 9

Plasmid Combinations Used for the Production of
P(3HB-co-3HV) Copolymer in Transformed *E. coli*

| | Gene | Antibiotic resistance | Promoter | Origin of replication |
|---|---|---|---|---|
| Set 1 | | | | |
| pMON25628 | phbB | Spectinomycin | recA | ori327 |
| pMON25629 | phbC | Kanamycin | tac | ori pACYC |
| pMON25636 | phbA | Ampicillin | tac | ori CoLE1 |
| Set 2 | | | | |
| pMON25628 | phbB | Spectinomycin | recA | ori327 |
| pMON25629 | phbC | Kanamycin | tac | ori pACYC |
| pMON25728 | bktB | Ampicillin | native | ori CoLE1 |

Figure 20:
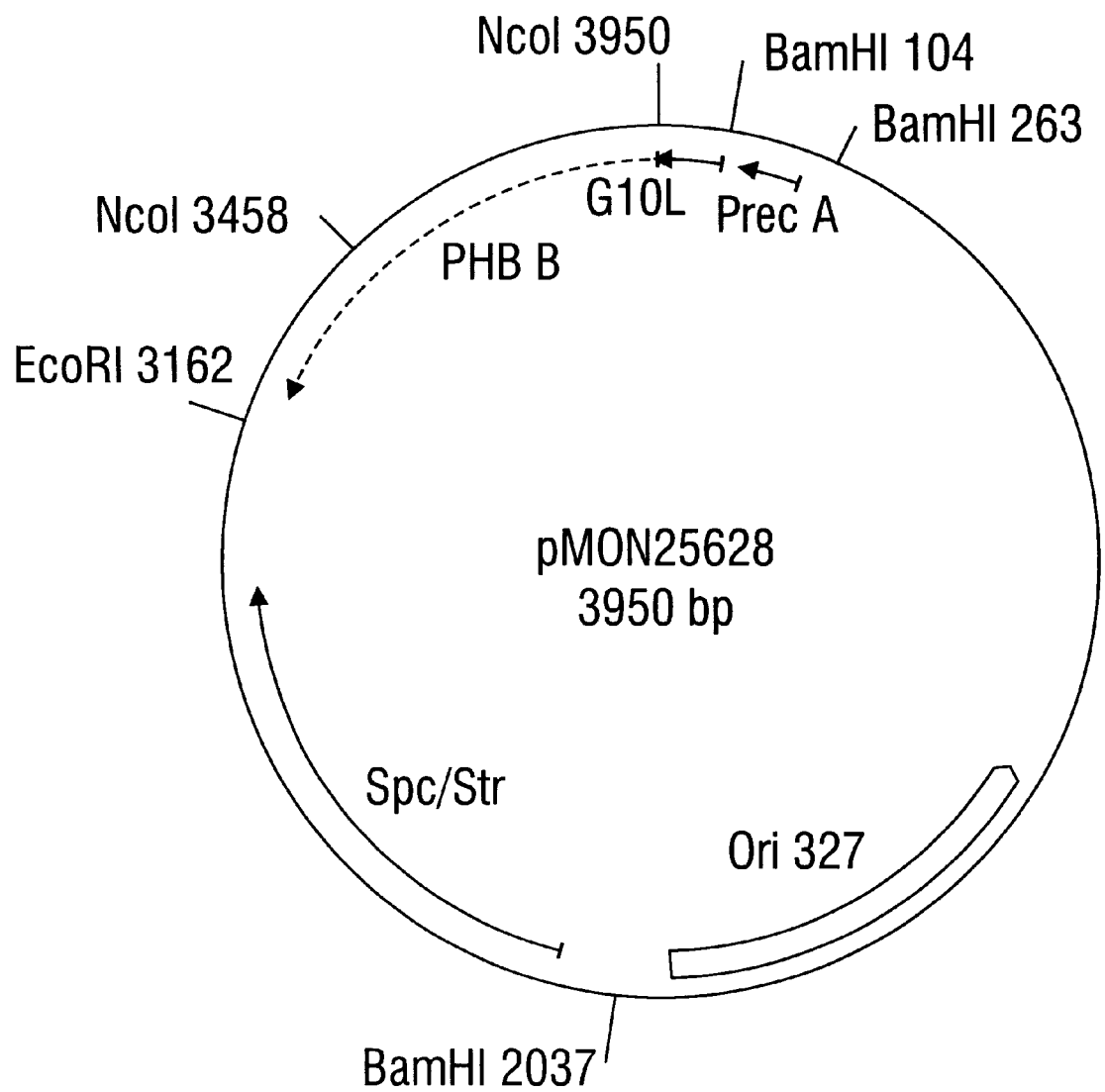
FIG. 20 shows the structure of pMON25628. pMON25628 was used for the overexpression in E. coli of the A. eutrophus PhbB reductase from the precA promoter.
Figure 21:
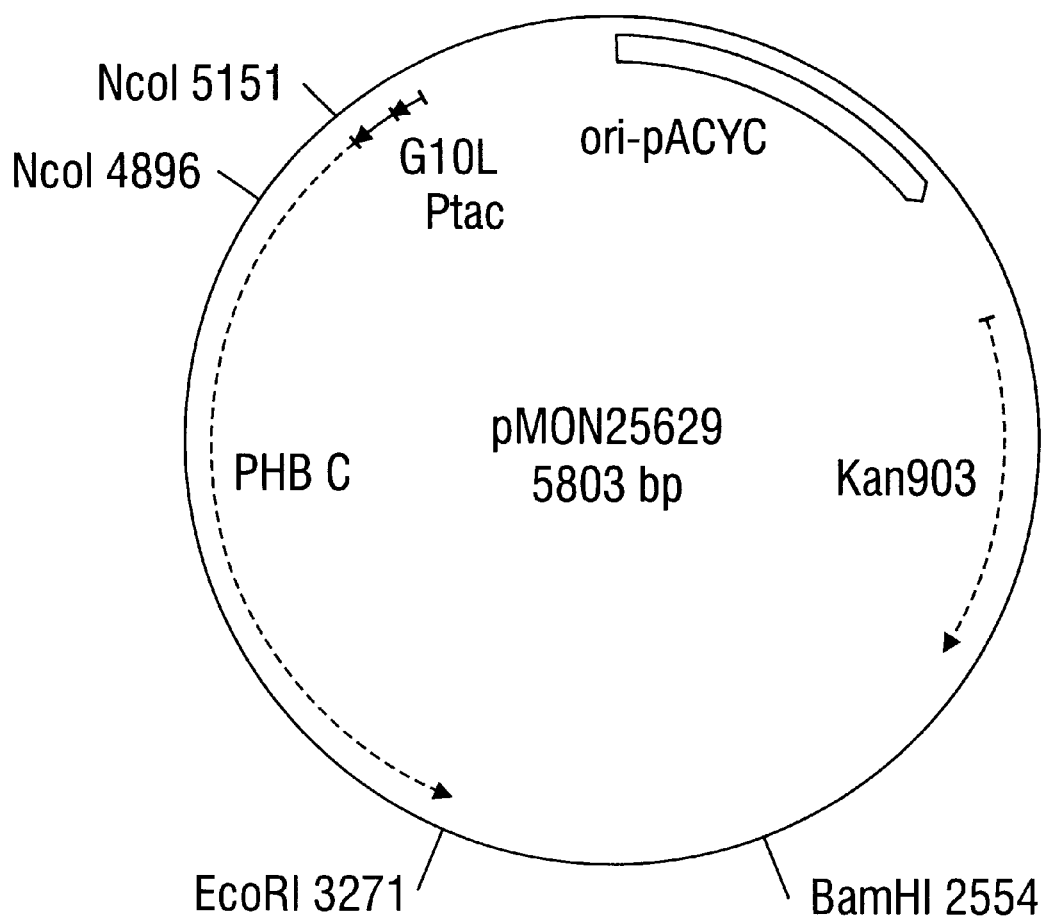
FIG. 21 shows the structure of pMON25629. pMON25629 was used for the overexpression in E. coli of the A. eutrophus PhbC synthase from the ptac promoter.
Figure 22:
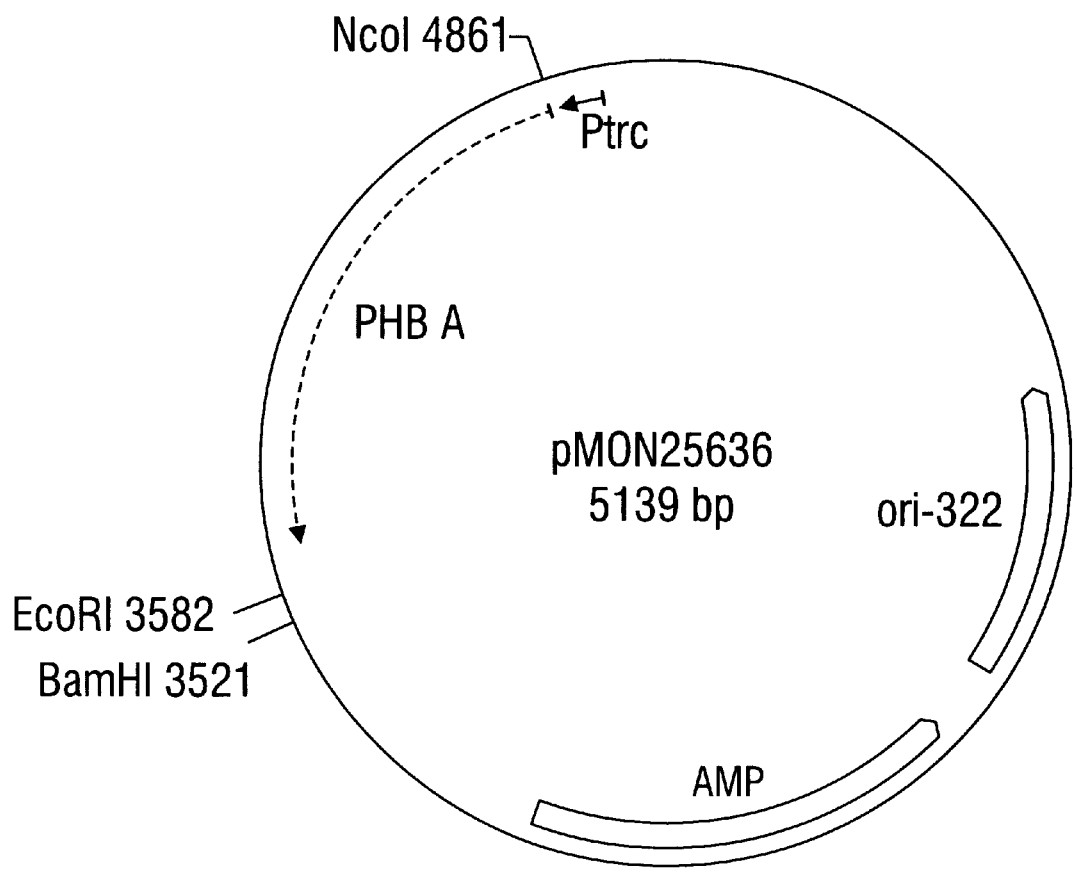
FIG. 22 shows the structure of pMON25636. pMON25636 was used for the overexpression in E. coli of the A. eutrophus PhbA β-keto-thiolase from the ptrc promoter.

Maps of pMON25628, pMON25629, and pMON25636 are shown in FIGS. 20–22, respectively. pMON25728, a derivative of pBK6 (Slater et al., 1988), was created by first subcloning a 5.5 Kb NotI/EcoRI fragment of pBK6 into pBluescript KS+ (Stratagene), creating pMON25722. pMON25722 was subsequently digested with BglII and EcoRI, releasing a 1.1 Kb fragment. The remaining vector was blunt ended with Klenow and religated, creating pMON25724. Finally, pMON25724 was partially digested with NcoI, and digested to completion with SacI, releasing a 0.9 Kb fragment. The remaining vector was blunt ended with Klenow and religated, creating pMON25728.

Each set of transformed cells containing all three plasmids was selected by the addition of all three antibiotics (ampicillin, 100 μg/ml; kanamycin, 50 μg/ml; spectinomycin, 75 μg/ml) to the growth medium (LB agar). Single isolated colonies were grown on LB medium containing all three antibiotics to early log phase and induced with IPTG and nalidixic acid. Cells were pelleted by centrifugation, resuspended in 500 μl of 50 mM KPi/5% glycerol, and sonicated on ice. Enzyme assays as described above were performed on the selected cells to confirm expression and activity of the reductase (PhbB), and, in the thiolysis direction, the β-ketothiolases (PhbA and BktB). The results are shown in Table 10.

TABLE 10

Activity of PhbA, BktB, and PhbB in Transformed *E. coli* DH5α

| | Gene | Thiolase Rate (AU/min$^3$) C4 substrate$^1$ | Thiolase Rate (AU/min$^3$) C5 substrate$^2$ | Reductase Rate (AU/min$^3$) C4 substrate$^1$ |
|---|---|---|---|---|
| Set 1 | | | | |
| pMON25628 | phbB | | | 0.035 |
| pMON25629 | phbC | | | |
| pMON25636 | phbA | 0.330 | 0.013 | |
| Set 2 | | | | |
| pMON25628 | phbB | | | 0.051 |
| pMON25629 | phbC | | | |
| pMON25728 | bktB | 0.132 | 0.135 | |
| Control | | | | |
| *E. coli* DH5α | | 0.008 | | 0.004 |

$^1$C4 substrate: acetoacetyl-CoA
$^2$C5 substrate: β-ketovaleryl-CoA
$^3$AU refers to absorbance units The activities of the PhbA and BktB enzymes were as expected based upon the kinetic data reported in Table 5, i.e., the PhbA β-ketothiolase was not active in thiolysis of the C5 substrate, while the BktB β-ketothiolase exhibited significant activity with C5 substrate. The levels of reductase (PhbB) activity were low due the nature of the *E. coli* DH5α host cells. Nalidixic acid is commonly used as a chemical inducer of the SOS response of *E. coli* (Walker, 1987). Since the phbB gene is transcribed from the SOS responsive recA promoter, and since *E. coli* DH5α are recA, there was no induction from the RecA promoter upon the addition of nalidixic acid. The low levels of reductase activity observed are due to leaky expression from the recA promoter. PhbC activity was not measured enzymatically; instead, the production of PHA within the *E. coli* cells was taken as proof of active PhbC enzyme.

*E. coli* DH5α cells contining both sets of plasmids expressing all of the required PHA biosynthesis enzymes were grown on 50 ml of LB broth containing all three antibiotics supplemented with 0.75% glucose and 0.15% propionate. The tac promoters were induced with IPTG at a final concentration of 0.5 mM. Nalidixic acid was added to a final concentration of 60 μtg/ml. The cells were grown under antibiotic selection (see above) for 24 hours and assayed for the presence of PHA polymer. Cells were centrifuged at 7,000 rpm for 20 min., washed with 25 ml methanol, recentrifuged, washed with 15 ml hexane, and recentrifuged. Cell pellets were dried under N$_2$ for two hours, and the dry cell weights determined. 6.5 ml of chloroform were added to extract the PHA at 100° C. for one hour. The solution was cooled and filtered through a PTFE syringe filter (13 mm diameter, 0.45 μm pore). The PHA was precipitated by the addition of 50 ml of methanol, centrifuged, and washed with hexane. The polymer was dried at 70° C. for two hours, and polymer weight was determined. Methanolysis was performed by dissolving 3–5 mg of PHA sample by the addition of 1 ml of CHCl$_3$, with methyl benzoate as an internal standard for normalization of the data. One ml of 15% H$_2$SO$_4$/MeOH was added, and the mixture was heated at 100° C. for two hours. The samples were cooled, and 0.5 ml of H$_2$O were added. The lower CHCl$_3$ layer was removed, and excess water was removed using Na$_2$SO$_4$. The solution was then analyzed by gas chromatography as described in the section entitled "In vivo Analysis of Cloned *E. coli* ilvA Genes". The results are shown in Table 11.

TABLE 11

Gas Chromatographic Analysis of PHA Produced by Transformed *E. coli* DH5α

| Set | Cell weight (mg) | PHA weight (mg) | % PHA | % C4 | % C5 |
|---|---|---|---|---|---|
| Set 1 (phbA + phb + phbC) | 146.5 | 38 | 26 | 99.1 | 0.9 |
| Set 2 (BktB + phbB + phbC) | 132.4 | 32 | 24 | 95 | 5 |

The results in Table 11 demonstrate that the total amount of P(3HB-co-3HV) copolymer produced in cells transformed with both sets of plasmid vector combinations was comparable. Furthermore, cells expressing the BktB β-ketothiolase produced a greater percentage (five-to-six-fold) of the C5 monomer than cells expressing the PhbA β-ketothiolase. In addition, the formation of P(3HB-co-3HV) in the experiments reported in Table 11 was confirmed by $^1$H-NMR (data not shown). These results support the hypothesis that the *A. eutrophus* PhbA β-ketothiolase was responsible for the metabolic block preventing the production of significant C5 constituent of the copolymer reported in Table 3.

Other β-Ketothiolases. β-Ketoacyl-CoA Reductases, and PHA Synthases for the Production of P(3HB-co-3HV) Copolymer Examples of enzymes useful in the production of P(3HB-co-3HV) copolymer have been described above. However, the present invention is not limited thereto, and other β-ketothiolases, β-ketoacyl-CoA reductases, and PHA synthases that can be used in the present invention exist, or can be obtained from other sources.

One source includes organisms possessing useful PHA biosynthetic enzymes. These include, for example, *Alcaligenes eutrophus, Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum* (Brandl et al., 1990; Doi, 1990), and *Thiocapsa pfennigii*. Using the methods described herein, one can identify and isolate DNAs encoding other β-ketothiolases, β-ketoacyl-CoA reductases, and PHA synthases useful in the present invention from these and other organisms capable of producing PHAs.

The present invention encompasses not only the *A. eutrophus* DNA sequence shown in SEQ ID NO:9, but also biologically functional equivalent nucleotide sequences. The phrase "biologically functional equivalent nucleotide sequences" denotes DNAs and RNAs, including chromosomal DNA, plasmid DNA, cDNA, synthetic DNA, and mRNA nucleotide sequences, that encode peptides, polypeptides, and proteins exhibiting the same or similar β-keto-thiolase enzymatic activity as that of A. eutrophus BktB when assayed enzymatically or by complementation. Such biologically functional equivalent nucleotide sequences can encode peptides, polypeptides, and proteins that contain a region or moiety exhibiting sequence similarity to the corresponding region or moiety of the A. eutrophus BktB β-ketothiolase.

Thus, one can isolate enzymes useful in the present invention from various organisms based on homology or sequence identity. Tombolini et al. (1995) conducted a comparative study of the homologies of known β-keto-thiolases and reductases. Although one embodiment of a nucleotide sequence encoding A. eutrophus bktB is shown in SEQ ID NO:9, it should be understood that other biologically functional equivalent forms of A. eutrophus BktB-encoding nucleic acids can be readily isolated using conventional DNA-DNA or DNA-RNA hybridization techniques. Thus, the present invention also includes nucleotide sequences that hybridize to SEQ ID NO:9 and its complementary sequence, and that code on expression for peptides, polypeptides, and proteins exhibiting the same or similar enzymatic activity as that of A. eutrophus BktB β-ketothiolase. Such nucleotide sequences preferably hybridize to SEQ ID NO:9 or its complementary sequence under moderate to high stringency (see Sambrook et al., 1989). Exemplary conditions include initial hybridization in 6×SSC, 5×Denhardt's solution, 100 mg/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize under salt and temperature conditions equivalent to those described above to genomic DNA, plasmid DNA, cDNA, or synthetic DNA molecules that encode the amino acid sequence of A. eutrophus BktB β-ketothiolase, and genetically degenerate forms thereof due to the degenerancy of the genetic code, and that code on expression for a peptide, polypeptide, or protein that has the same or similar ketothiolase enzymatic activity as that of A. eutrophus BktB β-ketothiolase.

Biologically functional equivalent nucleotide sequences of the present invention also include nucleotide sequences that encode conservative amino acid changes within the A. eutrophus BktB amino acid sequence, producing silent changes therein. Such nucleotide sequences thus contain corresponding base substitutions based upon the genetic code compared to wild-type nucleotide sequences encoding A. eutrophus BktB.

In addition to nucleotide sequences encoding conservative amino acid changes within the naturally occurring A. eutrophus BktB amino acid sequence, biologically functional equivalent nucleotide sequences of the present invention also include genomic DNA, plasmid DNA, cDNA, synthetic DNA, and mRNA nucleotide sequences encoding non-conservative amino acid substitutions, additions, or deletions. These include nucleic acids that contain the same inherent genetic information as that contained in the DNA of SEQ ID NO:9, and which encode peptides, polypeptides, or proteins exhibiting the same or similar β-ketothiolase enzymatic activity as that of A. eutrophus BktB. Such nucleotide sequences can encode fragments or variants of A. eutrophus BktB. The A. eutrophus BktB β-ketothiolase-like enzymatic activity of such fragments and variants can be identified by complementation or enzymatic assays as described above. These biologically functional equivalent nucleotide sequences can possess from 40% sequence identity, or from 60% sequence identity, or from 80% sequence identity, to 100% sequence identity to naturally occurring DNA or cDNA encoding A. eutrophus BktB β-ketothiolase, or corresponding regions or moieties thereof. However, regardless of the percent sequence identity of these biologically functional equivalent nucleotide sequences, the encoded proteins would possess the same or similar enzymatic activity as that of BktB β-ketothiolase. Thus, the biologically functional equivalent nucleotide sequences encompassed by the present invention include sequences having less than 40% sequence identity to SEQ ID NO:9, so long as they encode peptides, polypeptides, or proteins having the same or similar enzymatic actifvity as that of BktB β-ketothiolase.

Mutations made in A. eutrophus BktB β-ketothiolase cDNA, chromosomal DNA, plasmid DNA, synthetic DNA, mRNA, or other nucleic acid preferably preserve the reading frame of the coding sequence. Furthermore, these mutations preferably do not create complementary regions that could hybridize to produce secondary mRNA structures, such as loops or hairpins, that would adversely affect mRNA translation.

Useful biologically functional equivalent forms of the DNA of SEQ ID NO:9 include DNAs comprising nucleotide sequences that exhibit a level of sequence identity to corresponding regions or moieties of the genomic DNA of SEQ ID NO:9 from 40% sequence identity, or from 60% sequence identity, or from 80% sequence identity, to 100% sequence identity. However, regardless of the percent sequence identity of these nucleotide sequences, the encoded peptides, polypeptides, or proteins would possess the same or similar enzymatic activity BktB β-ketothiolase. Thus, biologically functional equivalent nucleotide sequences encompassed by the present invention include sequences having less than 40% sequence identity to SEQ ID NO:9, so long as they encode peptides, polypeptides, or proteins having the same or similar enzymatic activity as BktB β-ketothiolase. Sequence identity can be determined, for example, using the "BestFit," "Gap," or "FASTA" programs of the Sequence Analysis Software Package, Genetics Computer Group, Inc., University of Wisconsin Biotechnology Center, Madison, Wis. 53711, or using the "BLAST" program (Altschul et al., 1990).

Useful biologically functional equivalent forms of the BktB protein sequence shown in SEQ ID NO:11 include polypeptides and proteins comprising amino acid sequences that exhibit a level of sequence identitiy to the BktB protein or regions thereof of at least about 25%, preferably at least about 30%, and more preferably at least about 35%. For this purpose, sequence identity can be determined using the "TFASTA" program of the Sequence Analysis Software Packgage referred to above, or by the "BLASTP" program of Altschul et al., 1990, for example. Useful biologically functional equivalent forms of the BktB protein of the present invention also include polypeptides and proteins wherein regions required for BktB-like catalytic activity are essentially conserved or retained, but wherein non-critical regions may be modified by amino acid substitutions, deletions, or additions.

Due to the degeneracy of the genetic code, i.e., the existence of more than one codon for most of the amino acids naturally occuring in proteins, genetically degenerate DNA (and RNA) sequences that contain the same essential genetic information as the DNA of SEQ ID NO:9 of the present invention, and which encode the same amino acid sequence as that of A. eutrophus BktB, are encompassed by the present invention. Genetically degenerate forms of any of the other nucleic acid sequences discussed herein are encompassed by the present invention as well.

The nucleotide sequences described above are considered to possess a biological function substantially equivalent to that of the A. eutrophus BktB gene of the present invention if they encode peptides, polypeptides, or proteins having β-ketothiolase enzymatic activity differing from that of A. eutrophus BktB by about ±30% or less, preferably by about ±20% or less, and more preferably by about ±10% or less when assayed in vivo by complementation or by the enzymatic assays discussed above.

Based on amino acid sequence homology or sequence identity, one might attempt to predict the function of a protein of interest; however, this may not accurately reflect the activity of the protein, and it would therefore be necessary to assay the β-ketothiolase enzymatic activity thereof.

Other β-ketothiolases useful in the present invention may be derived from enzymes involved in lipid biosynthesis and β-oxidation which are not directly involved in PHA production.

EXAMPLE 9

Production of PHBV in E. coli Expressing ilvA and bktB

Figure 25:
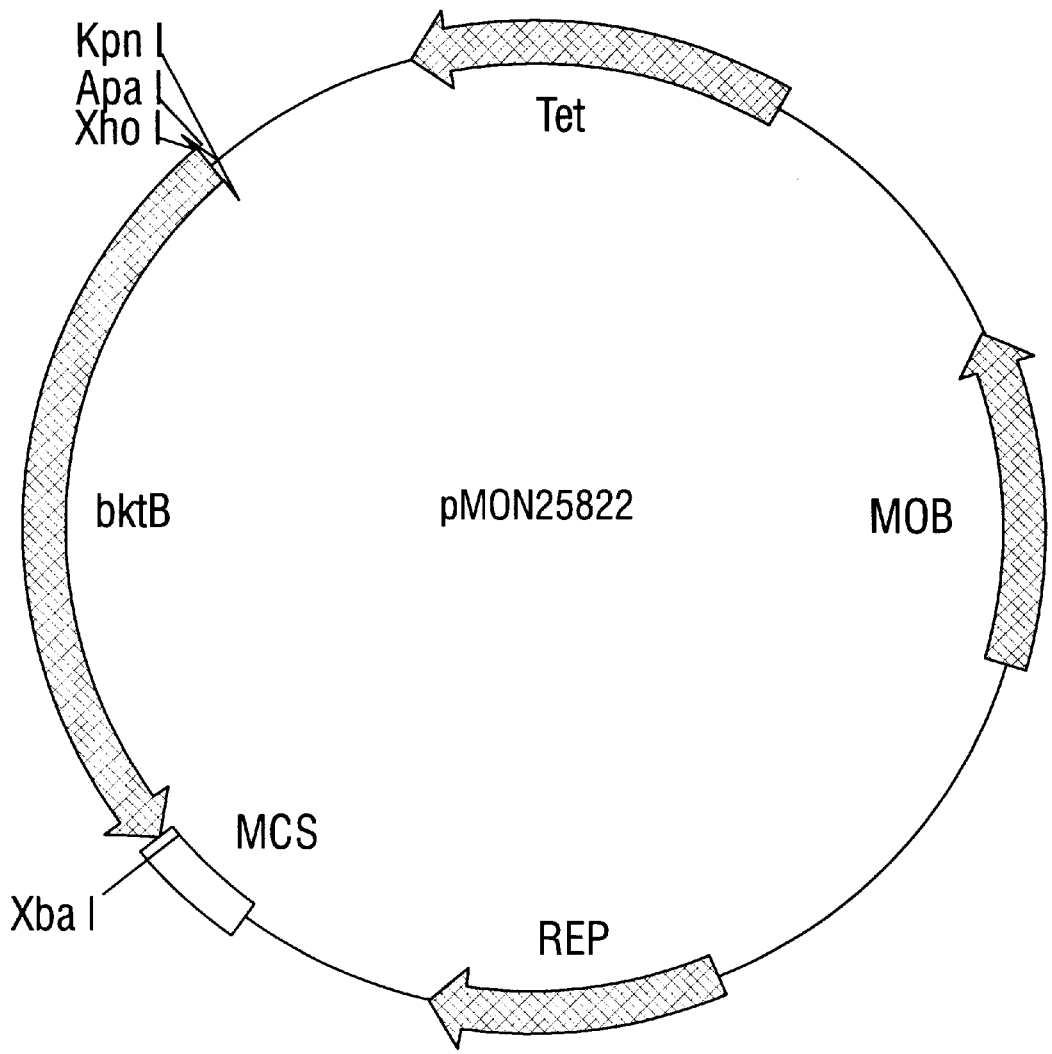
FIG. 25 shows the structure of pMON25822. This plasmid is derived from the broad host-range vector pBBR1MCS-3 (Kovach, 1994), and expresses A. eutrophus bktB from the A. eutrophus bktB promoter. The bktB promoter is included on pMON25728, discussed in example 8.

Genes required for the pathway diagrammed in FIG. 3 were assembled in recombinant E. coli in order to test the feasibility of producing PHBV from threonine in a pathway utilizing ilvA and bktB (both discussed above). E. coli DH12s (obtained from Gibco/BRL) was transformed with pMON25779 (harboring A. eutrophus phbB and phbC under Lac control) and pMON25822, which expresses bktB from the A. eutrophus bktB promoter. The resulting recombinant E. coli strain expresses BktB β-ketothiolase, PhbB β-ketoacyl-CoA reductase, and PhbC PHA synthase.

pMON25779 was constructed as follows. pJM9131 (Kidwell et al., 1995) was digested with Stu I and the vector fragment was re-closed, thereby deleting a fragment of appoximately 1 Kb that is required for production of the PhbA β-ketothiolase. The resulting plasmid, designated pMON25748, was digested with Bsa Al and Eco RI, and the fragment encoding a portion of phbC and the entire phbB gene was used to replace the Bsa AI-Eco RI fragment encoding a portion of phbC in pMON25629 (FIG. 21), producing pMON25779. pMON25779 encodes phbCB under Ptac promoter control.

pMON25822 (FIG. 25) contains a fragment of apporoximately 1.8 Kb encoding A. eutrophus bktB cloned into in the vector pBBR1MCS-3 (Kovach et al., 1994). pMON25822 was constructed as follows. pMON25765 is a pBluescript KS+ derivative that contains A 1.8 Kb Fragment encoding bktB. This plasmid is constructed by digesting pMON25728 (discussed above) partially with Sal I, then completely with Xho I, and cloning the resulting 1.8 Kb fragment into pBluescript KS+ that has been digested with Sal I and Xho I. The 1.8 Kb bktB fragment contains a total of 3 Sal I sites. pMON25765 was digested with Xho I and XbaI, and the 1.8 Kb fragment encoding bktB was ligated to pBBR1 MCS-3 digested with Xho I and XbaI.

Figure 11:
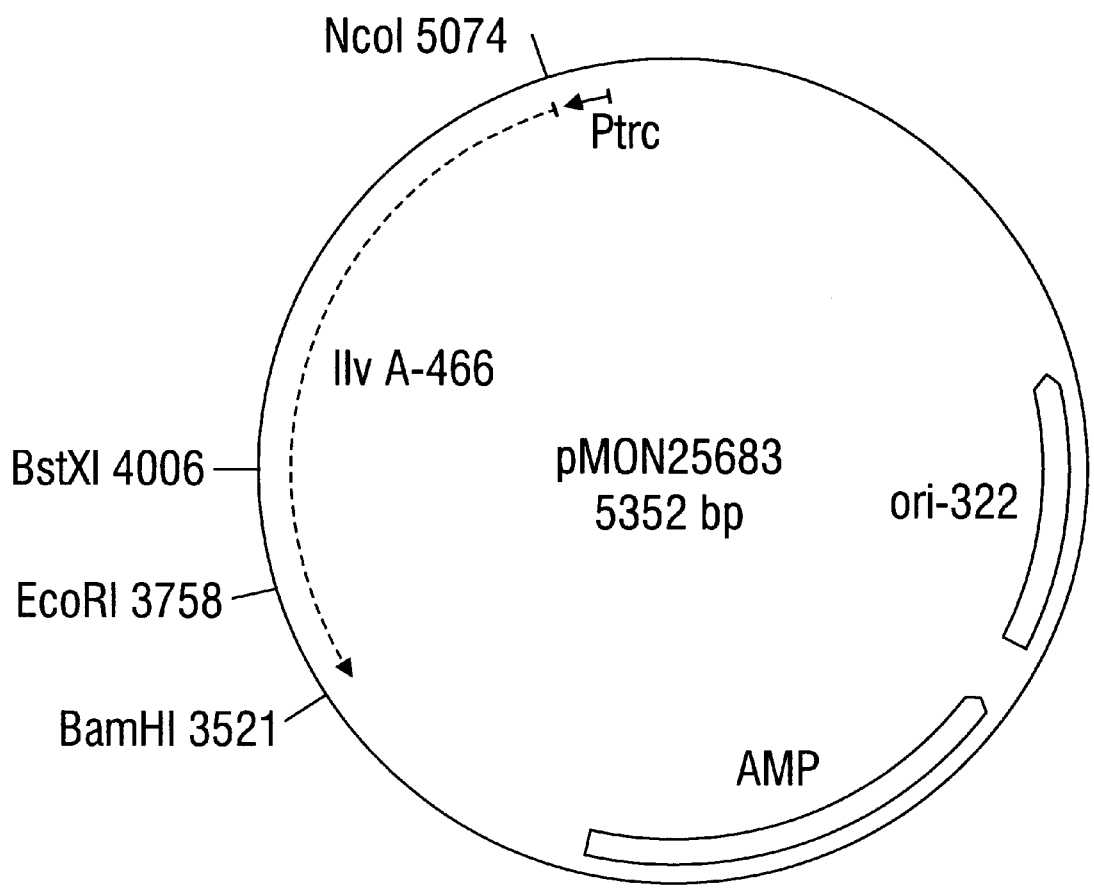
FIG. 11 shows the structure of pMON25683. pMON25683 was used for the overexpression in E. coli of the IlvA466 (L481F) mutant biosynthetic threonine deaminase from the ptrc promoter.
Figure 12:
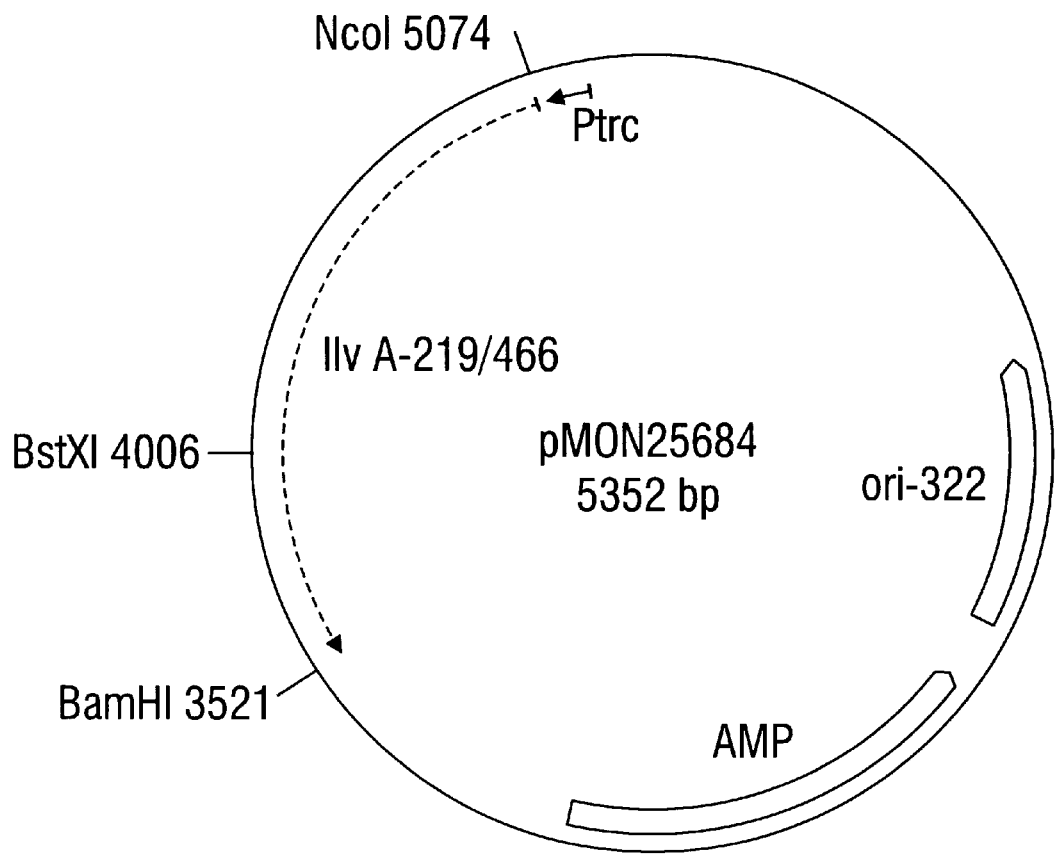
FIG. 12 shows the structure of pMON25684. pMON25684 was used for the overexpression of the IlvA219/466 (L447F/L481F) mutant biosynthetic threonine deaminase in E. coli.

To the strain harboring pMON25779 and pMON25822 was added either pSE280 (an expression vector lacking an ilvA gene: Brosius, 1989) or pMON25683 (expressing ilvA466 from the LacI-regulated promoter of pSE280: FIG. 11). Each strain was grown to late log phase in 50 ml LB containing appropriate antibiotics, then the cells were pelleted by centrifugation, washed 2 times with M9 minimal salts, and resuspended in 100 ml M9 minimal media containing 0.5% glucose as the carbon source. The resuspended cells were split into two, 50 ml cultures, and threonine was added to one flask from each pair to a final concentration of 25 mM. The flasks were incubated overnight at 37° C. with vigorous shaking. After about 18 hours, the cells were concentrated by centrifugation, and polymer composition was analyzed as described above. The results are shown in Table 12.

TABLE 12

Production of PHBV from glucose in E. coli expressing ilvA and bktB

| plasmid ilvA allele[1] | Threonine added? | mol % hydroxyvalerate |
|---|---|---|
| none | Y | 3.5 |
| none | N | N.D.[2] |
| ilvA466[3] | Y | 31.4 |
| ilvA466[3] | N | 7.9 |

[1]All strains are chromosomally ilvA+.
[2]N.D. = none detected.
[3]ilvA466 contains the L481F mutation.

As demonstrated in Table 12, E. coli harboring ilvA466 and bktB can make PHBV, even in the absence of added threonine. E. coli lacking a plasmid expressing ilvA466 also produced some PHBV if threonine was added to the media. In this case, conversion of threonine to α-ketobutyrate presumably proceeds via the chromosomally-encoded IlvA protein.

These data demonstrate that substitution of bktB for phbA overcomes the metabolic block to PHBV formation in E. coli expressing only the phb operon (Table 3). These data also demonstrate that the PHBV copolymer can be produced in vivo from endogenous substrate pools if the cell expresses a partially-deregulated threonine deaminase and PHA biosynthesis enzymes having appropriate substrate flexibility.

EXAMPLE 10

Production of P(3HB) in Seeds of Canola and Soybean

Poirier et al. (1992) and Nawrath et al. (1994) demonstrated the production of poly(3-hydroxybutyrate) (P(3HB)) homopolymer in leaves of transgenic Arabidopsis plants. Although this was the first demonstration of a plant-produced PHA, Arabidopsis is not an attractive commercial candidate for the large scale production of PHAs as this plant is primarily used as a research tool, and has no agronomic value. However, crops such as canola and soybean, for example, are excellent candidates for commercial PHA production in view of the vast acreage upon which they are grown. In addition, these crops are used for vegetable oil production, and significant pools of acetyl-CoA are present to support the oil biosynthesis that occurs in the seeds. As noted earlier, plant-produced PHAs have the potential to lower the current high cost of the microbially-produced PHAs by eliminating the fermentation costs and the expensive feedstocks required by microorganisms. For example, with properly timed and targeted expression of the PHB biosynthetic enzymes in seed plastids, one would expect to produce high levels (10%–20% fresh seed weight)

of PHB polymer. Described below are the first definitive experimental results demonstrating PHA production in commercially useful plants, such as canola and soybean.

Transformation Vectors

Figure 23:
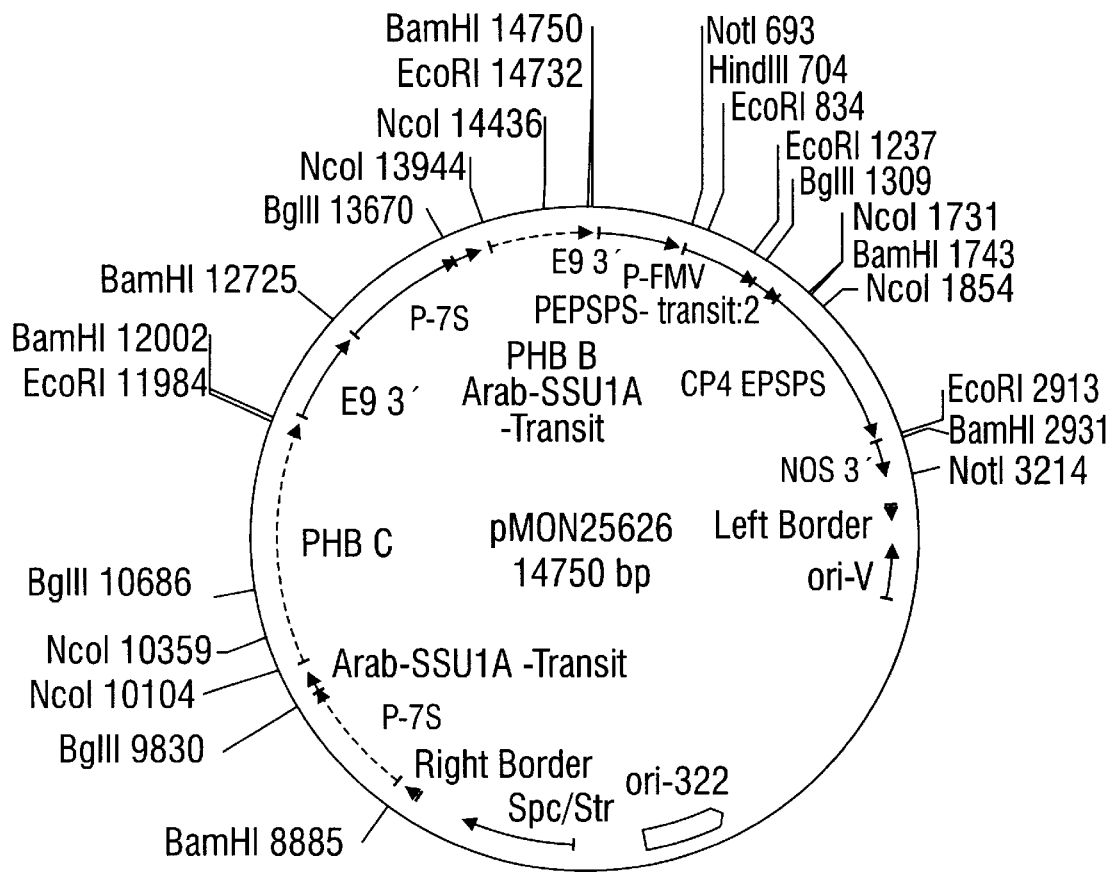
FIG. 23 shows the structure of pMON25626. pMON25626 was the Agrobacterium plant transformation vector containing the genetic elements for seed-specific, plastid-targeted expression of PhbB reductase and PhbC synthase used to transform canola and soybean.

Two Agrobacterium plant transformation vectors were constructed to introduce the entire PHB biosynthetic pathway from *A. eutrophus* into canola and soybean. The first plasmid, pMON25626 (FIG. 23), comprises the genetic information for the expression of three genes in the transformed plant: phbC, phbB and CP4 EPSPS. Specifically, pMON25626 contains, begining at the right border (RB) and continuing clockwise: the 7S β-conglycinin seed-specific promoter (Doyle et al., 1986; Slighton and Beachy, 1987) followed by the Arabidopsis small subunit of RUBP carboxylase chloroplast transit peptide (Arab-SSU1A; Stark et al., 1992) translationally fused via an Nco I site to the phbC gene, followed by the polyadenylation and transcription termination signal contained in E 9 3' (Coruzzi, et al., 1984; Morelli et al., 1985). The vector continues with the 7S promoter, Arab-SSI1A, phbB, and E9 3' termination signal, constructed as above. Additionally, pMON25626 contains the FMV promoter (Richine et al., 1987), followed by the petunia EPSPS (5-enol-pyruvylshikimate-3-phosphate synthase) chloroplast transit peptide (PEPSP; Shah et al., 1986) translationally fused to the CP4 EPSPS gene (PCT International Publication WO 92/04449; Padgette et al., 1996), and the nos 3' polyadenylation and transcription termination signal (Fraley et al., 1983). The CP4 EPSPS gene was used as the selectable herbicide resistance marker ("glyphosate selection") in the transformation procedure (Shah et al., 1986). The CP4 EPSPS enzyme is a glyphosate-resistant form of the EPSPS enzyme involved in aromatic amino biosynthesis in plants and bacteria which catalyzes the reversible reaction of shikimate-3-phosphate and phosphoenolpyruvate to produce 5-enolpyruvylshikimate-3-phosphate (Padgette et al., 1996).

Figure 24:
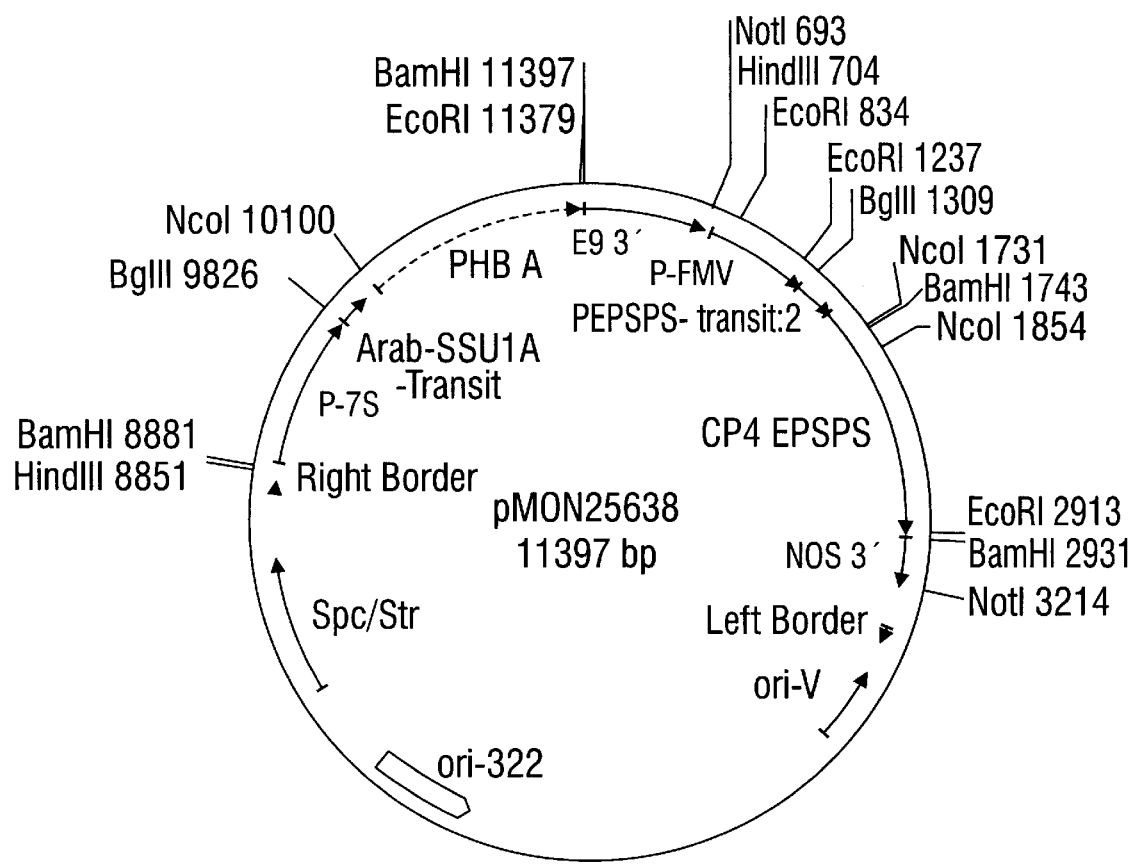
FIG. 24 shows the structure of pMON25638. pMON25638 was the Agrobacterium plant transformation vector containing the genetic elements for seed specific, plastid-targeted expression of PhbA β-keto-thiolase used to transform canola and soybean.

The second plant transformation vector, pMON25638 (FIG. 24), containing the phbA and the CP4 EPSPS genes, was constructed in a mannersimilar to that of pMON25626. The promoters, chloroplast transit peptides, and polyadenylation and transcription termination signals were identical to those described above for pMON25626. Both pMON25626 and pMON25638 contain the identical border sequence and replication origins and functions as described for pMON25668 of Example 5 in the section entitled "Expression and Activity in Transformed Soybean Callus".

Transformation Protocols pMON25626 and pMON25638 were introduced into *Agrobacterium tumefaciens* ABI (Koncz and Schell, 1986) by triparental mating (Ditta et al., 1980), which was then used for the transformation of canola (Fry et al., 1987; Radke et al., 1988) and soybean (Hinchee et al., 1988), with the modifications indicated below.

Canola Transformation

Plant Material

Stock plants were produced from seeds of the Westar variety planted in Metro Mix 350 and germinated in a growth chamber under a day temperature of 15° C., a night temperature of 10° C., a 16 hour day/8 hour night illumination period, a light intensity of 600 µEn m$^{-2}$s$^{-1}$, and 50% relative humidity. Seedlings were subirrigated with water daily, and soaked with a 15-30-15 nutrient solution every other day for one hour. At three weeks, seedlings were transferred into 6" pots. Five week old plants were harvested once the plants bolted, but prior to flowering (plants with up to three flowers can be employed, however). The leaves and buds were removed from the stem, and the 4–5 inches of stem just below the flower buds were used as the explant tissue source. Just prior to inoculation, the stems were sterilized by soaking in 70% ethanol for 1 min, 38% Chlorox (4% sodium hypochlorite) for 20 min, rinsing two times in sterile deionized water, and soaking in two tablespoons of Captan (Captan 50-WP, ICI Ag Products) plus 500 mls sterile water for 15 min.

Preparation of Agrobacterium

Five to 7 days prior to inoculation, Agrobacterium was streaked from a frozen glycerol stock onto an LB plate (1.5% agar) containing 100 mg/l spectinomycin, 100 mg/l streptomycin , 25 mg/l chloramphenicol, and 50 mg/l kanamycin (denoted LBSSCK). Two days before inoculation day, a 10 µl loop of Agrobacterium was placed into a tube containg 2 mls of LBSSCK and placed on a rotator overnight at 22–28° C. The day before inoculation, the Agrobacterium was subcultured by placing 200 µl in a tube containing 2 ml of fresh LBSSCK, which was placed on a rotator overnight. On the day of inoculation, the Agrobacterium was diluted 1:10 with MS liquid medium (Murashige and Skoog, 1962) to an OD$_{660}$ of 0.2–0.4.

Explant Inoculation

Sterilized stems were cut into 0.6 cm segments (0.3–1.5 cm segments can be used), noting their basal orientation. Explants were inoculated for five minutes in a square Petri plate (100×15 mm) with the 1:10 dilution of Agrobacterium. Five mls of Agrobacterium solution were added to five stems by pipetting the Agrobacterium directly on top of the explants. After five minutes, the Agrobacterium solution was aspirated off the explants. The stem explants were then cultured in the basal-side down orientation for an optimal shoot regeneration response on the co-culture plates. Co-culture plates (100×15 mm) contained ¹⁄₁₀ MS salts (this can range from about ¹⁄₁₀ to full strength; Gibco, 500-1117EH), 1×B5 vitamins (Sigma, G-2519), 0.5 mg/l 6-benzylamino-purine (this can range from about 0.1–2 mg/l), 3% sucrose (this can range from about 1–6%), pH 5.7, solidified with 0.9% agar, covered with 2 ml TXD liquid medium (Horsch et al., 1985) onto which an 8.5 cm piece of sterile Whatman qualitative grade filter paper was placed. Excess Agrobacterium present on the stem explants placed on the filter paper was blotted off using another piece of sterile 8.5 cm filter paper. The co-culture plates were placed in clear plastic bags which were slit on the sides to permit air exchange, and which were incubated in a warm room at 25° C. under 24 hours continuous cool white light (40 µEn m$^{-2}$s$^{-1}$).

Tissue Selection and Regeneration

After two days, the stem explants were moved onto MS medium containing 500 mg/l ticarcillin, 50 mg/l cefotaxime, and 1 mg/l 6-benzylamino-purine for a three day delay period. Plates were again placed in slit, clear plastic bags which were placed in the warm room. After a three day delay period, stem explants were moved onto glyphosate selection medium containing MS salts, B5 vitamins, 0.1 mM glyphosate (this can range from about 0.025–0.2 mM), 500 mg/l ticarcillin (this can range from about 250–750 mg/l), 50 mg/l cefotaxime (this can range from about 25–100 mg/l), and 1 mg/l 6-benzylamino-purine (this can range from about 0.1–4 mg/l) for three weeks. After three weeks, the stem explants were moved onto glyphosate selection medium containing MS salts, B5 vitamins, 0.1 mM glyphosate (this can range from about 0.025–0.2 mM), 500 mg/l ticarcillin (this can range from about 250–750 mg/l), 50 mg/l cefotaxime (this can range from about 25–100 mg/l), and 1 mg/l 6-benzylaminopurine (this can range from about 0.1–4 mg/l), plus 0.5 mg/l gibberellic acid A3 (this can range from about 0.1–2 mg/l), which enhances shoot elongation, for another three week period. After these six weeks on glyphosate selection medium, normally developing green shoots were excised from the stem explants. Shoots (4–5 per plate) were placed in rooting medium ($\frac{1}{10}$-full strength MS salts, Staba vitamins (Staba, 1969), 3% sucrose (this can range from about 1–6%), 500 mg/l ticarcillin (this can range from about 250–750 mg/l), 50 mg/l cefotaxime (this can range from about 25–100 mg/l), and 2 mg/l indolebutyric acid (this can range from about 0.5–3 mg/l), pH 5.7, solidified with 0.9% agar. Root development began to occur as early as one week after shoots were placed on rooting medium. At the two week timepoint, shoots having a large root base were moved into 2 ½" pots containing Metro Mix 350 (Hummert Co., St. Louis, Mo.). Flats were covered with clear plastic domes (Hummert Co., St. Louis) so the shoots could elongate. Flats containing Ro plants were placed in a growth chamber under the same conditions as described above for stock plant growth. After 3–4 days, the domes were cracked in order to harden off the plants under the following conditions: Temperature: 20° C. day/15° C. night; Photoperiod: 16 hr light/8 hr dark; Light intensity: 450 $\mu$En $m^{-2}s^{-1}$; Relative humidity: 70%; Fertilizer: 15-16-17 Peter's Solution (200 ppm nitrogen). Hardened plants were grown for approximately 14 weeks under the same conditions, at which time seeds were collected. Cross-pollination was prevented by bagging the plants at bolting time.

This protocol results in transformation efficiencies (defined as the number of confirmed transgenics/the number of explants inoculated, expressed as a percentage) as high as 35–40%. This is a significant improvement over the protocol using kanamycin selection (Fry et al., 1987).

Soybean Transformation

Plant Material

Seeds of soybean variety A3237 were surface sterilized by rinsing them in dilute Tween 20 (polyoxyethylenesorbitan monolaurate) for 30 seconds, followed by rinsing under running tap water for approximately two min. The seeds were then rinsed in 80% ethanol, and then agitated in freshly made 50% Chlorox (5.25% sodium hypochlorite) containing Tween 20 for 15 min. The seeds were then completely rinsed with five rinses of sterile distilled water. They were then placed in a saturated Captan and/or Benylate slurry for 2–30 min to control fingus infestation.

Sterilized seeds were then placed on 0.7% purified agar-solidified B5 basal medium (Gamborg et al., 1968) for germination (approximately 15 seeds per plate). The Petri dishes were placed in a plastic bag slit on the sides to permit air exchange, and incubated in a culture room under 18–20 hrs light (60 $\mu$En $m^{-2}s^{-1}$), 4–6 hrs dark, at 25° C., for 5–6 days. After this incubation, the germinated seeds were placed in a cold room or refrigerator (0–10° C.; average temperature of 4° C.) for at least 24 hrs prior to explanting.

Preparation of Agrobacterium

Agrobacterium strains to be used for transformation were prepared as follows. Bacteria were streaked from frozen glycerol stocks onto LBSCK plates containing 1.5% agar-solidified LB medium plus 100 mg/l of spectinomycin, 25 mg/l of chloramphenicol, and 50 mg/l of kanamycin. The bacteria can be incubated at room temperature or in an incubator at 27° C. for 2–4 days. Prior to preparing the Agrobacterium inoculum, a fresh plate of Agrobacterium was streaked from the first plate 2–3 days prior to growth on liquid medium. One to two days prior to the inoculation of soybean explants, one loop of bacteria was transferred from a freshly streaked plate into a culture tube containing 2 ml of YEP medium containing 10 g/l peptone, 10 g/l yeast extract, 5 g/l NaCl, 100 mg/l spectinomycin, 25 mg/l chloramphenicol, and 50 mg/l kanamycin. Larger volumes of bacteria can be grown using the same basic formula of one loop of bacteria per 2 ml of YEP. The tube containing the bacteria in YEP was vortexed to disperse the clump of bacteria, and placed on a rotator. For a one day culture, the bacteria can be started at about 7:00 a.m.; for a a two day culture, the bacteria can be started later in the day and allowed to grow overnight. The afternoon prior to inoculating the explants, 4–6 mls (2–3 tubes) of the bacterial culture were added to 50 mls of AB minimal salts medium (Chilton et al., 1974) containing the same concentrations of spectinomycin, chloramphenicol, and kanamycin as in the LBSCK medium, in sterile 250 ml flasks. This culture was grown on a shaker overnight at 28° C. The bacteria were pelleted by centrifugation and the pellet was resuspended to an $OD_{660}$ of 0.25–1.0 with the following medium: $\frac{1}{10}$ B5 salts (this can range from about $\frac{1}{10}$ to full strength), $\frac{1}{10}$ B5 vitamins (this can range from about $\frac{1}{10}$ to full strength), 3% sucrose or glucose (this can range from about 0.5–6% sucrose or glucose), 7.5 $\mu$M 6-benzyl-aminopurine (this can range from about 2.5–20 $\mu$M), 200 $\mu$M acetosyringone (this can range from about 50–300 $\mu$M), 1 mM galacturonic acid (this can range from about 0.1–2 mM), 0.25 mg/l gibberellic acid (GA3) (this can range from 0–0.5 mg/l), and 20 mM MES, pH 5.4 (the pH can range from about 5.2–6.0).

Explant Inoculation

Explants were prepared by removing the seed coat from the germinated seedlings and cutting the hypocotyl at approximately 0.5 cm or more from the cotyledons (one cm is preferred). The lower portion of the hypocotyl and root axis was discarded. The cotyledons and remaining hypocotyl were completely split by making an incision down the middle of the hypocotyl and then bending the halves apart so that they separated from one another. The primary leaves and primary shoot meristem were removed. The region of the cotyledon near the axillary bud was wounded multiple times (anywhere from 3–15 times) using a scalpel blade, the score marks being placed longitudinally with respect to the embryo axis. The axillary bud can be damaged in the process, but this is not required. Approximately 40–80 explants were prepared and added to a single, dry Petri dish. Approximately 10 mls of the bacterial inoculum were added to just cover the explants. The explants remained in contact with the Agrobacterium solution for 30 min. The Agrobacterium solution was then removed from the explants which were briefly blotted on sterile Whatman filter paper prior to being placed flat (adaxial) side down onto co-culture plates. Co-culture plates were prepared by adding 4–5 mls of the bacterial dilution medium additionally containing 3% sucrose, 1 mM galacturonic acid, and 200 $\mu$M acetosyringone to 1–2 layers of sterile Whatman filter paper in a 100×15 mm Petri dish. The co-culture medium can contain a mixture of 0.5–6% glucose or 0.5–6% sucrose (1–3% of either being preferred), with or without 0.1–10 mM galacturonic acid (1 mM being preferred), with or without 50–300 μM acetosyringone (100–200 μM being preferred). The co-culture medium was solidified with 0.8% washed agar (Sigma, A 8678).

Tissue Selection and Regeneration

The explants were co-cultured with the Agrobacterium in a culture room at 20–23° C. under an 18–20 hr light/4–6 hr dark photoperiod (co-culturing can be carried out from about 18–26° C.). Co-culture lasted for 2–4 days. After co-culture, the explants were washed in wash medium containing 1/10 B5 salts (this can range from about 1/10 to full strength), 1/10 B5 vitamins (this can range from about 1/10 to full strength), 7.5 μM 6-benzylaminopurine (this can range from about 2.5–20 μM), pH 5.6 (the pH can range from about 5.2–6.0), 500 mg/l ticarcillin (this can range from about 250–750 mg/l), and 100 mg/l cefotaxime (this can range from about 25–200 mg/l).

The washed explants were cultured on a culture medium containing B5-basal salts and vitamins, 7.5 μM 6-benzylaminopurine (this can range from about 2.5 μM–20 μM), 500 mg/l ticarcillin (this can range from about 250–750 mg/l), 100 mg/l cefotaxime (this can range from about 25–200 mg/l), and 0.075–0.1 mM glyphosate (this can range from about 0.025–0.4 mM). The plates were sealed with white 3M porous tape and placed in a culture room or incubator at 24–26° C. under an 18–20 hr light/4–6 hr dark cycle at 20–80 μEn m$^{-2}$s$^{-1}$. Subsequent subcultures were made every 2–3 weeks.

At two to four weeks, the cultures were transferred to MSB5 medium (Sigma, M 0404 or Gibco, 500-117EH plus Sigma, G2519) or B5 basal medium plus 1 mg/l zeatin riboside (this can range from about 0–5 mg/l), 0.5 mg/l gibberillic acid (GA3) (this can range from about 0–2 mg/l), 0.1 mg/l indoleacetic acid (this can range from about 0–1 mg/l), 2.5 μM 6-benzylaminopurine (this can range from about 0–5 μM), 500 mg/l ticarcillin (this can range from about 250–750 mg/l), 100 mg/l cefotaxime (this can range from about 25–200 mg/l), and 0.075 mM glyphosate (this can range from about 0.025–0.2 mM). Additional B5 micronutrients (up to four times the standard concentration of each micronutrient alone or in various combinations with the others) and 2 gm/l proline (this can range from about 0–2 gm/l) can be added to this medium.

At the four to six week time point, the petiole/hypocotyl tissue and cotyledons, as well as any dead or dying material, i.e., any non-regenerating tissues, were removed (such material can generally be removed between 4–9 weeks). The regenerating cultures were transferred to 0.8% washed agar-solidified elongation medium comprising MSB5 medium or B5 basal medium plus 1 mg/l zeatin riboside (this can range from about 0–5 mg/l), 0.5 mg/l gibberillic acid (this can range from about 0–2 mg/l), 0.1 mg/l indoleacetic acid (this can range from about 0–1 mg/l), 500 mg/l ticarcillin (this can range from about 250–750 mg/l), 100 mg/l cefotaxime (this can range from about 25–200 mg/l), and 0.05 mM glyphosate (this can range from about 0.025–0.2 mM), and again placed in a culture room or incubator at 24–26° C. under an 18–20 hr light/4–6 hr dark cycle at 20–80 μEn m$^{-2}$s$^{-1}$. Elongation medium can contain about 0.25–2 mg/l zeatin riboside, 0.01–1 mg/l indoleacetic acid, and 0.1–5 mg/l gibberellic acid (GA3). Cultures were transferred every three weeks to the same medium. Identification of putative A3237 transgenics (elongating, normal appearing shoots) required approximately 8–20 weeks.

Shoots were rooted on 0.7% purified agar-solidifed one-half or fuill strength MSB5 medium or one-half or full strength B5 basal medium containing 500 mg/l ticarcillin (this can range from about 0–500 mg/l), 100 mg/l cefotaxime (this can range from about 0–100 mg/l), and 1 mg/l indolebutyric acid (this can range from about 0.1–2 mg/l) or naphthaleneacetic acid (this can range from about 0.05–2 mg/l), with 0–50 mg/l glutamine and 0–50 mg/l asparagine at 24–26° C. under an 18–20 hr light/4–6 hr dark cycle for 2–6 weeks. Rooted shoots were placed in 2" pots containing moistened MetroMix 350, and kept enclosed in magenta boxes until acclimatized at 24–26° C. under an 18–20 hr light/4–6 hr dark cycle (20–80 μEn m$^{-2}$s$^{-1}$). Shoots were hardened off for 3–4 days after cracking the lids under the following conditions: Photoperiod: 18–20 hrs light/4–6 hrs dark; Light intensity: 20–80 μEn m$^{-2}$s$^{-1}$; Temperature: 24–26° C. Hardened plants were grown for approximately 3 weeks under the following conditions: Photoperiod: 12 hr light/12 hr dark; Light intensity: 450 μEn m$^{-2}$s$^{-1}$; Relative humidity: 70%; Temperature: 26° C. day/21° C. night. Transformation was confirmed by detection of expression of the CP4 gene by an ELISA assay. CP4-positive plants were subsequently grown under the following conditions: Photoperiod: 12 hr light/12 hr dark; Light intensity: 450 μEn m$^{-2}$s$^{-1}$; Relative humidity: 70%; Temperature: 26° C. day/21° C. night; Fertilizer: 15-16-17 Peter's Solution (200 ppm nitrogen). Plants were grown for approximately 11 weeks, at which time seed was collected.

Glyphosate Selection

Glyphosate (0.05 mM–0.1 mM) was employed as a selectable marker (Hinchee et al., 1994) for both canola and soybean. Leaves of glyphosate-resistant canola and soybean transformants (designated $R_0$ generation) were screened for CP4 EPSPS expression by ELISA (Padgette et al., 1995). Seeds from $R_0$ CP4-positive plants were assayed enzymatically for either the PhbA β-ketothiolase or PhbB reductase, depending upon the plasmid used for transformation (data not shown). PHA synthase was not measured enzymatically; however, this gene is carried on the same genetic insert as the phbB reductase (see FIG. 23), and plants containing PhbB activity are likely to contain PhbC activity as well. Soybean and canola seed extracts were prepared by grinding the seeds to a fine powder in liquid $N_2$, washing with acetone three times, and filtering through Whatman 3MM paper. The seed extracts were dried at 37° C., one ml of extraction buffer (100 mM KPi, pH7.4, 5 mM MgCl$_2$, 1 mM EGTA, 5 mM DTT, 10% glycerol) was added, the mixture was vortexed, and the insoluble fraction was pelleted. The extracts were used for enzyme assays and to detect all PHB biosynthetic enzymes by Western blot analysis according to Nawrath et al. (1994). Immunoreactive bands corresponding to each of these enzymes were detected in extracts of seeds of both plants (data not shown).

Since the CP4 EPSPS gene is genetically linked to the β-ketothiolase gene in pMON25638, and the reductase and PHA synthase genes in pMON25626, glyphosate spray selection (Padgette et al., 1995) was employed to identify plants retaining the CP4 EPSPS locus and respective linked PHB biosynthetic genes. Plants surviving the glyphosate spray contain the CP4 EPSPS gene and the linked PHB biosynthetic genes.

Several positive reductase-(pMON25626) and β-ketothiolase-(pMON25638) expressing plants were tested for segregation by spraying glyphosate on approximately 40 siblings of the $R_1$ generation (derived by self-pollination of $R_0$ plants). Any plant that lost the CP4 EPSPS gene due to genetic segregation will die when sprayed with glyphosate. Plant lines that segregated three CP4 positive:one CP4 negative (3:1, indicating the presence of only a single genetic locus) were retained for production of homozygous plants for the respective β-ketothiolase and reductase loci. For each independent line that segregated 3:1, approximately ten $R_1$ sibling plants per line were retained for seed production. Seeds from each of the siblings (designated $R_2$ generation) were planted, and approximately 40 plants per line were sprayed with glyphosate. Lines in which all $R_2$ siblings survived the glyphosate spray were considered to be homozygous for the respective loci.

In order to assemble the entire PHB biosynthetic pathway in a single plant, homozygous plants derived from transformed canola or soybean containing pMON25626 (PhbC and PhbB) were crossed with homozygous plants containing pMON25638 (PhbA). Seeds from the crosses (designated $F_1$) were assayed for the presence of the β-ketothiolase and reductase to confirm successful crossing (data not shown). At this point in the breeding cycle, the plants are not homozygous for all three genes. The locus containing the bketothiolase gene segregates independently from the locus containing the reductase and synthase genes. The segregation ratio in the $F_1$ generation would follow a typical Mendelian pattern of inheritance. Five $F_1$ progeny seeds were planted, and seeds obtained therefrom (designated $F_2$) were collected and assayed for the presence of PHB as described below.

Isolation and Characterization of Poly(3-Hydroxybutyrate) from Transgenic Canola Seeds 40 g of $F_2$ transgenic canola seeds were crushed in a mechanical benchtop crusher (Cemotec 1090 Sample Mill, Grinding Disc set to position 1) and then transferred to cellulose extraction thimbles (Whatman, Single thickness, 26 mm external diameter×60 mm external length). Extraction was carried out in these thimbles under refluxing chloroform at 80° C. using a Soxtec Extraction System (Tecator).

After approximately 12 hours of extraction, the extract was collected in a flask, and the chloroform evaporated in a fume-hood under a stream of air/nitrogen, leaving behind canola oil and an insoluble, gel-like solid residue. To this mixture, 50 ml of hexanes were added, and the mixture was stirred for 5 minutes to dissolve the oil. The mixture was then centrifuged for 5 minutes at 1,700×g, producing a white pellet. The supernatant was decanted off, and the pellet redissolved in 10 ml chloroform. Upon stirring this solution with 100 ml hexanes, a white precipitate was obtained. This precipitate was recovered by centrifugation, washed twice with 30 ml hexanes to remove the residual oil, and dried under a stream of nitrogen for two hours at room temperature, and under vacuum for three hours at approximately 40–50° C.

Structural analysis of a 3 mg/ml solution of the precipitate in deuterated-chloroform (99.8% D, Aldrich Chemical Co., USA) by a 300-MHz $^1$H-NMR performed on a Varian VX-300 spectrometer confirmed it to be pure Poly(3-hydroxybutyrate) (P(3HB)) (data not shown).

Figure 26A:
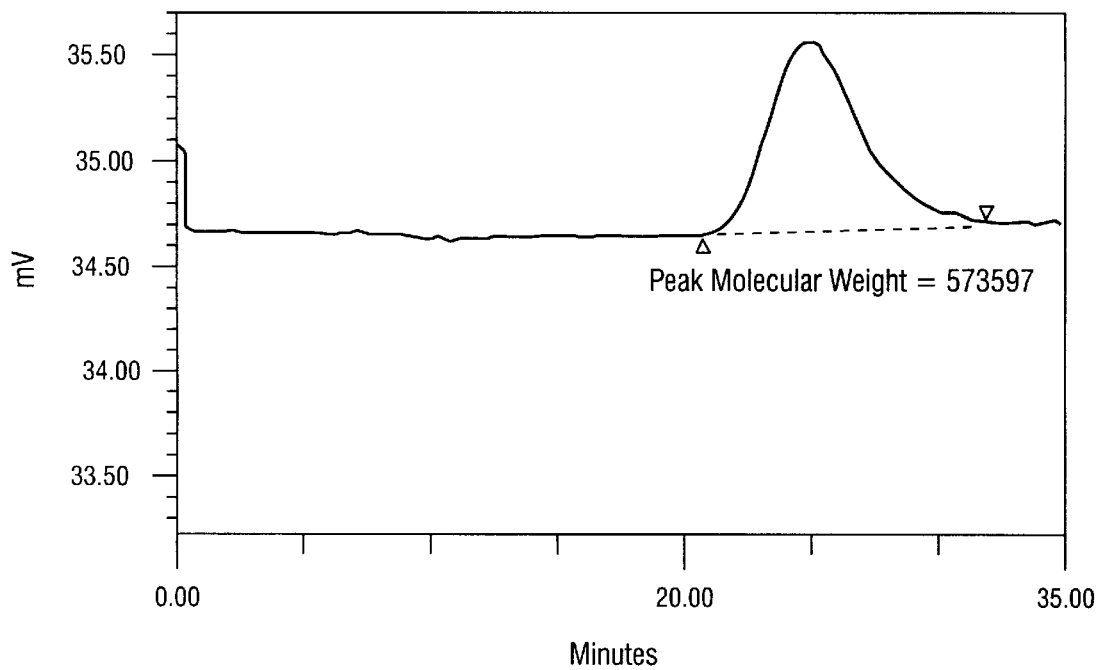
FIG. 26 shows a GPC trace of polyhydroxyalkanoate polymers isolated from the transformed canola of Example 10.
Figure 26B:
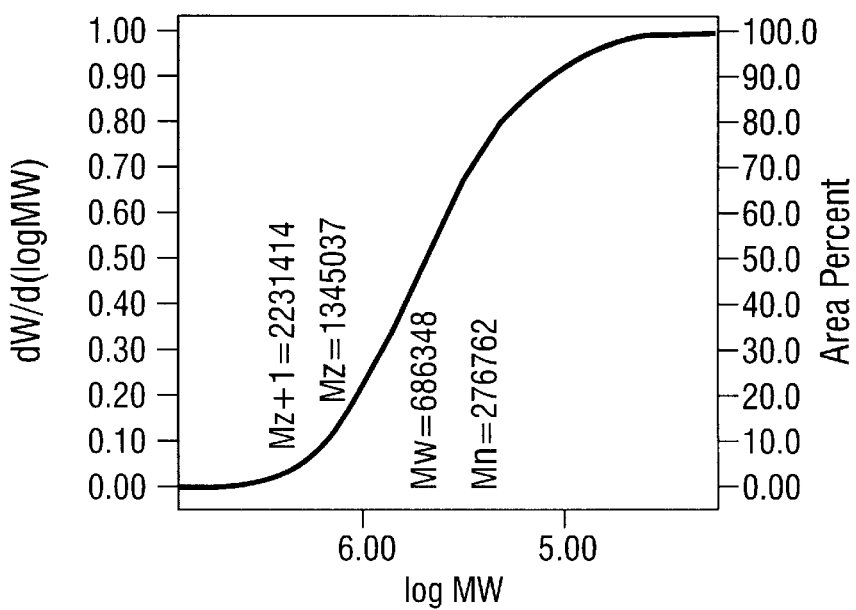

Molecular weight data were obtained at 35° C. using a Waters Millennium GPC System and a 410 Differential Refractometer with Waters Ultrastyragel Columns of pore sizes 105 •, 104 •, 103 • and 500 • connected in series. Chloroform was used as eluent at a flow rate of 1 ml/min, and a sample concentration of 6 mg/ml was used. Polystyrene standards with a low polydispersity (Aldrich Chemical Company, USA) were used to prepare a calibration curve. The results are shown in Table 13 and FIG. 26.

TABLE 13

Production of P(3HB) in Transgenic Canola Seeds

| Weight of canola seeds | Weight of PHB obtained | % PHB (with respect to seed weight) | $Mw^1$ (Daltons) | $Mn^2$ (Daltons) | Polydispersity (Mw/Mn) |
|---|---|---|---|---|---|
| 40 g | 0.2 g | 0.5% | 686,300 | 276,800 | 2.5 |

$^1$Mw: Weight average molecular weight.
$^2$Mn: Number average molecular weight.

Figure 27A:
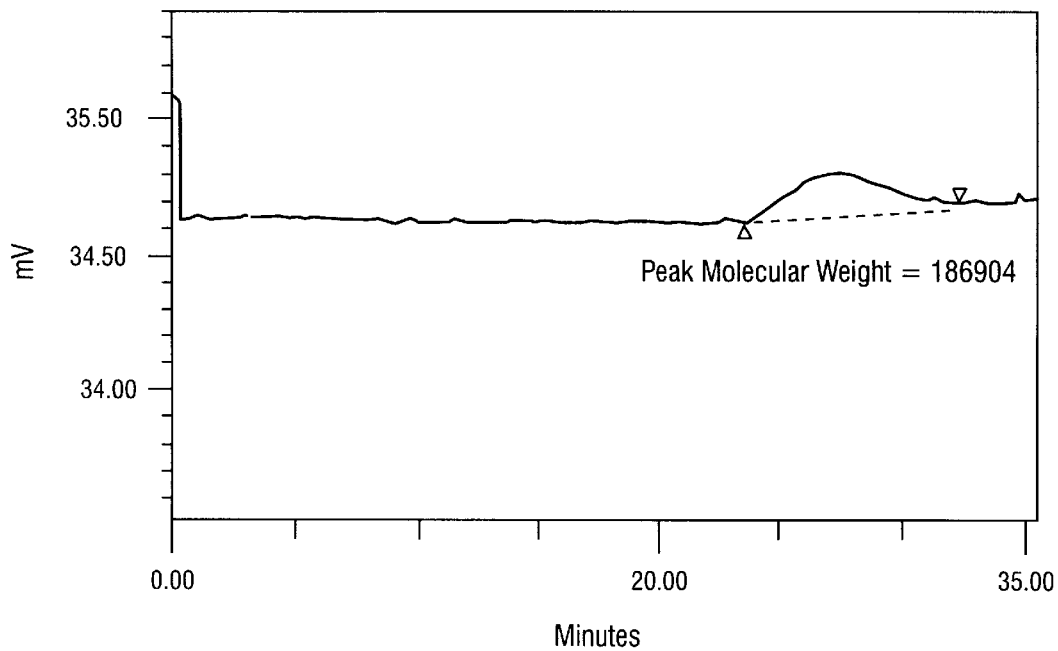
FIG. 27 shows a GPC trace of polyhydroxyalkanoate polymers isolated from transformed soybean of Example 10.
Figure 27B:
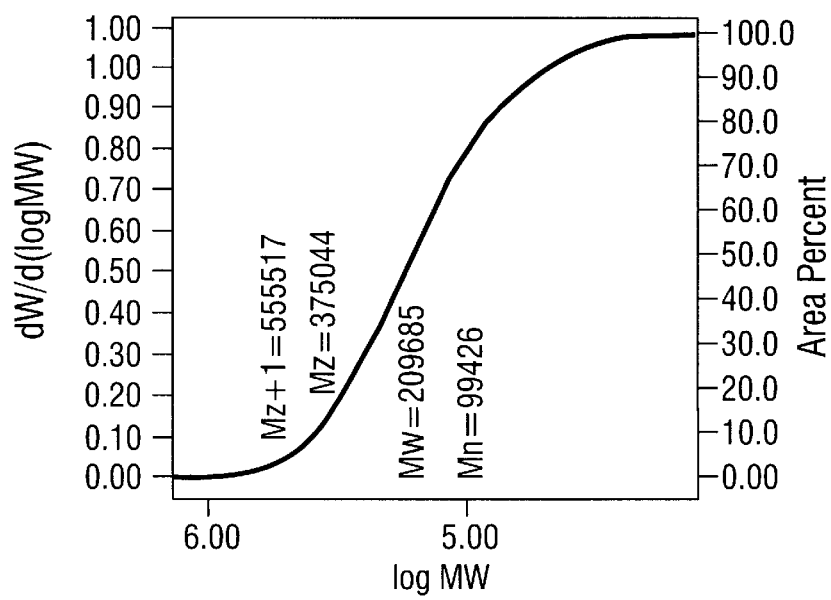

Isolation and Characterization of Poly(3-Hydroxybutyrate) from Transgenic Soybean Seeds The extraction procedure described above for canola seeds was also employed for transgenic soybean seeds, using 10 g of $F_2$ generation crushed seeds. The results are as summarized in Table 14 and FIG. 27.

TABLE 14

Production of P(3HB) in Transgenic Soybean Seeds

| Weight of soybean seeds | Weight of PHB obtained | % PHB (with respect to seed weight) | $Mw^1$ (Daltons) | $Mn^2$ (Daltons) | Polydispersity (Mw/Mn) |
|---|---|---|---|---|---|
| 10 g | 0.0015 g | 0.015% | 209,700 | 99,400 | 2.1 |

$^1$Mw: Weight average molecular weight.
$^2$Mn: Number average molecular weight.

The data presented in Tables 13 and 14, respectively, confirm the biosynthesis of P(3HB) in canola seeds at a level of at least 0.5% of total seed weight, as well as the biosynthesis of P(3HB) in soybean seeds at a level of at least 0.015% of the total seed weight, by transformation and breeding employing plastid-targeted, seed-specific expression of the *A. eutrophus* PHB biosynthetic enzymes. These results represent the first definitive demonstration of the production of PHA in oilseeds of transgenic commercial crops.

EXAMPLE 11

Optimization of P(3HB-co-3HV) Copolymer Production in Plant and Bacterial Cells The ability to biosynthesize PHAs such as P(3HB-co-3HV) copolymer can be conferred upon heterologous host cells by introduction therein of appropriate enzyme-encoding nucleic acids in such a manner that they express enzymatically active products. Introduction into bacterial and plant cells of genetic constructs containing chromosomal DNAs, plasmid DNAs, cDNAs, and synthetic DNAs encoding PHA biosynthetic enzymes, in various combinations with the enzymes discussed above, wherein such nucleic acids are operably linked to appropriate regulatory regions for expression depending upon the host cell, enables such cells to biosynthesize and accumulate PHAs. In bacteria for example, Slater et al. (1988) and Schubert et al. (1988) have demonstrated that *E. coli* transformed with and expressing the *A. eutrophus* phba, phbB, and phbC genes produces significant levels of PHB. In plants, Poirier et al. (1992) have shown that Arabidopsis expressing these genes produces the PHB homopolymer. Higher levels of PHB were obtained by targeting the Phb enzymes to the leaf plastids (Nawrath et al., 1994).

In view of the ability of heterologous bacterial and plant host cells to produce PHB polyhydroxyalkanoate upon introduction and expression therein of DNAs encoding the appropriate PHB biosynthetic enzymes, it is similarly expected that P(3HB-co-3HV) copolymer can be produced in bacteria and plants by expressing therein appropriate combinations of PHA-biosynthetic and other enzymes as discussed above. As the levels of acetyl-CoA required for copolymer biosynthesis in bacteria and plant cells appear to be non-limiting (Nawrath et. al., 1994), no further manipulation of cellular metabolism with respect to this precursor is likely to be necessary. Insuring the presence of sufficient pools of propionyl-CoA required for C4/C5 copolymer production may require introduction into, and overexpression in, host cells of various combinations of wild-type or deregulated aspartate kinase, homoserine dehydrogenase, threonine synthase, wild-type or deregulated threonine deaminase, α-ketoacid dehydrogenase E1, E2, and E3 subunits, pyruvate oxidase, and acyl-CoA synthetase enzymes.

Thus, DNA encoding the following enzymes can be introduced into and expressed in plants and bacteria in which P(3HB-co-3HV) copolymer is desired: an appropriate β-ketothiolase or combination of β-ketothiolases, a β-ketoacyl-CoA reductase, and a PHA synthase. If necessary, DNA encoding a wild-type or deregulated threonine deaminase can also be introduced into and expressed in these organisms. The β-ketothiolase can be the BktB β-ketothiolase of A. eutrophus, or one similar thereto, that can condense two molecules of acetyl-CoA to produce acetoacetyl-CoA, and that can also condense acetyl-CoA and propionyl-CoA to produce β-ketovaleryl-CoA. Alternatively, a combination of β-ketothiolases can be employed, i.e., a β-ketothiolase capable of condensing two molecules of acetyl-CoA to produce acetoacetyl-CoA, and a β-ketothiolase capable of condensing acetyl-CoA and propionyl-CoA to produce β-ketovaleryl-CoA. The β-ketoacyl-CoA reductase can be one such as that encoded by the A. eutrophus phbB gene; the PHA synthase can be one such as that from A. eutrophus as well. A. eutrophus is only one of many microorganisms that produce PHAs, and DNA (genomic, plasmid, cDNA, or synthetic DNA) encoding any of the foregoing enzymes can be derived from any other PHA-producing organism containing enzymes having the same or similar enzymatic activity as the A. eutrophus enzymes, as discussed above in Example 8 in the section entitled "Other β-Ketothiolases, β-Ketoacyl-CoA Reductases, and PHA Synthases for the Production of P(3HB-co-3HV) Copolymer."

As described in Examples 1–8, there are a number of different methods by which the levels of α-ketobutyrate, propionyl-CoA, and ultimately 3hydroxy-valeryl-CoA which can be utilized in PHA synthesis can be increased in heterologous bacterial and plant host cells. These are summarized below.

Overexpression of Threonine Deaminase

The simplest method of increasing the level of α-ketobutyrate in a bacterial or plant host cell involves overexpressing a wild-type or deregulated threonine deaminase in such cells. In plants, this enzyme can be expressed cytoplasmically, targeted to the plastids using appropriate chloroplast transit peptides, or expressed directly within these organelles by plastid transformation. These strategies are discussed in more detail below.

Overexpression of Aspartate Kinase and Threonine Deaminase

Overexpression of a wild-type or deregulated aspartate kinase will result in an increase in intracellular levels of L-threonine. Deregulated aspartate kinases have been described, for example, in E. coli (Boy et al., 1979; Karchi et al., 1993), C. lactofermentum (Jetten et al., 1995), barley (Bright et al., 1982), maize (Dotson et al., 1990; Hibberd et al., 1980), carrot (Cattoir-Reynaerts et al., 1983), and tobacco (Frankard et al., 1991). Expression of these enzymes in the cytoplasm, targeting of these enzymes to the plastids of plant cells, or expression of these enzymes in plastids following plastid transformation, will result in an increase in L-threonine therein. Simultaneous overexpression of a wild-type or deregulated threonine deaminase in bacterial cells, or in the cytoplasm or plastids of plant cells, will result in conversion of this excess L-threonine to α-ketobutyrate, which will then lead to increased levels of propionyl-CoA and then 3-hydroxyvaleryl-CoA, which can be employed in P(3HB-co-3HV) copolymer biosynthesis.

Overexpression of Aspartate Kinase, Homoserine Dehydrogenase, and Threonine Deaminase An overexpressed homoserine dehydrogenase can be used in conjunction with a wild-type or deregulated aspartate kinase to increase further the level of threonine in bacterial cells, or in plant cells and plastids by employing appropriate chloroplast transit peptides or chloroplast transformation. The excess threonine can then be directed to 3-hydroxyvaleryl-CoA synthesis via α-ketobutyrate by an overexpressed wild-type or deregulated threonine deaminase, which can be targeted to or expressed in plastids in plant cells.

Overexpression of Threonine Deaminase, Pyruvate Oxidase. and Acyl-CoA Synthetase α-ketobutyrate levels can be enhanced in bacterial cells and plant plastids (via chloroplast transit peptide targeting or plastid transformation) by overexpressing a wild-type or deregulated threonine deaminase. The excess α-ketobutyrate can then be converted to propionate and $CO_2$ by an overexpressed pyruvate oxidase, for example, E. coli PoxB. Endogenous or overexpressed bacterial or plastid acyl-CoA synthetases will then activate the free propionate to produce propionyl-CoA, which can then be used by plants expressing other appropriate genes (for example, isoleucine-deregulated threonine deaminase and BktB β-ketothiolase) to form the 3-hydroxyvaleryl-CoA monomer employed in P(3HB-co-3HV) copolymer synthesis.

Overexpression of Aspartate Kinase, Homoserine Dehydrogenase, Threonine Deaminase, Pyruvate Oxidase, and Acyl-CoA Synthetase A wild-type or deregulated threonine deaminase, aspartate kinase, homoserine dehydrogenase, pyruvate oxidase, and an acyl-CoA synthetase, each having the effect variously described above, can be simultaneously overexpressed in bacterial cells or plant cells and plastids (via the use of a chloroplast transit peptide or plastid transformation) to provide increased levels of propionyl-CoA and, eventually, 3-hydroxyvaleryl-CoA, which can be incorporated into P(3HB-co-3HV) copolymer in the presence of β-ketothiolase, acetoacetyl-CoA reductase, and PHA synthase.

Overexpression of Aspartate Kinase, Homoserine Dehydrogenase, Threonine Synthase, Threonine Deaminase, Pyruvate Oxidase, and Acyl-CoA Synthetase In addition to aspartate kinase, homoserine dehydrogenase, threonine deaminase, pyruvate oxidase, an acyl-CoA synthetase, and threonine synthase can also be introduced into plant and bacterial cells to provide increased levels of propionyl-CoA and, eventually, 3-hydroxyvaleryl-CoA, which can be incorporated into P(3HB-co-3HV) copolymer in the presence of β-ketothiolase, acetoacetyl-CoA reductase, and PHA synthase.

Overexpression of a Branched-Chain α-Ketoacid Dehydrogenase Complex E1 Subunit As discussed in Example 6, pyruvate dehydrogenase complex catalyzes the oxidative decarboxylation of α-ketobutyrate to form propionyl-CoA. Pyruvate dehydrogenase complex is a multienzyme complex containing three activities: a pyruvate decarboxylase (E1); a dihydrolipoyl transacetylase (E2); and a dihydrolipoyl dehydrogenase (E3).

Overexpression of a branched-chain α-ketoacid dehydrogenase E1 subunit having improved binding and decarboxylating activity with α-ketobutyrate as compared to the naturally occurring E1 subunit may effectively compete with the endogenous bacterial or plant E1 subunit. This overexpressed E1 subunit will combine with the endogenous pyruvate dehydrogenase E2E3 subcomplex to create a functional hybrid complex capable of turning over α-ketobutyrate to propionyl-CoA, which can then be metabolized to 3-hydroxyvaleryl-CoA for incorporation into P(3HB-co-3HV) copolymer.

Alternatively, both the E1 and E2 components of a branched-chain α-ketoacid dehydrogenase complex that has significant activity with α-ketobutyrate can be overexpressed. Overexpression of the dihydrolipoyl dehydrogenase E3 subunit may not be necessary as this subunit is common to all α-ketoacid dehydrogenase complexes. However, if the endogenous E3 levels are not sufficient for E1 E2 of endogenous PDC and the overexpressed E1 E2 of a branched-chain α-ketoacid dehydrogenase complex, then it too can be overexpressed.

Overexpression of an α-ketoacid dehydrogenase complex E1 subunit having greater binding and decarboxylating activity with α-ketobutyrate than the naturally occurring E1 subunit in bacterial cells or plant plastids, or overexpression of both E1 and E2 components as discussed above, can be employed in conjunction with any of the other methods discussed herein as a means for increasing the amounts of propionyl-CoA and subsequently 3-hydroxyvaleryl-CoA available for P(3HB-co-3HV) copolymer synthesis.

Production of Transformed Bacteria and Transgenic Plants Capable of Producing P(3HB-co-3HV) Copolymer PHA synthesis in bacteria and plants can be optimized in accordance with the present invention by expressing DNAs encoding β-ketothiolase, β-acyl-CoA reductase, and PHA synthase in conjunction with various combinations of precursor-producing enzymes, as discussed in the foregoing Examples. Methods therefor are discussed below.

Bacterial Vectors

Methods for incorporating all the genes discussed herein into transformation/expression vector constructs and introducing these constructs into bacterial and plant host cells to produce PHAs in such cells are well known in the art. Poirier et al. (1995) have recently provided an extensive review of progess in this area. In general, such vector constructs comprise assemblies of DNA fragments operatively linked in a functional manner such that they drive the expression of the structural DNA sequences contained therein. These vector constructs usually contain a promoter that fumctions in the selected host cell, along with any other necessary regulatory regions such as ribosome binding sites, transcription terminators, 3' non-translated polyadenylation signals, etc., linked together in an operable manner, as well as selectable markers (Sambrook et al., 1989; Ausubel et al. 1989). Vectors for bacterial cloning have been reviewed in Rodriguez et al. (1988).

Bacterial Transformation

Such vectors can be introduced into bacterial cells by calcium chloride/heat shock treatment or electroporation. Transformed host cells can subsequently be selected on selective media, cultured in an appropriate medium for a time and under conditions conducive to the production of PHA, and the PHA can then be recovered. Representative methods have been described by Slater et al. (1988); Slater et al. (1992); Zhang et al. (1994); and Kidwell et al. (1995).

Bacterial and Other Host Cells

Useful host organisms for PHA polymer production include Actinomycetes (e.g., Streptomyces sp. and Nocardia sp.); bacteria (e.g., Alcaligenes (e.g., *A. eutrophus*), *Bacillus cereus, B. subtilis, B. licheniformis, B. megaterium, Escherichia coli*, Klebsiella (e.g., *K. aerogenes* and *K. oxytoca*), Lactobacillus, Methylomonas, Pseudomonas (e.g., *P. putida* and *P. fluorescens*); fungi (e.g., Aspergillus, Cephalosporium, and Penicillium); and yeast (e.g., Saccharomyces, Rhodotorula, Candida, Hansenula, and Pichia).

Organisms capable of overproducing threonine either naturally, via chemical or physical mutagenesis, or via recombinant DNA methodology (Jetten & Sinskey, 1995), can be used in the present invention for the production of P(3HB-co-3HV) copolymer. DNAs selected from the group consisting of DNA encoding a wild-type or deregulated threonine deaminase, a β-ketothiolase capable of condensing two molecules of acetyl-CoA to produce acetoacetyl-CoA, a β-ketothiolase capable of condensing acetyl-CoA and propionyl-CoA to form β-ketovaleryl-CoA, e.g., BktB, a β-ketoacyl-CoA reductase capable of converting a β-ketoacyl-CoA to its corresponding β-hydroxyacyl-CoA, e.g., PhbB, and a PHA synthase capable of producing P(3HB-co-3HV) copolymer from the β-hydroxyacyl-CoAs, e.g., PhbC, or combinations thereof, can be introduced into these organisms in order to impart P(3HB-co-3HV) copolymer production capability thereto.

Organisms that are capable of producing propionate or propionyl-CoA and other odd-chain substrates from simple precursors such as glucose, lactate, etc., are also useful for producing P(3HB-co-3HV) copolymer. For example, DNAs encoding a β-ketothiolase capable of condensing two molecules of acetyl-CoA to produce acetoacetyl-CoA, a β-ketothiolase capable of condensing acetyl-CoA and propionyl-CoA to form β-ketovaleryl-CoA, e.g., BktB, a β-ketoacyl-CoA reductase capable of converting a β-ketoacyl-CoA to its corresponding β-hydroxyacyl-CoA, e.g., PhbB, and a PHA synthase capable of producing P(3HB-co-3HV) copolymer from the β-hydroxyacyl-CoAs, e.g., PhbC, or combinations thereof, can be introduced into these organisms. Examples of such organisms include members of the genus Clostridium, such as *Clostridium arcticum, Clostridium novyi, Clostridium propionicum*, as well as *Megasphaera elsdenii*.

In addition, organisms that are capable of producing butyrate or butyryl-CoA from simple precursors are useful for producing C4/C6 copolymer, i.e., P(3HB-co-3HC) copolymer. For example, DNAs encoding a β-ketothiolase capable of condensing two molecules of acetyl-CoA to produce acetoacetyl-CoA, a β-ketothiolase capable of condensing acetyl-CoA and butyryl-CoA to form β-ketocaproyl-CoA, e.g., BktB, a β-ketoacyl-CoA reductase capable of converting a β-ketoacyl-CoA to its corresponding β-hydroxyacyl-CoA, e.g., PhbB, and a PHA synthase capable of producing P(3HB-co-3HC) copolymer from the β-hydroxyacyl-CoA, e.g., *Nocardia corallina* PHA synthase, or combinations thereof, can be introduced into these organisms. Examples of such organisms include species of the genera Butyrivibrio, Clostridium (e.g., *Clostridium populeti*), Eubacterium, and Fusarium (Patel and Agnew, 1988).

Plant Vectors

In plants, transformation vectors capable of introducing encoding DNAs involved in PHA biosynthesis are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (1988), Glick et al. (1993), and Croy (1993).

Plant Promoters

Plant promoter sequences can be constitutive or inducible, environmentally- or developmentally-regulated, or cell- or tissue-specific. Often-used constitutive promoters include the CaMV 35S promoter (Odell et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter. Useful inducible promoters include heat-shock promoters (Ou-Lee et al., 1986; Ainley et al., 1990), a nitrate-inducible promoter derived from the spinach nitrite reductase gene (Back et al., 1991), hormone-inducible promoters (Yamaguchi-Shinozaki et al., 1990; Kares et al., 1990), and light-inducible promoters associated with the small subunit of RuBP carboxylase and LHCP gene families (Kuhlemeier et al., 1989; Feinbaum et al., 1991; Weisshaar et al., 1991; Lam and Chua, 1990; Castresana et al., 1988; Schulze-Lefert et al., 1989). Examples of useful tissue-specific, developmentally-regulated promoters include the β-conglycinin 7S promoter (Doyle et al., 1986; Slighton and Beachy, 1987), and seed-specific promoters (Knutzon et al., 1992; Bustos et al., 1991; Lam and Chua, 1991; Stayton et al., 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity.

A factor to be considered in the choice of promoters is the timing of availability of the necessary substrates during expression of the PHA biosynthetic enzymes. For example, if P(3HB-co-3HV) copolymer is produced in seeds from threonine, the timing of threonine biosynthesis and the amount of free threonine are important considerations. Karchi et al. (1994) have reported that threonine biosynthesis occurs rather late in seed development, similar to the timing of seed storage protein accumulation. For example, if enzymes involved in P(3HB-co-3HV) copolymer biosynthesis are expressed from the 7S seed-specific promoter, the timing of expression thereof will be concurrent with threonine accumulation.

Plant Transformation and Regeneration

A variety of different methods can be employed to introduce such vectors into plant protoplasts, cells, callus tissue, leaf discs, meristems, etc., to generate transgenic plants, including Agrobacterium-mediated transformation, particle gun delivery, microinjection, electroporation, polyethylene glycolmediated protoplast transformation, liposome-mediated transformation, etc. (reviewed in Potrykus, 1991). In general, transgenic plants comprising cells containing and expressing DNAs encoding enzymes facilitating PHA biosynthesis can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

Constitutive overexpression of, for example, a deregulated threonine deaminase employing the e35S or FMV promoter might potentially starve plants of certain amino acids, especially those of the aspartate family. If such starvation occurs, the negative effects may be avoided by supplementing the growth and cultivation media employed in the transformation and regeneration procedures with appropriate amino acids. By supplementing the transformation/regeneration media with aspartate family amino acids (aspartate, threonine, lysine, and methionine), the uptake of these amino acids into the plant can reduce any potential starvation effect caused by an overexpressed threonine deaminase. Supplementation of the media with such amino acids might thereby prevent any negative selection, and therefore any adverse effect on transformation frequency, due to the overexpression of a deregulated threonine deaminase in the transformed plant.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the entire pathway into a single plant. Successful production of the PHA polyhydroxybutyrate in is cells of Arabidopsis has been demonstrated by Poirier et al. (1992), and in plastids thereof by Nawrath et al. (1994).

Specific methods for transforming a wide variety of dicots and obtaining transgenic plants are well documented in the literature (Gasser and Fraley, 1989; Fisk and Dandekar, 1993; Christou, 1994; and the references cited therein).

Successful transformation and plant regeneration have been achieved in the monocots as follows: asparagus (*Asparagus officinalis*; Bytebier et al. 1987); barley (*Hordeum vulgarae*; Wan and Lemaux 1994); maize (*Zea mays*; Rhodes et al., 1988; Gordon-Kamm et al., 1990; Fromm et al., 1990; Koziel et al., 1993); oats (*Avena sativa*; Somers et al., 1992); orchardgrass (*Dactylis glomerata*; Horn et al., 1988); rice (*Oryza sativa*, including indica and japonica varieties; Toriyama et al., 1988; Zhang et al., 1988; Luo and Wu 1988; Zhang and Wu 1988; Christou et al., 1991); rye (*Secale cereale*; De la Pena et al., 1987); sorghum (*Sorghum bicolor*; Cassas et al. 1993); sugar cane (Saccharum spp.; Bower and Birch 1992); tall fescue (*Festuca arundinacea*; Wang et al. 1992); turfgrass (*Agrostis palustris*; Zhong et al., 1993); wheat (*Triticum aestivum*; Vasil et al. 1992; Weeks et al. 1993; Becker et al. 1994), and alfalfa (Masoud, S. A. et al.1996).

Host Plants

Particularly useful plants for PHA copolymer production include those that produce carbon substrates which can be employed for PHA biosynthesis, including tobacco, wheat, potato, Arabidopsis, and high oil seed plants such as corn, soybean, canola, oil seed rape, sunflower, flax, peanut, sugarcane, switchgrass, and alfalfa. Polymers that can be produced in this manner include copolymers incorporating both short chain length and medium chain length monomers, such as P(3HB-co-3HV) copolymer.

If the host plant of choice does not produce the requisite fatty acid substrates in sufficient quantities, it can be modified, for example by mutagenesis or genetic transformation, to block or modulate the glycerol ester and fatty acid biosynthesis or degradation pathways so that it accumulates the appropriate substrates for PHA production.

P(3HB-co-3HV) Copolymer Composition

The P(3HB-co-3HV) copolymers of the present invention can comprise about 75–99% 3HB and about 1–25% 3HV based on the total weight of the polymer. More preferably, P(3HB-co-3HV) copolymers of the present invention comprise about 85–99% 3HB and about 1–15% 3HV. Even more preferably, such copolymers comprise about 90–99% 3HB and about 1–10% 3HV. P(3HB-co-3HV) copolymers comprising about 4%, about 8%, and about 12% 3HV on a weight basis possess properties that have made them commercially attractive for particular applications. One skilled in the art can modify P(3HB-co-3HV) copolymers of the present invention by physical or chemical means to produce copolymer derivatives having desirable properties different from those of the plant- or microbially-produced copolymer.

Optimization of P(3HB-co-3HV) copolymer production by the methods discussed herein is expected to result in yields of copolymer in the range of from at least about 1% to at least about 20% of the fresh weight of the plant tissue, organ, or structure in which it is produced. In bacteria, yields in the range of from at least about 1% to at least about 90% of cell dry weight is expected.

Plastid Targeting of Expressed Enzymes for PHA Biosynthesis

PHA polymer can be produced in plants either by expression of the appropriate enzymes in the cytoplasm (Poirier et al., 1992) by the methods described above, or more preferably, in plastids, where higher levels of PHA production can be achieved (Nawrath et al., 1994). As demonstrated by the latter group, targeting of β-ketothiolase, acetoacetyl-CoA reductase, and PHB synthase to plastids of *Arabidopsis thaliana* results in the accumulation of high levels of PHB in the plastids without any readily apparent deleterious effects on plant growth and seed production. As branched-chain amino acid biosynthesis occurs in plant plastids (Bryan, 1980; Galili, 1995), overexpression therein of plastid-targeted enzymes, including a deregulated form of threonine deaminase, is expected to facilitate the production of elevated levels of α-ketobutyrate and propionyl-CoA. The latter can be condensed with acetyl-CoA by β-ketothiolase to form 3-ketovaleryl-CoA, which can then be further metabolized by a β-keto-acyl-CoA reductase to 3-hydroxyvaleryl-CoA, the precursor of the C5 subunit of P(3HB-co-3HV) copolymer. As there is a high carbon flux through acetyl-CoA in plastids, especially in seeds of oil-accumulating plants such as oilseed rape (*Brassica napus*), canola (*Brassica rapa, Brassica campestris, Brassica carinata,* and *Brassica juncea*), soybean (*Glycine max*), flax (*Linum usitatissimum*), and sunflower (*Helianthus annuus*) for example, targeting of the gene products of desired encoding DNAs to leucoplasts of seeds, or transformation of seed leucoplasts and expression therein of these encoding DNAs, are attractive strategies for achieving high levels of PHA biosynthesis in plants.

All of the enzymes discussed herein can be modified for plastid targeting by employing plant cell nuclear transformation constructs wherein DNA coding sequences of interest are fused to any of the available transit peptide sequences capable of facilitating transport of the encoded enzymes into plant plastids (partially summarized in von Heijne et al., 1991), and driving expression by employing an appropriate promoter. The sequences that encode a transit peptide region can be obtained, for example, from plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present invention are not critical as long as delivery into a plastid is obtained. Proteolytic processing within the plastid then produces the mature enzyme. This technique has proven successful not only with enzymes involved in PHA synthesis (Nawrath et al., 1994), but also with neomycin phosphotransferase II (NPT-II) and CP4 EPSPS (Padgette et al., 1995), for example.

Of particular interest are transit peptide sequences derived from enzymes known to be imported into the leucoplasts of seeds. Examples of enzymes containing useful transit peptides include those related to lipid biosynthesis (e.g., subunits of the plastid-targeted dicot acetyl-CoA carboxylase, biotin carboxylase, biotin carboxyl carrier protein, α-carboxy-transferase, plastid-targeted monocot multifunctional acetyl-CoA carboxylase (Mr, 220,000); plastidic subunits of the fatty acid synthase complex (e.g., acyl carrier protein (ACP), malonyl-ACP synthase, KASI, KASII, KASIII, etc.); steroyl-ACP desaturase; thioesterases (specific for short, medium, and long chain acyl ACP); plastid-targeted acyl transferases (e.g., glycerol-3-phosphate: acyl transferase); enzymes involved in the biosynthesis of aspartate family amino acids; phytoene synthase; gibberellic acid biosynthesis (e.g., ent-kaurene synthases 1 and 2); sterol biosynthesis (e.g., hydroxy methyl glutaryl-coA reductase); and carotenoid biosynthesis (e.g., lycopene synthase).

Exact translational fusions to the transit peptide of interest may not be optimal for protein import into the plastid. By creating translational fusions of any of the enzymes discussed herein to the precursor form of a naturally imported protein or C-terminal deletions thereof, one would expect that such translational fusions would aid in the uptake of the engineered precursor protein into the plastid. For example, Nawrath et al., (1994) used a similar approach to create the vectors employed to introduce the PHB biosynthesis genes of A. eutrophus into Arabidopsis.

It is therefore fully expected that targeting of the enzymes discussed in Examples 1–8 to leaf chloroplasts or seed plastids such as leucoplasts by fusing transit peptide gene sequences thereto will further enhance in vivo conditions for the biosynthesis of PHAs in plants.

Plastid Transformation for Expression of Enzymes Involved in PHA Biosynthesis Alternatively, enzymes facilitating the biosynthesis of metabolites such as threonine, α-ketobutyrate, propionyl-CoA, 3-ketovaleryl-CoA, 3-hydroxy-valeryl-CoA, and PHAs discussed herein can be expressed in situ in plastids by direct transformation of these organelles with appropriate recombinant expression constructs. Constructs and methods for stably transforming plastids of higher plants are well known in the art (Svab et al., 1990; Svab et al., 1993; Staub et al., 1993; Maliga et al., U.S. Pat. No. 5,451,513; PCT International Publications WO 95/16783, WO 95/24492, and WO 95/24493). These methods generally rely on particle gun delivery of DNA containing a selectable marker in addition to introduced DNA sequences for expression, and targeting of the DNA to the plastid genome through homologous recombination. Transformation of a wide variety of different monocots and dicots by particle gun bombardment is routine in the art (Hinchee et al., 1994; Walden and Wingender, 1995).

DNA constructs for plastid transformation generally comprise a targeting segement comprising flanking DNA sequences substantially homologous to a predetermined sequence of a plastid genome, which targeting segment enables insertion of DNA coding sequences of interest into the plastid genome by homologous recombination with said predetermined sequence; a selectable marker sequence, such as a sequence encoding a form of plastid 1 6S ribosomal RNA that is resistant to spectinomycin or streptomycin, or that encodes a protein which inactivates spectinomycin or streptomycin (such as the aadA gene), disposed within said targeting segment, wherein said selectable marker sequence confers a selectable phenotype upon plant cells, substantially all the plastids of which have been transformed with said DNA construct; and one or more DNA coding sequences of interest disposed within said targeting segment relative to said selectable marker sequence so as not to interfere with conferring of said selectable phenotype. In addition, plastid expression constructs also generally include a plastid promoter region and a transcription termination region capable of terminating transcription in a plant plastid, wherein said regions are operatively linked to the DNA coding sequences of interest.

A further refinement in chloroplast transformation/expression technology that facilitates control over the timing and tissue pattern of expression of introduced DNA coding sequences in plant plastid genomes has been described in PCT International Publication WO 95/16783. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced DNA coding sequence can be a single encoding region, or may contain a number of consecutive encoding sequences to be expressed as an engineered or synthetic operon. The latter is especially attractive where, as in the present invention, it is desired to introduce multigene biochemical pathways into plastids. This approach is not practical using standard nuclear transformation techniques since each gene introduced therein must be engineered as a monocistron, including an encoded transit peptide and appropriate promoter and terminator signals. Individual gene expression levels may vary widely among different cistrons, thereby possibly adversely affecting the overall biosynthetic process. This can be avoided by the chloroplast transformation approach.

Biosynthesis of Higher Poly(3-hydroxyalkanoate) Polymers in Plants

Biosynthesis of higher poly(3-hydroxyalkanoate) polymers in plants from medium chain length monomers (C6–C12) are possible based on information from the genetics and biochemistry of PHA formation in bacteria, combined with the knowledge of available plant metabolic intermediates. Examples of such pathway intermediates are those that are present during fatty acid biosynthesis and degradation, as well as intermediates formed through the biological processing of carbohydrates and amino acids. This knowledge for 3-hydroxyalkanoate formation in plants is well known in the art. For a general reference on monomers including $C_4$, $C_6$, $C_8$, . . . $C_{20}$, $C_{22}$, see van der Leij and Witholt (1995). Plants engineered to produce the corresponding monomers could be used in the inventive processes disclosed herein to afford a wide array of homo- and co-polymeric materials.

Biosynthesis of 4-hydroxybutyrate Containing Polymers in Plants

Poly(4-hydroxybutyrate) and copolymers of 4-hydroxybutyrate and other hydroxyalkanoates such as 3-hydroxybutyrate, 3-hydroxyvalerate, and 3-hydroxyhexanoate may be biosynthesized in plants capable of producing 4-hydroxybutyryl-CoA. Polymers containing 4-hydroxybutyrate are desirable due to their improved material properties, e.g. increased tensile strength, when compared to other short chain polyhydroxyalkanoates.

The substrate 4-hydroxybutyryl-CoA may be biosynthesized in plants by, for example, the *Clostridium kluyveri* pathway.

The genes involved in the conversion of succinate to 4-hydroxybutyrate in *Clostridium kluyveri* have been fully characterized (Sohling 1996). Succinate is first converted to succinyl-CoA by succinyl-CoA:acetyl-CoA CoA transferase. Next, succinyl-CoA is transformed to succinic acid semialdehyde by succinate semialdehyde dehydrogenase. The enzyme 4-hydroxybutyrate dehydrogenase acts to convert succinic acid semialdehyde to 4-hydroxybutyric acid, which is subsequently converted to 4-hydroxybutyryl-CoA by 4-hydroxybutyryl-CoA:acetyl-CoA CoA transferase. Transformation of a plant containing *Alcaligenes eutrophus* 3-polyhydroxybutyrate synthesis genes with the *Clostridium kluyveri* 4-hydroxybutyrate synthesis genes would afford a plant capable of producing the 4-hydroxybutyrate containing copolymers.

The available 4-hydroxybutyryl-CoA may be incorporated into polyhydroxyalkanoate polymers by a PHA synthase.

Control of Gene Expression in Plants

In the present invention it will likely be useful to control the level of one or more of the PHA enzymes to achieve the desired molecular weight (MW), molecular weight distribution or polydispersity (PDI) and PHA levels in recombinant plants or bacteria. There are several methods of regulating the expression of one or more enzymes in plants. For example, if high level protein expression is desired, one could choose a suitable promoter that has high levels of transcriptional activity, for example a plant viral promoter such as the 35S promoter (Odell et. al 1985.). High level transcription activity of promoters can also be found that express in certain tissue types or during certain stages of plant development for example seed storage protein promoters such as 7S (Doyle et. al. 1986). Transcriptional activity can also be modulated by overexpression of transcription factors that regulate promoters, or alternatively by removing a repressor that blocks transcription of a promoter.

Other methods for obtaining high level gene expression involve the use of plant viral vectors to deliver one or more genes of interest (Donson et. al., (1991); Champman et. al., (1992)). Viral RNA expression vectors have been developed to produce significant quantities of foreign proteins in plants. It would also be possible to use two different RNA virus vectors that can co-infect the same cells of a plant (i.e. potato virus Y (PVY) and potato virus X (PVX)). The use of two different viral RNA vectors could be used as a control point for modulating the expression levels of one or more of the specific protein of interest. For instance, if it is preferred to have a high level production of one protein, but low levels of another, then suitable viral RNA vectors can be constructed to achieve the desired expression levels of the proteins. These desired levels of proteins will be dictated by the relative transcriptional activity of the respective viral RNA vectors.

Another methods for achieving high level expression and translation of proteins is to optimize the amino acid codons specific to the target organism. By reconstructing the gene encoding the protein of interest with preferred amino acid codons typical of the target host organism, one can increase the level of translation of the protein of interest in plants. There are also other methods available for increasing the translatability of genes in plants including the use of introns and 5' untranslated leader sequences.

Organelle transformation, such as chloroplast (Boynton et. al., 1988; Svab et. al., 1990) and mitochondria transformation (Johnston et. al. 1988), has achieved high levels of expression (McBride et. al., 1995) of engineered proteins in plants since there are hundreds of copies of the chloroplast genome per cell thst would includey our engineered gene. This amplification of the number of copies of the gene, and the use of strong chloroplast promoters (i.e. prrn) usually results in high transcription and translation of the recombinant protein expression (McBride et. al., 1995). It is also possible to introduce several genes into the chloroplast genome as separate transcriptional units or as a typical bacterial operon (Staub and Maliga, 1995). In addition, inserting genes into the inverted repeat regions of the chloroplast genome results in the production of two copies of the introduced gene per chromosome, thus amplifying the expression even more.

In most cases, high level protein expression is desirable in the transgenic plants. However, there may be circumstances that high level protein expression is not desirable for every protein. For example, to achieve optimal PHA biosynthesis of desirable molecular weight and polydispersity it may be necessary to control the levels of the PHA production proteins. For instance, having high level protein production of the β-ketothiolase (i.e. PhbA or BktB) and the D-reductase (i. e. PhbB) and low level expression of the PHA synthase (i. e. PhbC) might result in the production of high molecular weight PHA of the desired polydispersity (Jun Sim et. al., 1997)

For example, one way to achieve high level expression of β-ketothiolase and D-reductase and low level expression of the PHA synthase would be to use strong promoters for the β-ketothiolase and D-reductase and a weaker promoter for the PHA synthase. It would also be possible to express the β-ketothiolase and D-reductase from a promoter that expresses early in seed development and express the PHA synthase from a promoter later in seed development. This might allow the metabolite required by the PHA synthase to build up in the plant cell and be immediately available for its use in PHA biosynthesis.

Another example would be to introduce the β-ketothiolase and D-reductase in the chloroplast genome and the PHA synthase in the nuclear genome. This would also achieve high expression of the β-ketothiolase and D-reductase and lower expression of the PHA synthase. Another strategy would be to insert the β-ketothiolase and D-reductase into the inverted repeat region of the chloroplast genome and the PHA synthase into a single copy region of the chloroplast genome. This would result in higher production of the β-ketothiolase and D-reductase and lower production of the PHA synthase.

Another method to increase expression of the β-ketothiolase and D-reductase would be to cross a homozygous plant line containing the β-ketothiolase, D-reductase, and PHA synthase with another homozygous plant line containing just the β-ketothiolase and D-reductase. This would result in two copies of the β-ketothiolase and D-reductase and one copy of the PHA synthase. This could also be achieved by genereating nuclear transformants of PHA synthase containing one copy of the gene (this can be determined by Southern blot analysis) and retransforming the plant by particle gun bombardment with expression plasmids containing β-ketothiolase and D-reductase and selecting lines containing multiple copies of the β-ketothiolase and/or D-reductase.

Finally, one could also alter the amino acid composition of the PHA synthase to be non-optimal for translation in the target plant or bacteria. This would result in poor translation of the protein and lower production levels of the PHA synthase protein. Alternatively, one could engineer in the PHA synthase protein signals that target the protein for rapid protein degradation (i.e. ubiquitin dependent degredation). This would also prevent the PHA synthase from accumulating to high levels in the plant.

Production of Transgenic Plants Comprising Genes for PHA Biosynthesis

Plant transformation vectors capable of delivering DNAs (genomic DNAs, plasmid DNAs, cDNAs, or synthetic DNAs) encoding PHA biosynthetic enzymes and other enzymes for optimizing substrate pools for PHA biosynthesis as discussed above in Examples 1–8 can be easily designed. Various strategies can be employed to introduce these encoding DNAs to produce transgenic plants capable of biosynthesizing high levels of PHAs, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.
2. Sequentially transforming plants with plasmids containing each of the encoding DNAs of interest, respectively.
3. Simultaneously cotransforming plants with plasmids containing each of the encoding DNAs, respectively.
4. Transforming plants with a single plasmid containing two or more encoding DNAs of interest.
5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al., 1994; PCT International Publication WO 93/02187). Similar strategies can be employed to produce bacterial host cells engineered for optimal PHA production.

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

Stability of Transgene Expression

As several overexpressed enzymes may be required to produce optimal levels of substrates for copolymer formation, the phenomenon of co-suppression may influence transgene expression in transformed plants. Several strategies can be employed to avoid this potential problem (Finnegan and McElroy, 1994).

One commonly employed approach is to select and/or screen for transgenic plants that contain a single intact copy of the transgene or other encoding DNA (Assaad et al., 1993; Vaucheret, 1993; McElroy and Brettell, 1994). Agrobacterium-mediated transformation technologies are preferred in this regard.

Inclusion of nuclear scaffold or matrix attachment regions (MAR) flanking a transgene has been shown to increase the level and reduce the variability associated with transgene expression in plants (Stief et al., 1989; Breyne et al., 1992; Allen et al., 1993; Mlynarova et al., 1994; Spiker and Thompson, 1996). Flanking a transgene or other encoding DNA with MAR elements may overcome problems associated with differential base composition between such transgenes or encoding DNAs and integrations sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs (Register et al., 1994). Site-specific recombination in which the endogenous copy of a gene is replaced by the same gene, but with altered expression characteristics, should obviate this problem (Yoder and Goldsbrough, 1994).

Any of the foregoing methods, alone or in combination, can be employed in order to insure the stability of transgene expression in transgenic plants of the present invention.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

REFERENCES CITED

Ainley et al., (1990) Plant Mol. Biol. 14: 949.
Allen et al., (1993) Plant Cell 5: 603.
Altschul et al., (1990) J. Mol. Biol. 215: 403.
Assaad et al., (1993) Plant Mol. Biol. 22: 1067.
Ausubel et al., (1989) Current Protocols in Molecular Biology, John Wiley & Sons, Inc.
Back et al., (1991) Plant Mol. Biol. 17: 9.
Becker et al., (1994) Plant J. 5: 299.
Bisswanger, (1981) J. Biol. Chem. 256: 815.
Bower and Birch, (1992) Plant J. 2: 409.
Boy etal.,(1979) Biochimie 61: 1151.
Boylan and Dekker, (1981) J. Biol. Chem. 256: 1809.
Boynton et. al., (1988) Science 240: 1534.
Bradford, (1976) Anal. Biochem. 72: 248.
Brandl et al., (1990) Adv. Biochem. Eng. Biotech. 41: 77.
Brandl et al., (1989) Int. J. Biol. Macromol. 11: 49.
Brandl, (1988) Appl. Environ. Microbiol 54: 1977.
Breyne et al., (1992) Plant Cell 4: 463.
Bright et al., (1983) CRC Crit. Rev. Plant Sci 1: 49.
Brosius,J.,(1989) DNA. 8:759
Bryan (1980) In: The Biochemistry of Plants, Volume 5, B. Miflin (Ed.) Academic Press, New York, p 403.
Bums, (1971) Methods Enzymol. 17B: 555.
Bums et al., (1988) Eur. J. Biochem. 176: 311.
Bustos et al., (1991) EMBO J. 10: 1469.
Byrom and Steinbüchel, (1991) WO 91/18995.
Byrom, (1987) Trends Biotechnol. 5: 246.

Bytebier et al., (1987) Proc. Natl. Acad. Sci. USA 84: 5345.
Calhoun, (1976) J. Bacteriol. 126: 56.
Camp and Randall, (1985) Plant Physiol. 77: 571.
Camp et al., (1988) Biochim. Biophys. Acta 933: 269.
Cassas et al., (1993) Proc. Natl. Acad. Sci. USA 90: 11212.
Castresana et al., (1988) EMBO J. 7: 1929.
Cattoir-Reynaerts et al., (1983) Biochem. Physiol. Pflanz. 178: 81.
Chang and Cronan, (1995) J. Biol. Chem. 270: 7896.
Changeux., (1961). Cold Spring Harbor Symp. Quant. Biol. 26: 313.
Champman et. al., (1992) *Plant J.* 2: 549.
Chilton et al., (1974) Proc. Natl. Acad. Sci. USA 71: 3672.
Christou (March/April, 1994) Agro Food Industry Hi Tech, p.17.
Cohen and Curran., (1990) Oncogene 5: 929.
Colau et al., (1987) Mol Cell Biol. 7: 2552
Colón et al., (1995) Appl. Microbiol. Biotechnol. 43: 482.
Coruzzi et al., (1984) EMBO J. 3: 1671.
Christou et al., (1991) Bio/Technology 9: 957.
Croy, (1993) In: Plant Molecular Biology Labfax, Hames and Rickwood (Eds.), BIOS Scientific Publishers Limited, Oxford, UK.
Czerny et al., (1993) Genes Dev 7: 2048.
Danchin et al., (1984) Mol. Gen. Genet. 193: 473.
Datta et al., (1987) Proc. Natl. Acad. Sci. USA 84: 393.
Davis et al., (1987) J. Biol. Chem. 262: 82.
Dawes and Senior, (1973) Adv. Microb. Physiol. 14: 135.
De la Pena et al., (1987) Nature 325: 274
Dennis, (1994) Intl. Symp. Bact. PHA, Abstr. 17, p. 43.
Ditta et al., (1980) Proc. Natl. Acad. Sci. USA. 77: 7347.
Doi, (1990) Bacterial Polyesters, VCH Publishers, Inc., New York.
Doi et al., (1986) J. Chem Soc. 23: 1696.
Donson et. al., (1991) *Proc Natl AcadSci*. 88: 7204.
Dotson et al., (1990) Planta 182: 546.
Doyle et al., (1986) J. Biol. Chem. 261: 9228.
Eisenreich et al., (1993) Eur. J. Biochem. 21: 619.
Eisenstadt et al., (1994) In: Methods for General and Molecular Bacteriology, P. Gerhardt, R. Murray, W. Wood, and N. Kreig (Eds.), ASM Press, Washington, D.C., p. 297.
Falco et al., (1995) Bio/Technology 13: 577.
Feinbaum et al., (1991) Mol. Gen. Genet. 226: 449.
Feldberg and Datta, (1971) Eur. J. Biochem. 21: 438.
Feldman and Datta, (1975) Biochemistry 14: 1760.
Feldmann et al., (1994) In: Arabidopsis, Meyerowitz and Somerville (Eds.), Cold Spring Harbor Laboratory Press, Cold Spring Harbor, N.Y., p. 137.
Finnegan and McElroy, (1994) Bio/Technology 12: 883.
Fisher and Eisenstein, (1993) J. Bacteriol. 175: 6605.
Fisk and Dandekar, (1993) Scientia Horticulturae 55: 5.
Fosket, (1994) Plant Growth and Development, Academic Press, Inc., San Diego, p. 132.
Fraley et al., (1983) Proc. Natl. Acad. Sci USA. 80: 4803.
Frankard et al., (1991) Theor. Appl. Genet. 82: 273.
Fries, (1962) Physiol. Plant. 15: 566.
Fromm et al., (1990) Bio/Technology 8: 833.
Fry et al., (1987) Plant Cell Reports 6: 321.
Galili, (1995) Plant Cell 7: 899.
Gasser and Fraley, (1989) Science 244: 1293.
Glick et al., (1993) Methods in Plant Molecular Biology and Biotechnology, CRC Press, Boca Raton, Fla.
Gordon-Kamm et al., (1990) Plant Cell 2: 603.
Goss and Datta, (1985) Mol. Gen. Genet. 201: 308.
Gruys et al., (1989) Biochemistry 28: 9071–9080.
Halarnkar et al., (1988) Phytochemistry 27: 997.
Halarnkar and Blomquist, (1989) Comp. Biochem. Physiol. 92: 227.
Haywood et al., (1988a) FEMS Microbiol. Lett. 52: 259.
Haywood et al., (1988b) FEMS Microbiol. Lett. 52: 91.
Haywood, (1989) FEMS Microbiol Lett. 57: 1.
Hibberd et al., (1980) Planta 148: 183.
Hinchee et al., (1988) Bio/Technology 6: 915.
Hinchee et al., (1994) In: Plant Cell and Tissue Culture, I. Vasil and T. Thorpe (Eds.), Kluwer Academic Publishers, Netherlands, p. 231.
Hoffman, U.S. Pat. No. 5,106,739
Horn et al., (1988) Plant Cell Rep. 7: 469.
Horsch et al., (1985) Science 227: 1229.
Hunkapiller et al., (1983) Methods Enzymol. 91: 399.
Jan et al., (1995) Analytical Biochemistry 225: 258.
Jetten et al., (1995) Appl. Microbiol. Biotechnol. 43: 76.
Jetten and Sinskey, (1995) Critical Rev. Biotechnol. 15: 73.
John and Keller, (1996) Proc. Natl. Acad. Sci. U.S.A. 93: 12768.
Johnston et. al., (1988) *Science* 240: 1538.
Jun Sim et. al., (1997) *Nature Biotechnology* 15: 63
Karchi et al., (1993) Plant J. 3: 721.
Kares et al., (1990) Plant Mol. Biol. 15: 905.
Katake and Ono, (1964) Shokukin Eiseigku Zasshi 5: 39.
Kidwell et al., (1995) Appl. Environ. Microbiol. 61: 1391.
Kim and Patel, (1992) J. Biol. Chem. 267: 5128.
Knutzon et al., (1992) Proc. Natl. Acad. Sci USA 89: 2624.
Koncz and Shell, (1986) Mol. Gen. Genet. 204: 283.
Kovach, M. et al. (1994) Biotechniques. 16:800.
Koziel et al., (1993) Bio/Technology 11: 194.
Kridl et al., (1991) Seed Sci. Res. 1: 209.
Kuhlemeier et al., (1989) Plant Cell 1: 471.
Lam and Chua, (1990) Science 248: 471.
Lam and Chua, (1991) J. Biol. Chem. 266: 17131
LaRossa, (1987) J. Bacteriol. 169: 1372.
Laties and Hoell, (1967) Phytochemistry 6: 49.
Lawther et al., (1987) Nucl. Acids Res. 15: 2137.
Layman, (Oct. 31, 1994) Chem. & Eng. News, p. 10.
Lee et al., (1995) J. Fermentation and Bioengineering 79: 177.
Lemoigne, (1926) Bull. Soc. Chim. Biol. (Paris) 8: 770.
Lindsay, (1992) Modern Plastics 2: 62.
Lowe et al., (1983) Biochem. J. 215: 133.
Luo and Wu, (1988) Plant Mol. Biol. Rep. 6: 165.
Maliga et al., U.S. Pat. No. 5,451,513.
Maliga et al., PCT International Publication WO 95/16783.
Maliga et al., PCT International Publication WO 95/24492.
Maliga et al., PCT International Publication WO 95/24493.
Manchak and Page, (1994) Microbiology 140: 953.
Marcus and Dekker, (1993) Biochimica et Biophysica Acta 1164: 299.
Masamune et al., (1989) Pure & Appl. Chem. 6: 303.
Masoud, et al., (1996) Transgen. Res. 5: 313.
McBride et. al., (1995) *Biotechnology* 13: 362.
McElroy and Brettell, (1994) TIBTECH 12: 62.
Miller and Schulz, (1993) Science 259: 965.
Möckel et al., (1994) Molec. Microbiol. 13: 833.
Monod et al., (1963) J. Mol. Biol. 6: 306.
Morelli et al., (1985) Nature 315: 200.
Motoyama et al., (1994) Appl. Microbiol. Biotech. 42: 67.
Mourad and King, (1995) Plant Physiol. 107: 43
Mlynarova et al., (1994) Plant Cell 6: 417.
Muhitch, (1995) Plant Physiol. 108 (2 Suppl.): 71.
Murashige and Skoog, (1962) Physiol. Plant. 15: 473.
Nakamura et al., (1992) Int. J. Biol. Macromol. 14: 321.
Nakamura et al., (1991) Macromol. Rep. A28 (Suppl. 1): 15.
Nawrath et al., (1994) Proc. Natl. Acad. Sci USA 91: 12760.

Odel let al.,(1985)Nature 313: 810.
Ou-Lee et al., (1986) Proc. Natl. Acad. Sci USA 83: 6815.
Padgette et al., (1996) In: Herbicide Resistant Crops: Agricultural, Environmental, Economic, Regulatory, and Technical Aspects. S. O. Duke (Ed.), CRC Press, N.Y., p. 53.
Padgette et al., (1995) Crop Sci. 35: 1451.
Patel and Walt, (1987) J. Biol. Chem. 262: 7132.
Patel and Agnew, (1988) Arch. Microbiol. 150:267–271.
Peoples and Sinskey, (1989a) J. Biol. Chem. 264: 15293.
Peoples and Sinskey, (1989b) J. Biol. Chem. 264: 15298.
Petrosyan et al., (1969) Vopr. Bikrobiol. 181.
Pettit et al., (1978) Proc. Nat. Acad. Sci. USA 75: 4881.
Poirier et al., (1992) Science 256: 520.
Poirier et al., (1995a) Bio/Technology 13: 142.
Poirier et al., (1995b) Int. J. Biol. Macromol. 17: 7.
Poston, (1977) Science 195: 301.
Poston., (1978) Phytochemistry 17: 401.
Potrykus, (1991) Annu. Rev. Plant Physiol. Plant Mol. Biol. 42: 205.
Priefert and Steinbüchel (1992) J. Bact. 174: 6590
Qureshi et al., (1982) J. Chrom. 249: 333.
Radke et al., (1988) Theor. Appl. Genet. 75: 685.
Register et al., (1994) Plant Mol. Biol. 25: 951.
Reed and Willms (1966) Methods Enzymol. 9: 247–265.
Rhodes et al., (1988) Science 240: 204.
Richins et al., (1987) NAR 20: 8451.
Rodriguez et al., (1988) Vectors: A Survey of Molecular Cloning Vectors and Their Uses, Butterworths, Boston.
Sambrook et al., (1989) Molecular Cloning: A Laboratory Manual, Second Edition, Cold Spring Harbor Laboratory Press, Cold Spring Harbor, N.Y.
Schubert et al., (1988) J. Bacteriol. 170: 5837.
Schulz (1974) J. Biol. Chem. 249: 2704.
Schulze et al., (1992) Eur. J. Biochem. 206: 427.
Schulze et al., (1993) Eur. J. Biochem. 211: 591.
Schulze-Lefert et al., (1989) EMBO J. 8: 651.
Shah et al., (1986) Science 233: 478.
Shaner and Singh, (1993) Plant Physiol 103: 1221.
Shaul and Galili, (1992a) Plant Physiol. 100: 1157.
Shaul and Galili, (1992b) Plant J. 2: 203.
Shaul and Galili, (1993) Plant Mol. Biol. 23: 759.
Shizuta and Tokushige, (1971) Methods Enzymol. 17: 575.
Shizuta and Hayashi, (1975) Curr. Topics Cell. Reg. 11: 99.
Sim et al., (1997) Nature Biotechnol. 15: 63.
Slater et al., (1988). J. Bacteriol. 170: 4431.
Slater et al., (1992) Appl. Environ. Microbiol. 58: 1089.
Slighton and Beachy, (1987) Planta 172: 356.
Somers et al., (1992) Bio/Technology 10: 1589.
Speckhard and Frey, (1975) Biochem. Biophys. Res. Commun. 62: 614–620.
Spiker and Thompson, (1996) Plant Physiol. 110: 15.
Staba, E. J., (1969) Recent Advances in Phytochemistry, Vol. 2, Seikel et al. (Eds.), Appleton Century Crofts, N.Y.
Stark et al., (1992) Science 258: 287.
Staub and Maliga, (1993) EMBO J. 12: 601.
Staub and Maliga, (1995) *Plant J* 7: 845.
Stayton et al., (1991) Aust. J. Plant. Physiol. 18: 507.
Stief et al., (1989) Nature 341: 343.
Steinbüchel, (1991) In: Biomaterials, D. Byrom (Ed.), MacMillan, Basingstoke, pp. 123–213.
Steinbüchel and Pieper, (1992) Appl. Microbiol. Biotechnol. 37: 1.
Steginsky et al., (1985) J. Biol. Chem. 260: 13690.
Strauss et al., (1985) Planta 163: 554.
Svab and Maliga, (1993) Proc. Natl. Acad. Sci. USA 90: 913.
Svab et al., (1990) Proc. Natl. Acad. Sci. USA 87: 8526.
Taillon et al., (1988) Gene 63: 245.
Tholozan et al., (1992) Arch. Microbiol. 157: 249.
Tholozan et al., (1994) Arch. Microbiol. 162: 401.
Tombolini et al., (1995) Microbiology 141: 2553.
Toriyama et al., (1988) Bio/Technology 6: 10.
Van den Broeck et al., (1985) Nature 313: 358.
van der Leij and Witholt, (1995) Can. J. Microbiol. 41(Suppl. 1): 222.
Van Dyk and LaRossa (1987) Mol. Gen. Genet. 207: 435.
Vasil et al., (1992) Bio/Technology 10:667
Vaucheret, (1993) C.R. Acad. Sci. Paris, Science de la vie/Life Sciences 316: 1471.
Von Heijne et al., (1991) Plant Mol. Biol. Rep. 9: 104.
Walker (1987) In: *Eschericia coli* and *Salmonella typhimurium*: Cellular and Molecular Biology, F. C. Neidhart et al. (Eds.), American Society for Microbiology, Washington, D.C., pp. 13346–1357.
Weisshaar et al., (1991) EMBO J. 10: 1777.
Williams et al., (1994) Appl. Microbiol. Biotechnol. 40: 717.
Walden and Wingender, (1995) TIBS 13: 324.
Wallis, (1994) J. Mol. Biol. 236: 209.
Wan and Lemaux, (1994) Plant Physiol. 104: 37
Wang et al., (1992) Bio/Technology 10: 691.
Weeks et al., (1993) Plant Physiol. 102: 1077.
Yamnaguchi-Shinozaki et al., (1990) Plant Mol. Biol. 15: 905.
Yoder and Goldsbrough, (1 994) Bio/Technol. 12: 263–267.
Yoon et al., (1995) J. Ferment. Bioeng. 80: 350
Zhang et al., (1994) Appl. Environ. Microbiol. 60: 1198–1205.
Zhang and Wu, (1988) Theor. Appl. Genet. 76: 835.
Zhang et al., (1988) Plant Cell Rep. 7: 379.
Zhong et al., (1993) Plant Cell Rep. 13: 1.
Zinszner et al., (1994) Genes Dev. 8: 2513.

We claim:

1. A method for generating a transformed plant which produces a polyhydroxyalkanoate polymer having a single mode molecular weight distribution, comprising the steps of:
    (a) inserting into plant cells a nucleic acid molecule encoding a β-ketoacyl reductase, a nucleic acid molecule encoding a β-ketothiolase, and a nucleic acid molecule encoding a polyhydroxyalkanoate synthase to produce transformed plant cells, wherein the transformed plant cells comprise a single copy of the nucleic acid molecule encoding a polyhydroxyalkanoate synthase;
    (b) isolating transformed plant cells;
    (c) regenerating the transformed plant cells to form transformed plants; and
    (d) selecting a transformed plant which produces a polyhydroxyalkanoate polymer having a single mode molecular weight distribution; wherein the molecular weight distribution is between about 2 and about 4.

2. The method of claim 1, wherein the nucleic acid molecule encoding a β-ketoacyl reductase, the nucleic acid molecule encoding a β-ketothiolase, and the nucleic acid molecule encoding a polyhydroxyalkanoate synthase are *Alcaligenes eutrophus, Alcaligenes faecalis*, Aphanothece sp., *Azotobacter vinelandii, Bacillus cereus, Bacillus megaterium, Beijerinkia indica, Derxia gummosa*, Methylobacterium sp., Microcoleus sp., *Nocardia corallina, Pseudomonas cepacia, Pseudomonas extorquens, Pseudomonas oleovorans, Rhodobacter sphaeroides, Rhodobacter capsulatus, Rhodospirillum rubrum*, or *Thiocapsa pfennigii* nucleic acid molecules.

3. The method of claim 2, wherein the nucleic acid molecule encoding a β-ketoacyl reductase, the nucleic acid molecule encoding a β-ketothiolase, and the nucleic acid molecule encoding a polyhydroxyalkanoate synthase are *Alcaligenes eutrophus* nucleic acid molecules.

4. The method of claim 1, wherein the polyhydroxyalkanoate polymer is a homopolymer or copolymer of 3-hydroxybutyrate, 3-hydroxyhexanoate, 3-hydroxyoctanoate, 3-hydroxydecanoate, 3-hydroxydodecanoate, 3-hydroxytetradecanoate, 3-hydroxyhexadecanoate, 3-hydroxyoctadecanoate, 3-hydroxyeicosanoate, or 3-hydroxydocosanoate.

5. The method of claim 1, wherein the polyhydroxyalkanoate polymer is a homopolymer.

6. The method of claim 5, wherein the homopolymer is poly(3-hydroxybutyrate) or poly(4-hydroxybutyrate).

7. The method of claim 1, wherein the polyhydroxyalkanoate polymer is a copolymer.

8. The method of claim 7, wherein the copolymer is poly(3-hydroxybutyrate-co-3-hydroxyvalerate), poly(3-hydroxybutyrate-co-4-hydroxybutyrate), poly(3-hydroxybutyrate-co-3-hydroxyhexanoate), poly(4-hydroxybutyrate-co-3-hydroxyhexanoate), or poly(3-hydroxybutyrate-co-4-hydroxybutyrate-co-3-hydroxyhexanoate).

9. The method of claim 1, wherein the molecular weight distribution is about 2.5.

10. The method of claim 1, wherein the molecular weight distribution is about 2.1.

11. The method of claim 1, wherein the polyhydroxyalkanoate polymer has a number average molecular weight between about 100,000 and about 300,000.

12. The method of claim 1, wherein the plant cell is tobacco, wheat, potato, Arabidopsis, corn, soybean, canola, oil seed rape, sunflower, flax, peanut, sugarcane, swtichgrass, or alfalfa.

13. The method of claim 1, wherein step (a) further comprises inserting into the plant cells a nucleic acid molecule encoding succinyl-CoA:acetyl-CoA transferase, succinate semialdehyde dehydrogenase, 4-hydroxybutyrate dehydrogenase, or hydroxybutyryl-CoA:acetyl-CoA transferase.

14. The method of claim 1, further comprising the step of producing a daughter plant from the transformed plant.

15. The method of claim 1, further comprising the step of producing a homozygous daughter plant from the transformed plant.

16. The method of claim 1, further comprising the step of preparing a plant extract from the transformed plant, wherein the plant extract comprises a polyhydroxyalkanoate polymer.

17. The method of claim 16, further comprising the step of isolating the polyhydroxyalkanoate polymer from the plant extract.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 1545 base pairs
        (B) TYPE: nucleic acid
        (C) STRANDEDNESS: double (D) TOPOLOGY: linear (ii) MOLECULE TYPE: DNA (genomic)

(xi) SEQUENCE DESCRIPTION: SEQ ID NO:1:

ATGGCTGACT CGCAACCCCT GTCCGGTGCT CCGGAAGGTG CCGAATATTT AAGAGCAGTG        60

CTGCGCGCGC CGGTTTACGA GGCGGCGCAG GTTACGCCGC TACAAAAAAT GGAAAAACTG       120

TCGTCGCGTC TTGATAACGT CATTCTGGTG AAGCGCGAAG ATCGCCAGCC AGTGCACAGC       180

TTTAAGCTGC GCGGCGCATA CGCCATGATG GCGGGCCTGA CGGAAGAACA GAAAGCGCAC       240

GGCGTGATCA CTGCTTCTGC GGGTAACCAC GCGCAGGGCG TCGCGTTTTC TTCTGCGCGG       300

TTAGGCGTGA AGGCCCTGAT CGTTATGCCA ACCGCCACCG CCGACATCAA AGTCGACCGG       360

CTGCGCGGCT TCGGCGGCGA AGTGCTGCTC CACGGCGCGA ACTTTGATGA AGCGAAACGC       420

AAAGCGATCG AACTGTCACA GCAGCAGGGG TTCACCTGGG TGCCGCCGTT CGACCATCCG       480

ATGGTGATTG CCGGGCAAGG CACGCTGGCG CTGGAACTGC TCCAGCAGGA CGCCCATCTC       540

GACCGCGTAT TTGTGCCAGT CGGCGGCGGC GGTCTGGCTG CTTGCGTGGC GGTGCTGATC       600

AAACAACTGA TGCCGCAAAT CAAAGTGATC GCCGTAGAAG CGGAAGACTC CGCCTGCCTG       660

AAAGCAGCGC TGGATGCGGG TCATCCGGTT GATCTGCCGC GCGTAGGGCT ATTTGCTGAA       720

GGCGTAGCGG TAAAACGCAT CGGTGACGAA ACCTTCCGTT TATGCCAGGA GTATCTCGAC       780

GACATCATCA CCGTCGATAG CGATGCGATC TGTGCGGCGA TGAAGGATTT ATTCGAAGAT       840

GTGCGCGCGG TGGCGGAACC CTCTGGCGCG CTGGCGCTGG CGGGAATGAA AAAATATATC       900

GCCCTGCACA ACATTCGCGG CGAACGGCTG GCGCATATTC TTTCCGGTGC CAACGTGAAC       960

TTCCACGGCC TGCGCTACGT CTCAGAACGC TGCGAACTGG TCGAACAGCG TGAAGCGTTG      1020

TTGGCGGTGA CCATTCCGGA AGAAAAAGGC AGCTTCCTCA AATTCTGCCA ACTGCTTGGC      1080

GGGCGTTCGG TCACCGAGTT CAACTACCGT TTTGCCGATG CCAAAAACGC CTGCATCTTT      1140

GTCGGTGTGC GCCTGAGCCG CGGCCTCGAA GAGCGCAAAG AAATTTTGCA GATGCTCAAC      1200

GACGGCGGCT ACAGCGTGGT TGATCTCTCC GACGACGAAA TGGCGAAGCT ACACGTGCGC      1260

TATATGGTCG GCGGACGTCC ATCGCATCCG TTGCAGGAAC GCCTCTACAG CTTCGAATTC      1320

CCGGAATCAC CGGGCGCGCT GCTGCGCTTC CTCAACACGC TGGGTACGTA CTGGAACATT      1380

TCTTTGTTCC ACTATCGCAG CCATGGCACC GACTACGGGC GCGTACTGGC GGCGTTCGAA      1440

CTTGGCGACC ATGAACCGGA TTTCGAAACC CGGCTGAATG AGCTGGGCTA CGATTGCCAC      1500

GACGAAACCA ATAACCCGGC GTTCAGGTTC TTTTTGGCGG GTTAA                     1545

(2) INFORMATION FOR SEQ ID NO:2:

(i) SEQUENCE CHARACTERISTICS:
         (A) LENGTH: 46 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:2:

TTTTTGGATC CGATATCTTA ACCCGCCAAA AAGAACCTGA ACGCCG                       46

(2) INFORMATION FOR SEQ ID NO:3:

(i) SEQUENCE CHARACTERISTICS:
         (A) LENGTH: 37 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:3:

TTTTTGGATC CATGGCTGAC TCGCAACCCC TGTCCGG                                37

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:4:

CAGCTTCGAG TTCCCGGAAT CACCGGGCGC GTTCCTGCGC TTCC                        44

(2) INFORMATION FOR SEQ ID NO:5:

(i) SEQUENCE CHARACTERISTICS:
        (A) LENGTH: 1545 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

ATGGCTGACT CGCAACCCCT GTCCGGTGCT CCGGAAGGTG CCGAATATTT AAGAGCAGTG       60

CTGCGCGCGC CGGTTTACGA GGCGGCGCAG GTTACGCCGC TACAAAAAAT GGAAAAACTG      120

TCGTCGCGTC TTGATAACGT CATTCTGGTG AAGCGCGAAG ATCGCCAGCC AGTGCACAGC      180

TTTAAGCTGC GCGGCGCATA CGCCATGATG GCGGGCCTGA CGGAAGAACA GAAAGCGCAC      240

GGCGTGATCA CTGCTTCTGC GGGTAACCAC GCGCAGGGCG TCGCGTTTTC TTCTGCGCGG      300

TTAGGCGTGA AGGCCCTGAT CGTTATGCCA ACCGCCACCG CCGACATCAA AGTCGACCGG      360

CTGCGCGGCT TCGGCGGCGA AGTGCTGCTC CACGGCGCGA ACTTTGATGA AGCGAAACGC      420

AAAGCGATCG AACTGTCACA GCAGCAGGGG TTCACCTGGG TGCCGCCGTT CGACCATCCG      480

ATGGTGATTG CCGGGCAAGG CACGCTGGCG CTGGAACTGC TCCAGCAGGA CGCCCATCTC      540

GACCGCGTAT TTGTGCCAGT CGGCGGCGGC GGTCTGGCTG CTTGCGTGGC GGTGCTGATC      600

AAACAACTGA TGCCGCAAAT CAAAGTGATC GCCGTAGAAG CGGAAGACTC CGCCTGCCTG      660

AAAGCAGCGC TGGATGCGGG TCATCCGGTT GATCTGCCGC GCGTAGGGCT ATTTGCTGAA      720

GGCGTAGCGG TAAAACGCAT CGGTGACGAA ACCTTCCGTT TATGCCAGGA GTATCTCGAC      780

GACATCATCA CCGTCGATAG CGATGCGATC TGTGCGGCGA TGAAGGATTT ATTCGAAGAT      840

GTGCGCGCGG TGGCGGAACC CTCTGGCGCG CTGGCGCTGG CGGGAATGAA AAAATATATC      900

GCCCTGCACA ACATTCGCGG CGAACGGCTG GCGCATATTC TTTCCGGTGC CAACGTGAAC      960

TTCCACGGCC TGCGCTACGT CTCAGAACGC TGCGAACTGG TCGAACAGCG TGAAGCGTTG     1020

TTGGCGGTGA CCATTCCGGA AGAAAAAGGC AGCTTCCTCA AATTCTGCCA ACTGCTTGGC     1080

GGGCGTTCGG TCACCGAGTT CAACTACCGT TTTGCCGATG CCAAAAACGC CTGCATCTTT     1140

GTCGGTGTGC GCCTGAGCCG CGGCCTCGAA GAGCGCAAAG AAATTTTGCA GATGCTCAAC     1200

```
GACGGCGGCT ACAGCGTGGT TGATCTCTCC GACGACGAAA TGGCGAAGCT ACACGTGCGC     1260

TATATGGTCG GCGGACGTCC ATCGCATCCG TTGCAGGAAC GCCTCTACAG CTTCGAGTTC     1320

CCGGAATCAC CGGGCGCGTT CCTGCGCTTC CTCAACACGC TGGGTACGTA CTGGAACATT     1380

TCTTTGTTCC ACTATCGCAG CCATGGCACC GACTACGGGC GCGTACTGGC GGCGTTCGAA     1440

CTTGGCGACC ATGAACCGGA TTTCGAAACC CGGCTGAATG AGCTGGGCTA CGATTGCCAC     1500

GACGAAACCA ATAACCCGGC GTTCAGGTTC TTTTTGGCGG GTTAA                    1545

(2) INFORMATION FOR SEQ ID NO:6:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

TATCGCAGCC ACGGCACCGA CTACGGGCGC GTACTGGCGG CGTTCGAATT TGGCGACCAT       60

GAACC                                                                   65

(2) INFORMATION FOR SEQ ID NO:7:

(i) SEQUENCE CHARACTERISTICS:
        (A) LENGTH: 1545 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

ATGGCTGACT CGCAACCCCT GTCCGGTGCT CCGGAAGGTG CCGAATATTT AAGAGCAGTG       60

CTGCGCGCGC CGGTTTACGA GGCGGCGCAG GTTACGCCGC TACAAAAAAT GGAAAAACTG      120

TCGTCGCGTC TTGATAACGT CATTCTGGTG AAGCGCGAAG ATCGCCAGCC AGTGCACAGC      180

TTTAAGCTGC GCGGCGCATA CGCCATGATG GCGGGCCTGA CGGAAGAACA GAAAGCGCAC      240

GGCGTGATCA CTGCTTCTGC GGGTAACCAC GCGCAGGGCG TCGCGTTTTC TTCTGCGCGG      300

TTAGGCGTGA AGGCCCTGAT CGTTATGCCA ACCGCCACCG CCGACATCAA AGTCGACCGG      360

CTGCGCGGCT TCGGCGGCGA AGTGCTGCTC CACGGCGCGA ACTTTGATGA AGCGAAACGC      420

AAAGCGATCG AACTGTCACA GCAGCAGGGG TTCACCTGGG TGCCGCCGTT CGACCATCCG      480

ATGGTGATTG CCGGGCAAGG CACGCTGGCG CTGGAACTGC TCCAGCAGGA CGCCCATCTC      540

GACCGCGTAT TTGTGCCAGT CGGCGGCGGC GGTCTGGCTG CTTGCGTGGC GGTGCTGATC      600

AAACAACTGA TGCCGCAAAT CAAAGTGATC GCCGTAGAAG CGGAAGACTC CGCCTGCCTG      660

AAAGCAGCGC TGGATGCGGG TCATCCGGTT GATCTGCCGC GCGTAGGGCT ATTTGCTGAA      720

GGCGTAGCGG TAAAACGCAT CGGTGACGAA ACCTTCCGTT TATGCCAGGA GTATCTCGAC      780

GACATCATCA CCGTCGATAG CGATGCGATC TGTGCGGCGA TGAAGGATTT ATTCGAAGAT      840

GTGCGCGCGG TGGCGGAACC CTCTGGCGCG CTGGCGCTGG CGGGAATGAA AAAATATATC      900

GCCCTGCACA ACATTCGCGG CGAACGGCTG GCGCATATTC TTTCCGGTGC CAACGTGAAC      960

TTCCACGGCC TGCGCTACGT CTCAGAACGC TGCGAACTGG TCGAACAGCG TGAAGCGTTG     1020

TTGGCGGTGA CCATTCCGGA AGAAAAAGGC AGCTTCCTCA AATTCTGCCA ACTGCTTGGC     1080
```

```
GGGCGTTCGG TCACCGAGTT CAACTACCGT TTTGCCGATG CCAAAAACGC CTGCATCTTT     1140

GTCGGTGTGC GCCTGAGCCG CGGCCTCGAA GAGCGCAAAG AAATTTTGCA GATGCTCAAC     1200

GACGGCGGCT ACAGCGTGGT TGATCTCTCC GACGACGAAA TGGCGAAGCT ACACGTGCGC     1260

TATATGGTCG GCGGACGTCC ATCGCATCCG TTGCAGGAAC GCCTCTACAG CTTCGAATTC     1320

CCGGAATCAC CGGGCGCGCT GCTGCGCTTC CTCAACACGC TGGGTACGTA CTGGAACATT     1380

TCTTTGTTCC ACTATCGCAG CCACGGCACC GACTACGGGC GCGTACTGGC GGCGTTCGAA     1440

TTTGGCGACC ATGAACCGGA TTTCGAAACC CGGCTGAATG AGCTGGGCTA CGATTGCCAC     1500

GACGAAACCA ATAACCCGGC GTTCAGGTTC TTTTTGGCGG GTTAA                    1545

(2) INFORMATION FOR SEQ ID NO:8:

(i) SEQUENCE CHARACTERISTICS:
         (A) LENGTH: 1545 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:8:

ATGGCTGACT CGCAACCCCT GTCCGGTGCT CCGGAAGGTG CCGAATATTT AAGAGCAGTG       60

CTGCGCGCGC CGGTTTACGA GGCGGCGCAG GTTACGCCGC TACAAAAAAT GGAAAAACTG     120

TCGTCGCGTC TTGATAACGT CATTCTGGTG AAGCGCGAAG ATCGCCAGCC AGTGCACAGC     180

TTTAAGCTGC GCGGCGCATA CGCCATGATG GCGGGCCTGA CGGAAGAACA GAAAGCGCAC     240

GGCGTGATCA CTGCTTCTGC GGGTAACCAC GCGCAGGGCG TCGCGTTTTC TTCTGCGCGG     300

TTAGGCGTGA AGGCCCTGAT CGTTATGCCA ACCGCCACCG CCGACATCAA AGTCGACCGG     360

CTGCGCGGCT TCGGCGGCGA AGTGCTGCTC ACGGCGCGCA ACTTTGATGA AGCGAAACGC     420

AAAGCGATCG AACTGTCACA GCAGCAGGGG TTCACCTGGG TGCCGCCGTT CGACCATCCG     480

ATGGTGATTG CCGGGCAAGG CACGCTGGCG CTGAACTGC TCCAGCAGGA CGCCCATCTC      540

GACCGCGTAT TTGTGCCAGT CGGCGGCGGC GGTCTGGCTG CTTGCGTGGC GGTGCTGATC     600

AAACAACTGA TGCCGCAAAT CAAAGTGATC GCCGTAGAAG CGGAAGACTC CGCCTGCCTG     660

AAAGCAGCGC TGGATGCGGG TCATCCGGTT GATCTGCCGC GCGTAGGGCT ATTTGCTGAA     720

GGCGTAGCGG TAAAACGCAT CGGTGACGAA ACCTTCCGTT TATGCCAGGA GTATCTCGAC     780

GACATCATCA CCGTCGATAG CGATGCGATC TGTGCGGCGA TGAAGGATTT ATTCGAAGAT     840

GTGCGCGCG TGGCGGAACC CTCTGGCGCG CTGGCGCTGG CGGGAATGAA AAAATATATC      900

GCCCTGCACA ACATTCGCGG CGAACGGCTG GCGCATATTC TTTCCGGTGC CAACGTGAAC     960

TTCCACGGCC TGCGCTACGT CTCAGAACGC TGCGAACTGG TCGAACAGCG TGAAGCGTTG    1020

TTGGCGGTGA CCATTCCGGA AGAAAAAGGC AGCTTCCTCA AATTCTGCCA ACTGCTTGGC    1080

GGGCGTTCGG TCACCGAGTT CAACTACCGT TTTGCCGATG CCAAAAACGC CTGCATCTTT    1140

GTCGGTGTGC GCCTGAGCCG CGGCCTCGAA GAGCGCAAAG AAATTTTGCA GATGCTCAAC    1200

GACGGCGGCT ACAGCGTGGT TGATCTCTCC GACGACGAAA TGGCGAAGCT ACACGTGCGC    1260

TATATGGTCG GCGGACGTCC ATCGCATCCG TTGCAGGAAC GCCTCTACAG CTTCGAGTTC    1320

CCGGAATCAC CGGGCGCGTT CCTGCGCTTC CTCAACACGC TGGGTACGTA CTGGAACATT    1380

TCTTTGTTCC ACTATCGCAG CCACGGCACC GACTACGGGC GCGTACTGGC GGCGTTCGAA    1440

TTTGGCGACC ATGAACCGGA TTTCGAAACC CGGCTGAATG AGCTGGGCTA CGATTGCCAC    1500
```

```
GACGAAACCA ATAACCCGGC GTTCAGGTTC TTTTTGGCGG GTTAA                  1545

(2) INFORMATION FOR SEQ ID NO:9:

(i) SEQUENCE CHARACTERISTICS:
        (A) LENGTH: 1185 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

ATGACGCGTG AAGTGGTAGT GGTAAGCGGT GTCCGTACCG CGATCGGGAC CTTTGGCGGC    60

AGCCTGAAGG ATGTGGCACC GGCGGAGCTG GGCGCACTGG TGGTGCGCGA GGCGCTGGCG   120

CGCGCGCAGG TGTCGGGCGA CGATGTCGGC CACGTGGTAT TCGGCAACGT GATCCAGACC   180

GAGCCGCGCG ACATGTATCT GGGCCGCGTC GCGGCCGTCA ACGGCGGGGT GACGATCAAC   240

GCCCCCGCGC TGACCGTGAA CCGCCTGTGC GGCTCGGGCC TGCAGGCCAT TGTCAGCGCC   300

GCGCAGACCA TCCTGCTGGG CGATACCGAC GTCGCCATCG GCGGCGGCGC GGAAAGCATG   360

AGCCGCGCAC CGTACCTGGC GCCGGCAGCG CGCTGGGGCG CACGCATGGG CGACGCCGGC   420

CTGGTCGACA TGATGCTGGG TGCGCTGCAC GATCCCTTCC ATCGCATCCA CATGGGCGTG   480

ACCGCCGAGA ATGTCGCCAA GGAATACGAC ATCTCGCGCG CGCAGCAGGA CGAGGCCGCG   540

CTGGAATCGC ACCGCCGCGC TTCGGCAGCG ATCAAGGCCG GCTACTTCAA GGACCAGATC   600

GTCCCGGTGG TGAGCAAGGG CCGCAAGGGC GACGTGACCT TCGACACCGA CGAGCACGTG   660

CGCCATGACG CCACCATCGA CGACATGACC AAGCTCAGGC CGGTCTTCGT CAAGGAAAAC   720

GGCACGGTCA CGGCCGGCAA TGCCTCGGGC CTGAACGACG CCGCCGCCGC GGTGGTGATG   780

ATGGAGCGCG CCGAAGCCGA GCGCCGCGGC CTGAAGCCGC TGGCCCGCCT GGTGTCGTAC   840

GGCCATGCCG GCGTGGACCC GAAGGCCATG GGCATCGGCC CGGTGCCGGC GACGAAGATC   900

GCGCTGGAGC GCGCCGGCCT GCAGGTGTCG GACCTGGACG TGATCGAAGC CAACGAAGCC   960

TTTGCCGCAC AGGCGTGCGC CGTGACCAAG GCGCTCGGTC TGGACCCGGC CAAGGTTAAC  1020

CCGAACGGCT CGGGCATCTC GCTGGGCCAC CCGATCGGCG CCACCGGTGC CCTGATCACG  1080

GTGAAGGCGC TGCATGAGCT GAACCGCGTG CAGGGCCGCT ACGCGCTGGT GACGATGTGC  1140

ATCGGCGGCG GCCAGGGCAT TGCCGCCATC TTCGAGCGTA TCTGA                  1185

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Thr Arg Glu Val Val Val Ser Gly Val Arg Thr Ala Ile Gly
1               5                  10                 15

(2) INFORMATION FOR SEQ ID NO:11:

(i) SEQUENCE CHARACTERISTICS:
        (A) LENGTH: 394 amino acids
        (B) TYPE: amino acid
        (C) STRANDEDNESS:
```

(D) TOPOLOGY: linear (ii) MOLECULE TYPE: protein (xi) SEQUENCE DESCRIPTION: SEQ ID NO:11:

Met Thr Arg Glu Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Val Thr Ile Asn
65              70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
            165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
            245                 250                 255

Ala Val Val Met Met Glu Arg Ala Glu Ala Arg Arg Gly Leu Lys
            260                 265                 270

Pro Leu Ala Arg Leu Val Ser Tyr Gly His Ala Gly Val Asp Pro Lys
    275                 280                 285

Ala Met Gly Ile Gly Pro Val Pro Ala Thr Lys Ile Ala Leu Glu Arg
290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
            325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

```
Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390
```